(12) United States Patent
Khurana et al.

(10) Patent No.: US 11,352,668 B2
(45) Date of Patent: Jun. 7, 2022

(54) SPATIAL INDEXING OF GENETIC MATERIAL AND LIBRARY PREPARATION USING HYDROGEL BEADS AND FLOW CELLS

(71) Applicant: ILLUMINA, INC., San Diego, CA (US)

(72) Inventors: Tarun Kumar Khurana, Fremont, CA (US); Yir-Shyuan Wu, Albany, CA (US); Xi-Jun Chen, Belmont, CA (US); Filiz Gorpe-Yasar, Redwood City, CA (US); Yan-You Lin, Fremont, CA (US); Victoria Popic, San Jose, CA (US); Erich B. Jaeger, San Francisco, CA (US); Mostafa Ronaghi, Atherton, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 16/626,115

(22) PCT Filed: Jul. 31, 2018

(86) PCT No.: PCT/US2018/044646
§ 371 (c)(1),
(2) Date: Dec. 23, 2019

(87) PCT Pub. No.: WO2019/028047
PCT Pub. Date: Feb. 7, 2019

(65) Prior Publication Data
US 2020/0216895 A1    Jul. 9, 2020

Related U.S. Application Data

(60) Provisional application No. 62/663,129, filed on Apr. 26, 2018, provisional application No. 62/539,949, filed on Aug. 1, 2017.

(51) Int. Cl.
*C12Q 1/6874* (2018.01)
*C12Q 1/6813* (2018.01)

(52) U.S. Cl.
CPC ......... *C12Q 1/6874* (2013.01); *C12Q 1/6813* (2013.01); *C12Q 2565/514* (2013.01); *C12Q 2600/156* (2013.01)

(58) Field of Classification Search
CPC .. C12Q 1/6874; C12Q 1/6813; C12Q 1/6869; C12Q 2565/514; C12Q 2600/156
See application file for complete search history.

(56) References Cited

U.S. PATENT DOCUMENTS

| | | |
|---|---|---|
| 5,130,238 A | 7/1992 | Malek et al. |
| 5,455,166 A | 10/1995 | Walker |
| 6,172,218 B1 | 1/2001 | Brenner |
| 6,210,891 B1 | 4/2001 | Nyren et al. |
| 6,214,587 B1 | 4/2001 | Dattagupta et al. |
| 6,258,568 B1 | 7/2001 | Nyren |
| 6,274,320 B1 | 8/2001 | Rothberg et al. |
| 6,306,597 B1 | 10/2001 | Macevicz |
| 6,355,431 B1 | 3/2002 | Chee et al. |
| 6,890,741 B2 | 5/2005 | Fan et al. |
| 6,913,884 B2 | 7/2005 | Stuelpnagel et al. |
| 6,969,488 B2 | 11/2005 | Brldgham et al. |
| 7,001,792 B2 | 2/2006 | Sauer et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |

(Continued)

FOREIGN PATENT DOCUMENTS

| | | |
|---|---|---|
| EP | 3 736 281 A1 | 11/2020 |
| WO | 1991/006678 | 5/1991 |

(Continued)

OTHER PUBLICATIONS

Novak et al. ("Single-cell multiplex gene detection and sequencing with microfluidically generated agarose emulsions." Angewandte Chemie International Edition 50.2 (2011): 390-395.). (Year: 2011).*

Bentley, et al., "Accurate whole human genome sequencing using reversible terminator chemistry", Nature, vol. 456, Nov. 2008, 53-59.

Boeke, et al., "Transcription and reverse transcription of retrotransposons", Annu Rev Microbiol 43, 1989, 403-34.

Brown, et al., "Retroviral Integration: Structure of the Initial Covalent Product and Its Precursor, and a Role for the Viral IN Protein", PNAS, 86, 1989, 2525-2529.

Cockroft, et al., "A single-molecule nanopore device detects DNA polymerase activity with single-nucleotide resolution", J. Am. Chem. Soc, 130(3), 2008, 818-820.

(Continued)

*Primary Examiner* — Sahana S Kaup
(74) *Attorney, Agent, or Firm* — Marshall, Gerstein & Borun LLP

(57) ABSTRACT

Implementations of a method for seeding sequence libraries on a surface of a sequencing flow cell that allow for spatial segregation of the libraries on the surface are provided. The spatial segregation can be used to index sequence reads from individual sequencing libraries to increase efficiency of subsequent data analysis. In some examples, hydrogel beads containing encapsulated sequencing libraries are captured on a sequencing flow cell and degraded in the presence of a liquid diffusion barrier to allow for the spatial segregation and seeding of the sequencing libraries on the surface of the flow cell. Additionally, examples of systems, methods and compositions are provided relating to flow cell devices configured for nucleic acid library preparation and single cell sequencing. Some examples include flow cell devices having a hydrogel with genetic material disposed therein, and which is retained within the hydrogel during nucleic acid processing.

25 Claims, 23 Drawing Sheets

(56) References Cited

U.S. PATENT DOCUMENTS

| | | | |
|---|---|---|---|
| 7,427,673 | B2 | 9/2008 | Balasubramanian et al. |
| 7,582,420 | B2 | 9/2009 | Oliphant et al. |
| 7,611,869 | B2 | 11/2009 | Fan |
| 7,622,294 | B2 | 11/2009 | Walt et al. |
| 7,670,810 | B2 | 3/2010 | Gunderson et al. |
| 7,985,565 | B2 | 7/2011 | Mayer et al. |
| 8,003,354 | B2 | 8/2011 | Shen et al. |
| 8,053,192 | B2 | 11/2011 | Bignell et al. |
| 8,563,477 | B2 | 10/2013 | Smith et al. |
| 8,778,848 | B2 | 7/2014 | Lin et al. |
| 8,778,849 | B2 | 7/2014 | Bowen et al. |
| 8,895,249 | B2 | 11/2014 | Shen et al. |
| 9,079,148 | B2 | 7/2015 | Rigatti et al. |
| 9,309,502 | B2 | 4/2016 | Piepenburg et al. |
| 2005/0053980 | A1 | 3/2005 | Gunderson et al. |
| 2005/0100900 | A1 | 5/2005 | Kawashima et al. |
| 2005/0181440 | A1 | 8/2005 | Chee et al. |
| 2006/0188901 | A1 | 8/2006 | Barnes et al. |
| 2006/0240439 | A1 | 10/2006 | Smith et al. |
| 2006/0281109 | A1 | 12/2006 | Barr Ost et al. |
| 2007/0166705 | A1 | 7/2007 | Milton et al. |
| 2008/0108082 | A1 | 5/2008 | Rank et al. |
| 2009/0026082 | A1 | 1/2009 | Rothberg et al. |
| 2009/0127589 | A1 | 5/2009 | Rothberg et al. |
| 2009/0186349 | A1 | 7/2009 | Gunderson et al. |
| 2010/0120098 | A1 | 5/2010 | Grunenwald et al. |
| 2010/0137143 | A1 | 6/2010 | Rothberg et al. |
| 2010/0282617 | A1 | 11/2010 | Rothberg et al. |
| 2011/0172118 | A1 | 7/2011 | Kain et al. |
| 2012/0208724 | A1 | 5/2012 | Steemers |
| 2012/0208705 | A1 | 8/2012 | Steemers et al. |
| 2012/0270305 | A1 | 10/2012 | Reed et al. |
| 2012/0309002 | A1 | 12/2012 | Link |
| 2012/0316086 | A1 | 12/2012 | Lin et al. |
| 2013/0079232 | A1 | 3/2013 | Kaln et al. |
| 2013/0116153 | A1 | 5/2013 | Bowen et al. |
| 2013/0178397 | A1 * | 7/2013 | Rigatti ............... B01J 19/0046 506/30 |
| 2013/0184796 | A1 | 7/2013 | Marzano et al. |
| 2013/0260372 | A1 | 10/2013 | Buermann et al. |
| 2014/0194324 | A1 | 7/2014 | Gormley et al. |
| 2014/0243224 | A1 | 8/2014 | Barnard et al. |
| 2015/0176071 | A1 * | 6/2015 | Fisher ............... C12Q 1/6874 506/2 |
| 2015/0368638 | A1 | 12/2015 | Steemers et al. |

FOREIGN PATENT DOCUMENTS

| | | | |
|---|---|---|---|
| WO | 1995/23875 | 9/1995 | |
| WO | 1998/044151 | 10/1998 | |
| WO | 2000/018957 | 4/2000 | |
| WO | 2004/018497 | 3/2004 | |
| WO | 2005/065814 | 7/2005 | |
| WO | 2006/064199 | 6/2006 | |
| WO | 2007/010251 | 1/2007 | |
| WO | 2007/123744 | 11/2007 | |
| WO | 2008/093098 | 8/2008 | |
| WO | WO-2012005783 A1 * | 1/2012 | ............ A61L 27/16 |
| WO | 2012/061832 | 5/2012 | |
| WO | WO-2012/112804 A1 | 8/2012 | |
| WO | WO-2012/149042 A2 | 11/2012 | |
| WO | WO-2013/126741 A1 | 8/2013 | |
| WO | 2013/184796 | 12/2013 | |
| WO | WO-2014153126 A1 * | 9/2014 | ............ B01J 13/046 |
| WO | WO-2014/210353 A2 | 12/2014 | |
| WO | WO-2014210353 A2 * | 12/2014 | ............ C12Q 1/6813 |
| WO | 2015/002813 | 1/2015 | |
| WO | 2015/106941 | 7/2015 | |
| WO | 2016/066586 | 5/2016 | |
| WO | WO-2016118915 A1 * | 7/2016 | ......... C12N 15/1065 |
| WO | 2016/130704 | 8/2016 | |
| WO | WO-2017/019456 A2 | 2/2017 | |
| WO | 2017/201198 | 11/2017 | |

OTHER PUBLICATIONS

Colegio, et al., "In vitro transposition system for efficient generation of Yandom mutants of Campylobacter jejuni", J. Bacteriol, 183, 2001, 2384-8.

Craig, "Transposon Tn7", Review in: Curr Top Microbiol Immunol, 204, 1996, 27-48.

Craig, "V(D)J recombination and transposition: closer than expected", Science, 271, 1996, 1512.

Deamer, et al., "Characterization of nucleic acids by nanopore analysis", ACC Chem Res, 35(10), 2002, 817-825.

Deamer, et al., "Nanopores and nucleic acids: prospects for ultrarapid sequencing", Trends Biotechnol, 18(4), 2000, 147-151.

Dean, et al., "Comprehensive human genome amplification using multiple displacement amplification", Proc. Natl. Acad. Sci. USA 99,, 2002, 5261-5266.

Devine, et al., "Efficient integration of artificial transposons into plasmid targets in vitro: a useful tool for DNA mapping, sequencing and genetic analysis", Nuc. Acids Res. 22, 1994, 3765-72.

Gloor, "Gene targeting in *Drosophila*", Methods Mol Biol. 260, 2004, 97-114.

Goryshin, et al., "Tn5 in vitro transposition", J. Biol. Chem. 273, 1998, 7367-74.

Grothues, et al., "PCR amplification of megabase DNA with tagged Yandom primers (T-PCR)", Nucleic Acids Research, 21, 1993, 1321-1322.

Healy, "Nanopore-based single-molecule DNA analysis", Nanomed. 2(4), 2007, 459-481.

Ichikawa, et al., "In vitro transposition of transposon Tn3", J Biol Chem, 265, 1990, 18829-32.

Kirby, et al., "Cryptic plasmids of Mycobacterium aviumL Tn552 to the rescue", Molecular Microbiology, 43, 2002, 173-86.

Kleckner, et al., "Tn10 and IS10 transposition and chromosome rearrangements: mechanism and regulation in vivo and in vitro", Curr Top Microbiol Immunol., 204, 1996, 49-82.

Korlach, et al., "Selective aluminum passivation for targeted immobilization of single DNA polymerase molecules in zero-mode waveguide nanostructures", PNAS, vol. 105 No. 4, 2008, 1176-1181.

Lage, et al., "Whole genome analysis of genetic alterations in small DNA samples using hyperbranched strand displacement amplification and array-CGH", Genome Res., 13(2), 2003, 294-307.

Lampe, et al., "A purified mariner transposase is sufficient to mediate transposition in vitro", EMBO J., 15, 1996, 5470-5479.

Levene, et al., "Zero-Mode Waveguides for Single-Molecule Analysis at high concentrations", Science 299, 2003, 682-686.

Li, et al., "DNA molecules and configurations in a solid-state nanopore microscope", Nature Mater, 2(9), 2003, 611-615.

Lundquist, et al., "Parallel confocal detection of single molecules in real time", Opt. Lett. 33(9), 2008, 1026-1028.

Metzker, et al., "Emerging technologies in DNA sequencing", Genome Research, 15, 2005, 1767-1776.

Mizuuchi, "In vitro transposition of bacteriophase Mu: a biochemical approach to a novel replication reaction", Cell, 35, 1983, 785-94.

Ohtsubo, et al., "Bacterial insertion sequences", Curr. Top. Microbiol. Immunol. 204, 1996, 1-26.

Plasterk, "The Tc1/mariner transposon family", Curr Top Microbiol Immunol, 204, 1996, 125-43.

Ronaghi, et al., "A Sequencing Method Based on Real-Time Pyrophosphate", Science 281 (5375), 1998, 363-365.

Ronaghi, et al., "Real-time DNA sequencing using detection of pyrophosphate release", Anal. Biochem. 242 (1):84-9, 242 (1), 1996, 84-89.

Ronaghl, et al.."Pyrosequencing sheds light on DNA sequencing", Genome Res, 11(1), 2001, 3-11.

Ruparel, et al., "Design and synthesis of a 3'-O-allyl photocleavable fluorescent nucleotide as a reversible terminator for DNA sequencing by synthesis", PNAS, 102, 2005, 5932-5937.

Savilahti, et al., "The Phage Mu transpososome core: DNA requirements for assembly and function", EMBO J., 14, 1995, 4893-4903.

Soni, et al., "Progress toward Ultrafast DNA Sequencing Using Solid-State Nanopores", Clin Chem, 53(11), 2007, 1996-2001.

(56) References Cited

OTHER PUBLICATIONS

Walker, et al., "A Chemiluminescent DNA Probe Test Based on Strand Displacement Amplification", Molecular Methods for Virus Detection, 1995, Academic Press Inc. Ch 15 pp. 329-349., 1995, 329-349.

Walker, et al., "Strand displacement amplification-an isothermal, in vitro DNA amplification technique", Nucleic Acids Res., 20, 1992, 1691-1696.

Wilson, et al., "New transposon delivery plasmids for insertional mutagenesis in *Bacillus anthracis*", Journal of Microbiological Methods, 71, 2007, 332-335.
Zhang, et al., "A Novel Mechanism of Transposon-Mediated Gene Activation", PLoS Genetics vol. 5 (10), e1000689, Oct. 2009.

* cited by examiner

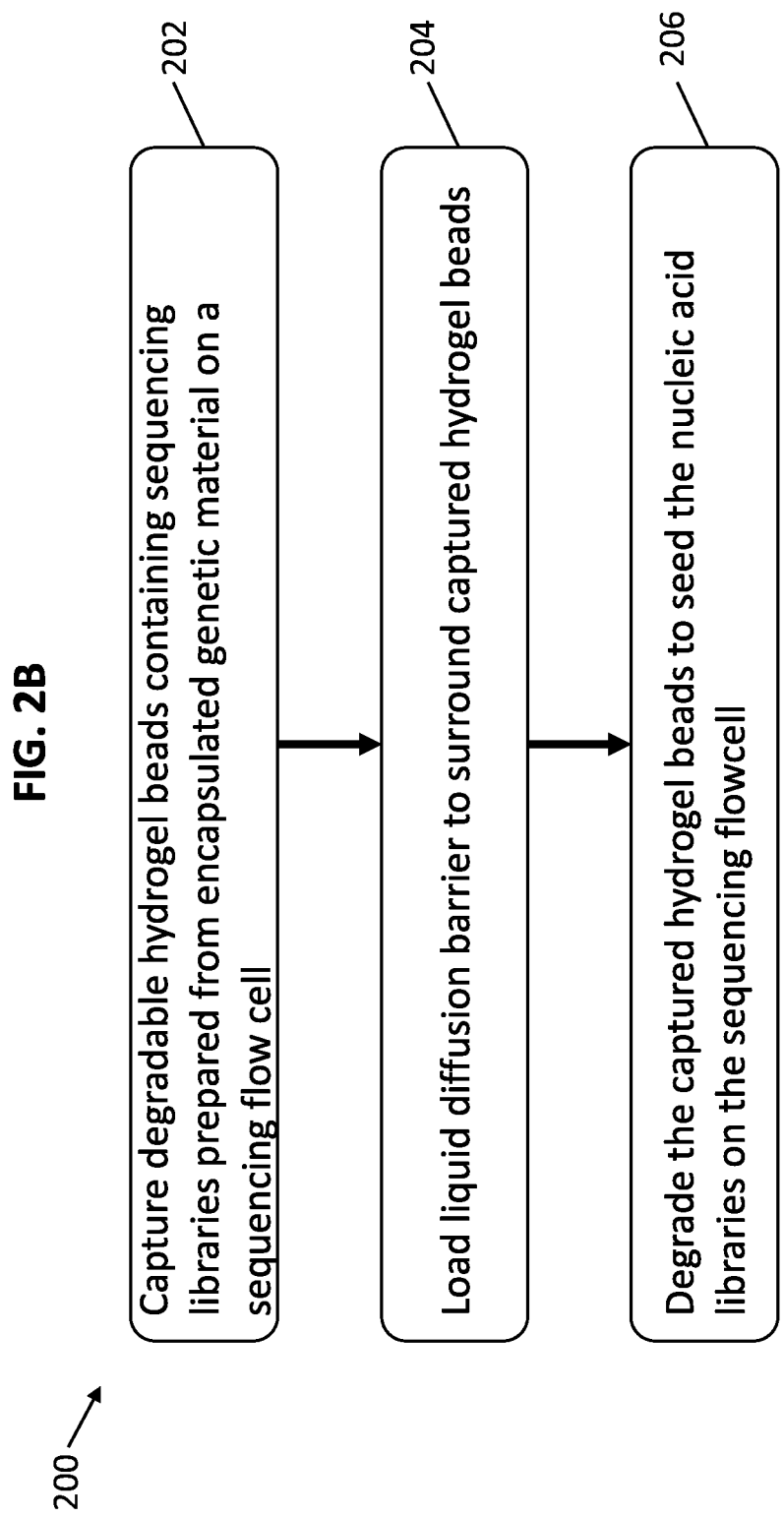

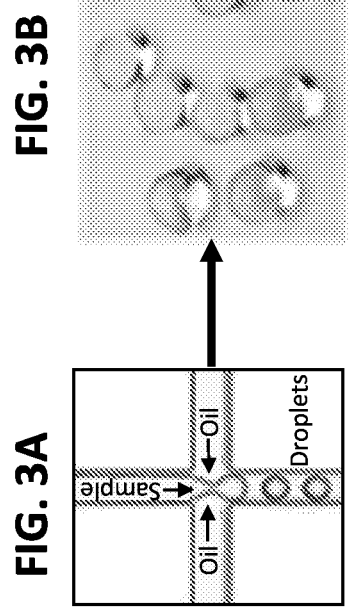
FIG. 3A
FIG. 3B
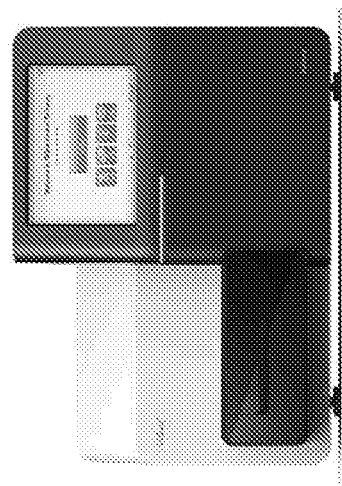
FIG. 3D
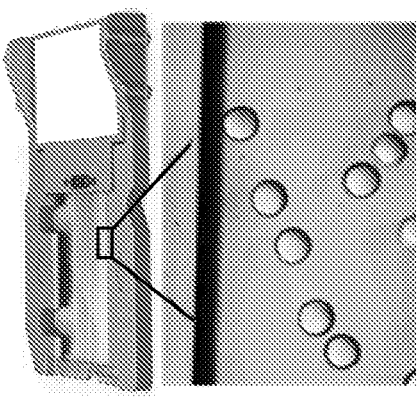
FIG. 3C

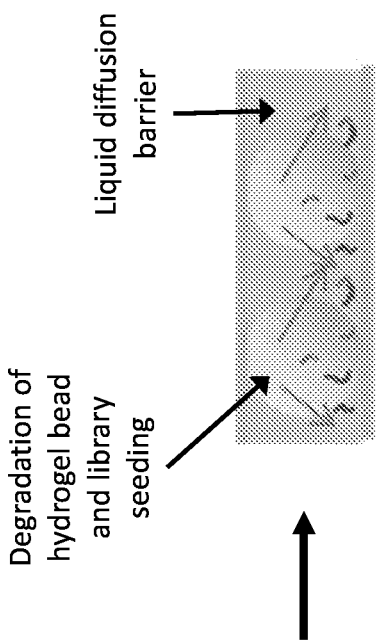
FIG. 4A
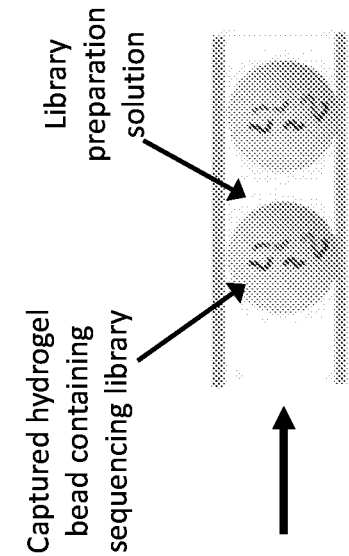
FIG. 4B
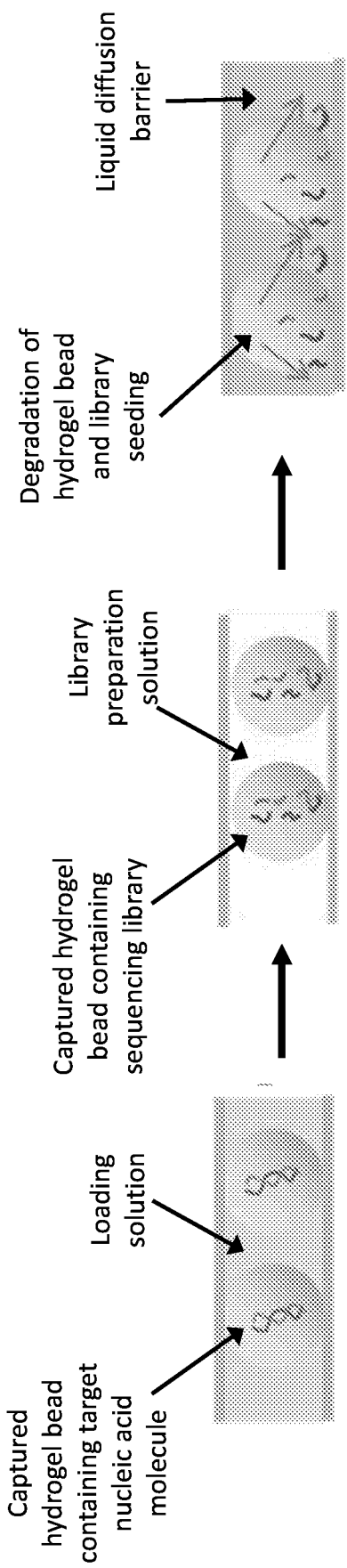
FIG. 4C
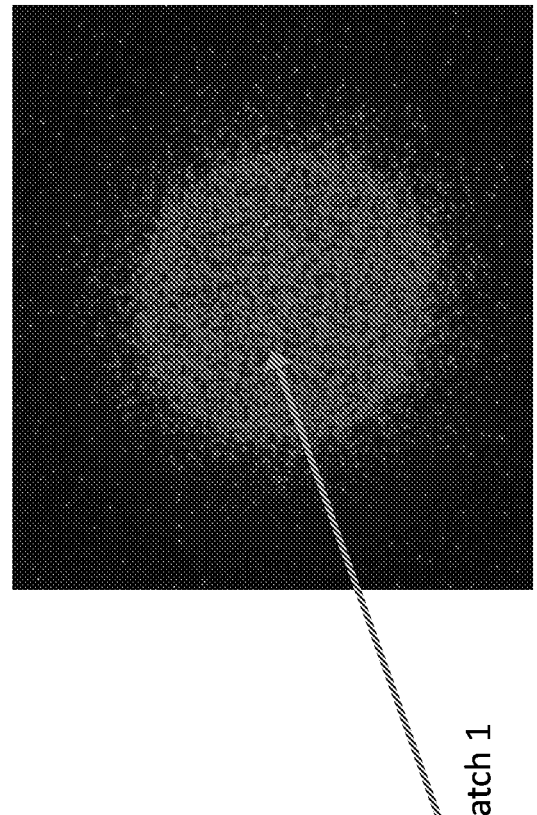

FIG. 5A
~100 kb genomic fragment in hydrogel bead
No MDA
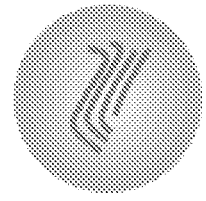
Island size ~100kb
FIG. 5B
~100 kb genomic fragment in hydrogel bead
MDA in Hydrogel
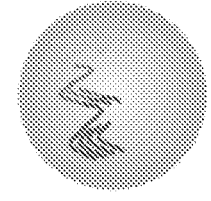
Island size ~100kb
FIG. 5C
10-20 kb genomic fragment in hydrogel bead
MDA in Hydrogel
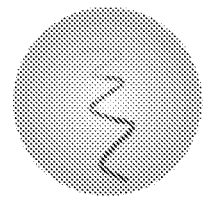
Island size ~10kb

FIG. 8
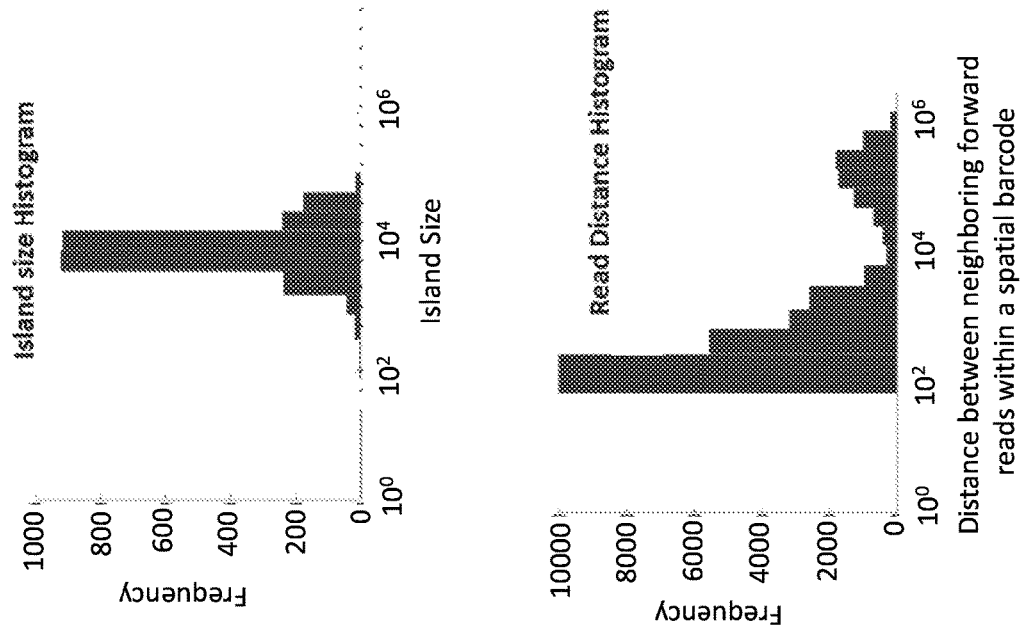
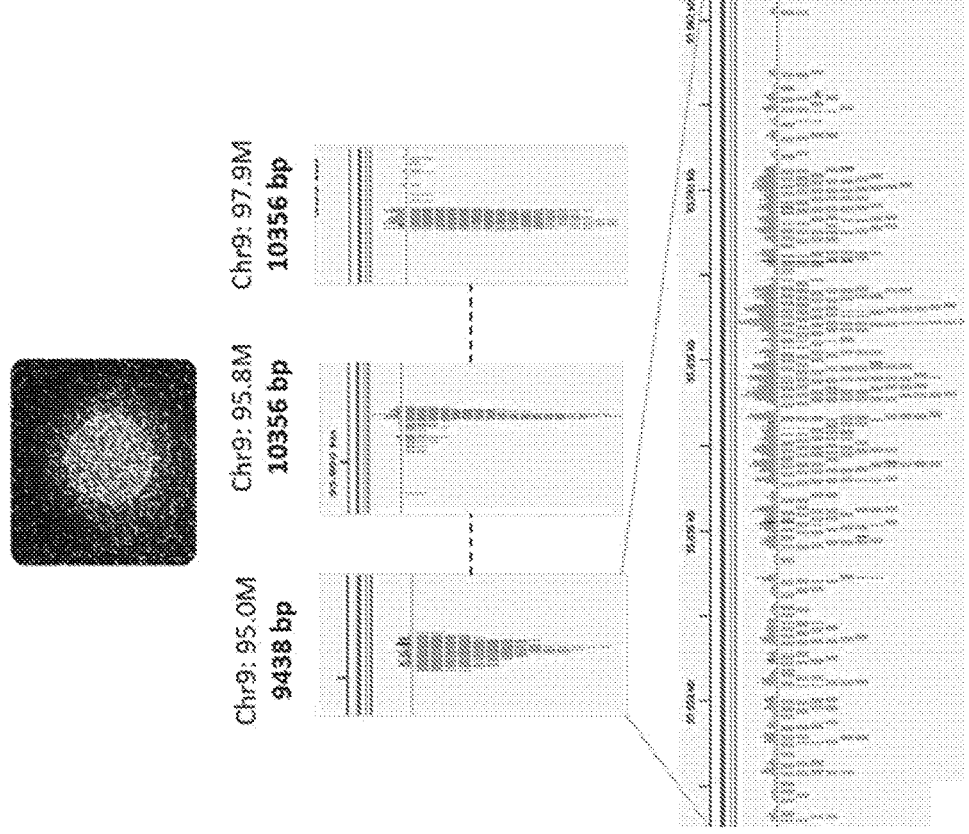

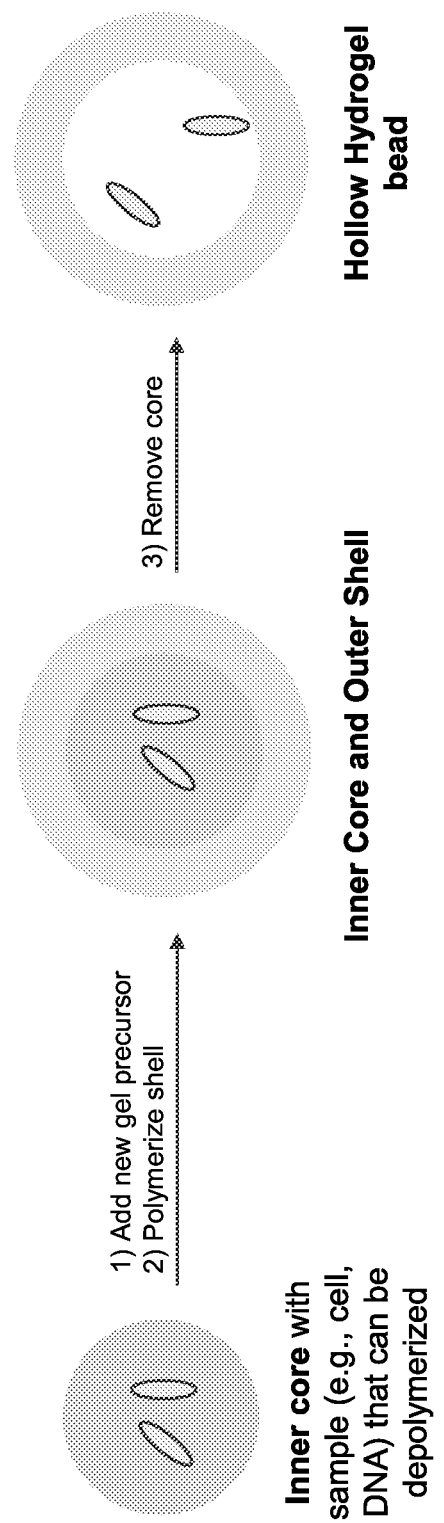

Sequential bead loading and processing for multiplex sample Indexing

Seeded library using hydrogel beads for spatial indexing (after seeding of interstitial space)

↑ Seed additional library to utilize interstitial space

Seeded library using hydrogel beads for spatial indexing (before seeding of interstitial space)

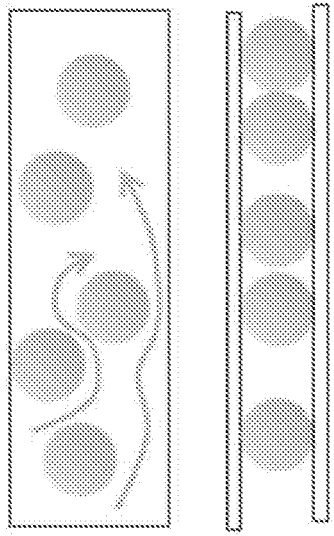
FIG. 14A
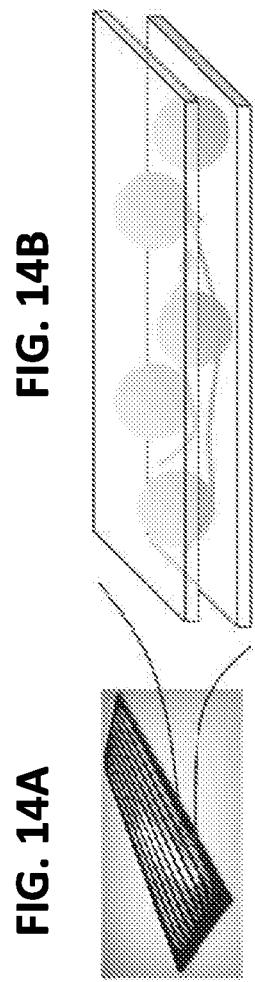
FIG. 14B
FIG. 14C
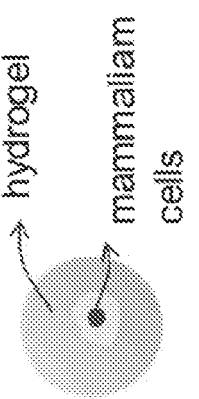
FIG. 14D
hydrogel
microbiome
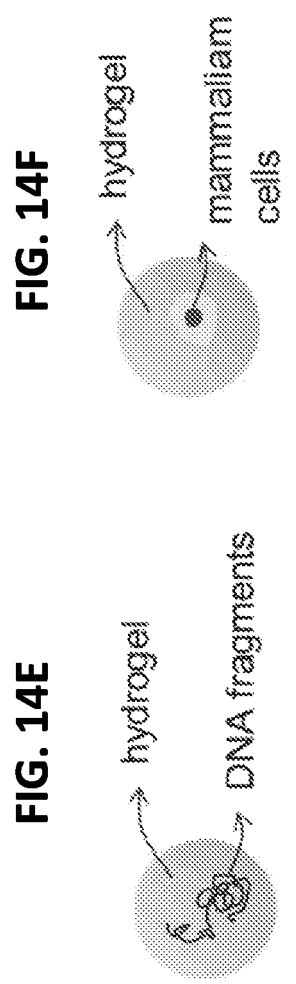
FIG. 14E
hydrogel
DNA fragments
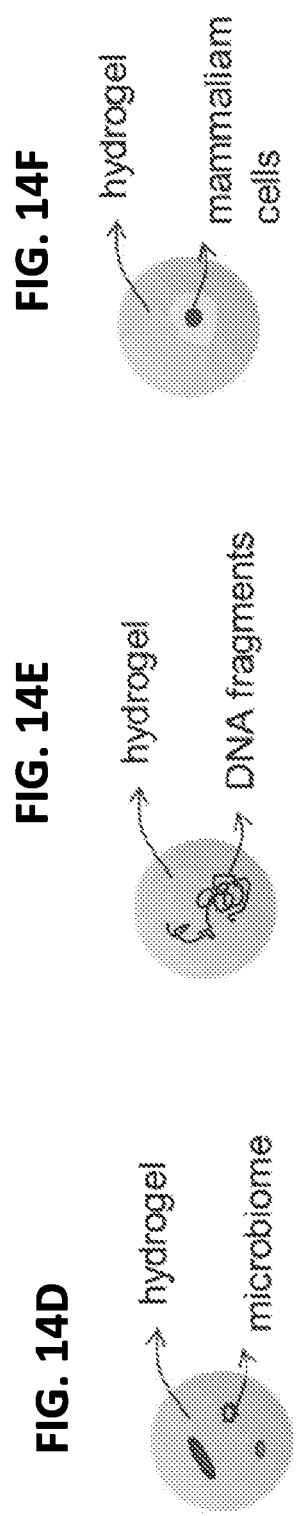
FIG. 14F
hydrogel
mammalian cells pattern flow cell surface to array the hydrogel bead pillars

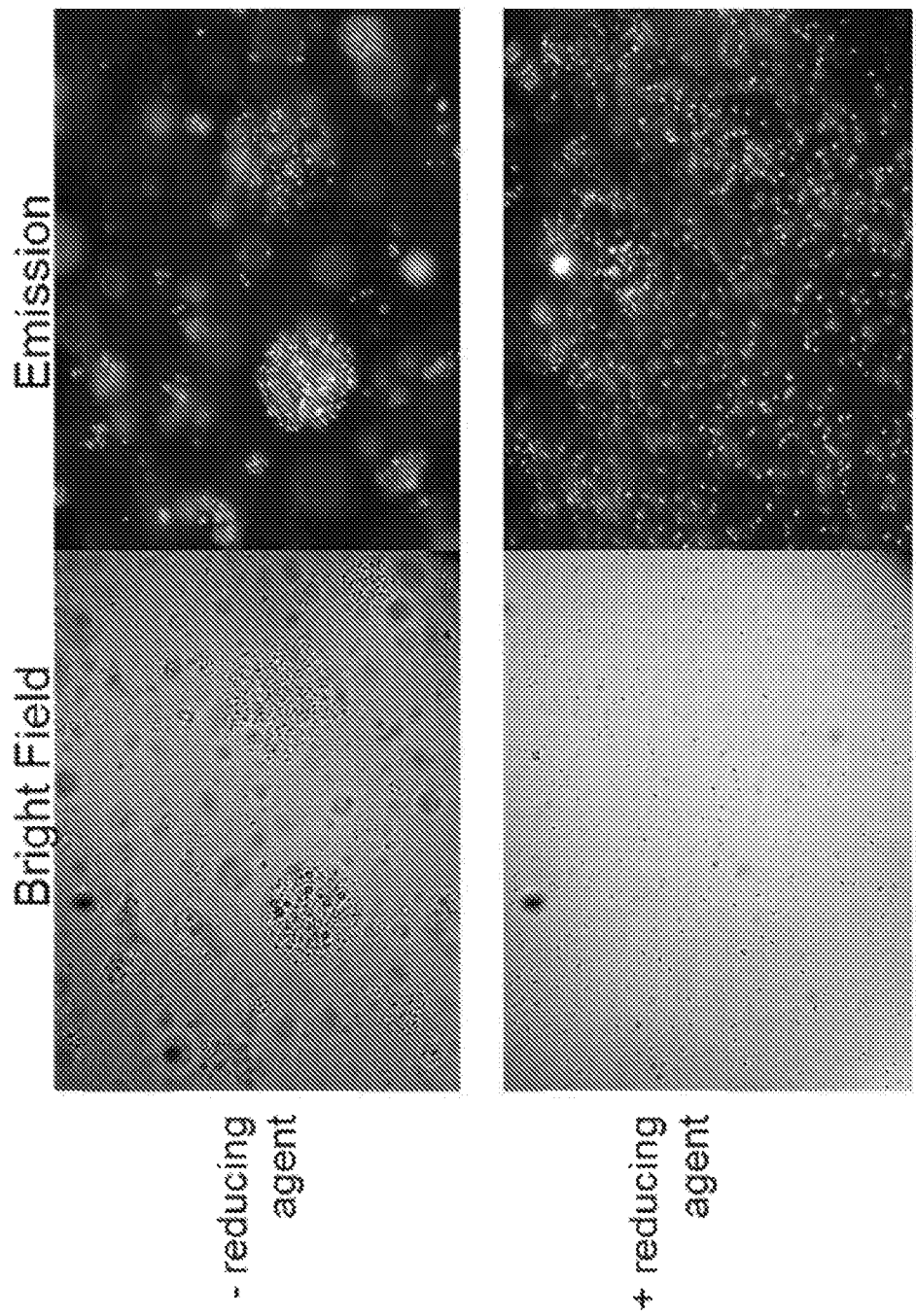

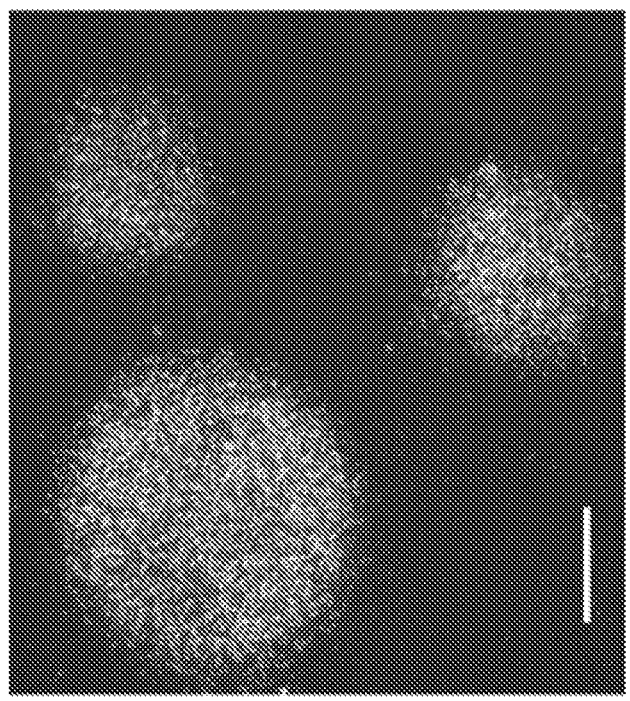
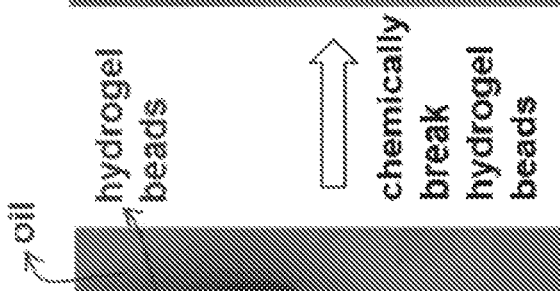
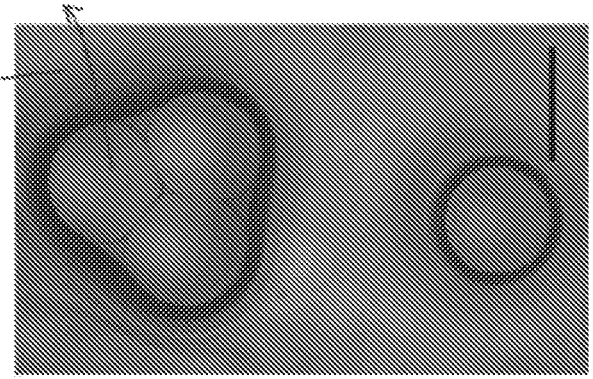
FIG. 18A   FIG. 18B

FIG. 21A
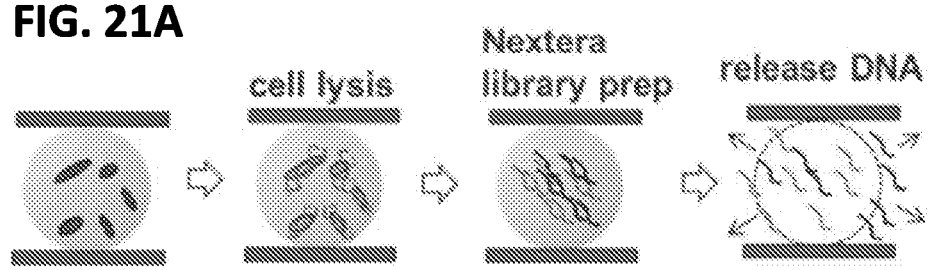
FIG. 21B  FIG. 21C
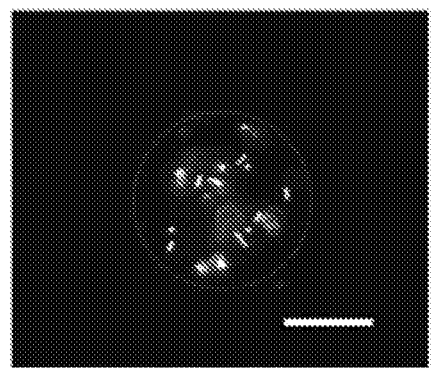 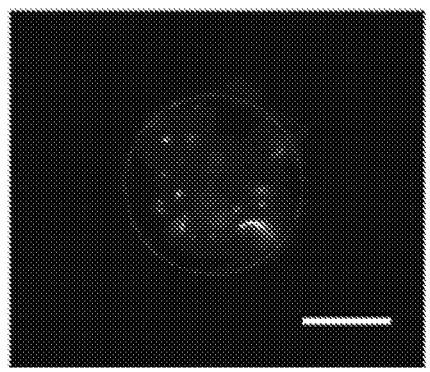
FIG. 21D
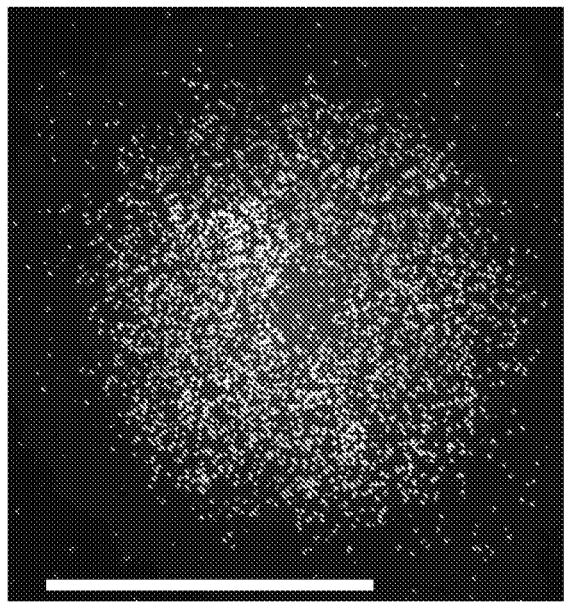

SPATIAL INDEXING OF GENETIC MATERIAL AND LIBRARY PREPARATION USING HYDROGEL BEADS AND FLOW CELLS

RELATED APPLICATIONS

This application is a 35 U.S.C. 371 National Stage of International Patent Application No. PCT/US2018/044646, filed Jul. 31, 2018, which itself claims the benefit of and priority to U.S. Provisional Patent Application Nos. 62/539,949, filed Aug. 1, 2017, and 62/663,129, filed Apr. 26, 2018, the content of each of which is incorporated by reference herein in its entirety and for all purposes.

BACKGROUND

Sequencing-by-synthesis (SBS) technology provides high quality sequencing data. However, SBS methods may be limited by sequence read length, as SBS sequence reads in some instances are no more than 300 nucleotides in length. The short read lengths of SBS technology may involve substantial data analysis to align and reconstruct long nucleic acid sequences from multiple overlapping short sequence reads generated during the SBS procedure. Pre-sequencing steps (such as barcoding of particular nucleic acid molecules) can simplify the data analysis, but also contribute to SBS process complexity.

SUMMARY

Provided herein are examples of a method for seeding sequencing libraries generated from genetic material (for example, target nucleic acid molecules or cells or cell lysate containing target nucleic acid molecules) on a sequencing flow cell that allow for spatial segregation of individual libraries on the flow cell. The spatial segregation can be used to index sequence reads from individual sequencing libraries to increase efficiency of subsequent data analysis. This "spatial indexing" of the sequencing libraries allows for simplified processing and sequence reconstruction of the genetic material from which the sequencing libraries are generated. Among other improvements, the disclosed methods may reduce, and in some instances even obviate, the need for cumbersome barcoding steps to identify sequence reads pertaining to particular genetic material. Examples described herein also increase data resolution for sequencing of target nucleic acid molecules, and further simplify the assembly of genomes (e.g., for of new organisms), and provide improved identification of rare genetic variations and co-occurrence of mutations in target nucleic acid molecules.

In some examples, a method is provided, comprising loading degradable hydrogel beads onto a sequencing flow cell under conditions sufficient for capture of the hydrogel beads on a surface of the sequencing flow cell. In some examples, the degradable hydrogel beads contain sequencing libraries prepared from encapsulated genetic material. In some examples, the degradable hydrogel beads contain encapsulated genetic material, and the method further comprises preparing sequencing libraries in the captured degradable hydrogel beads from the genetic material. A liquid diffusion barrier that surrounds the captured hydrogel beads is then loaded onto the sequencing flow cell, and the captured hydrogel beads are degraded in the presence of the liquid diffusion barrier to allow transport and seeding of the sequencing libraries onto the surface of the sequencing flow cell.

The genetic material can be, for example, target nucleic acid molecules such as genomic DNA (for example, human genomic DNA), as well as cells and cell lysate containing target nucleic acid molecules.

In some examples, the sequencing libraries comprise DNA or RNA of at least 150 nucleotides in length.

In some examples, the liquid diffusion barrier is an oil, such as mineral oil, silicone oil, or perfluorinated oil, or a combination of two or more thereof. In some examples, the liquid diffusion barrier is a viscous aqueous solution, for example, containing poly-ethylene glycol (PEG), poly-vinyl-pyrrolidone, pluronic dextran, sucrose, poly(N-isopropylacrylamide) or polyethylene oxide-polypropylene oxide-polyethylene oxide (PEO—PPO—PEO)/laponite, or a combination of two or more thereof.

In some examples, the degradable hydrogel beads are degraded by one or more of (a) contact with a reagent that cleaves a reversible crosslinker that crosslinks polymers of the hydrogel (such as dithiothreitol (DTT), tris(2-carboxyethyl)phosphine (TCEP), tris(3-hydroxypropyl)phosphine (THP), or a combination of two or more thereof), (b) heating to about 90° C., and (c) by exposing the hydrogel beads to a wavelength of light that cleaves a photo-cleavable crosslinker that crosslinks polymer of the hydrogel.

In some examples, the hydrogel beads have a diameter of from about 5 μm to about 120 μm.

In some examples, the hydrogel beads are hollow hydrogel beads comprising hollow cores comprising the genetic material.

The hydrogel beads comprise pores having a diameter of sufficient size to allow diffusion of reagents through the bead while retaining the encapsulated genetic material and sequencing libraries in the hydrogel bead. In some examples, the pores have a diameter of from about 10 nm to about 100 nm.

In some examples, preparing the sequencing libraries comprises performing a tagmentation reaction on the target nucleic acid molecules encapsulated within the hydrogel beads. For example, the tagmentation reaction can be performed when the hydrogel beads are captured on the sequencing flow cell or prior to loading the hydrogel beads onto the sequencing flow cell. In some examples, the tagmentation reaction comprises contacting the target nucleic acid molecules with a transposase mixture comprising adapter sequences and transposomes.

In some examples, capture of the hydrogel beads on the surface of the sequencing flow cell comprises one or more of: physical constraint of the hydrogel beads on the surface of the sequencing flow cell, and specific binding of a first member of a specific binding pair on the hydrogel beads to a second member of the specific binding pair on the surface of the sequencing flow cell (e.g., located at wells of a patterned flow cell). In some examples, the diameter of the hydrogel beads is from about 5% to about 30% greater than the height of the flow cell to physically constrain the beads in the flow cell. In some examples, the sequencing flow cell is a patterned flow cell, and the second member of the specific binding pair is located at wells of the patterned flow cell.

In some examples of the disclosed method, the diameter of the hydrogel beads is about 110 μm, and the height of the sequencing flow cell is about 100 μm.

Some examples of the disclosed method further comprise amplifying target nucleic acid molecules encapsulated with the degradable hydrogel beads. In some examples, the amplification involves multiple displacement amplification. In some examples, the encapsulated target nucleic acid molecules are genomic DNA and the amplification involves whole-genome amplification.

In some examples, the sequencing libraries are not barcoded to identify individual hydrogel beads. In some examples, the method further comprises sequencing the sequencing libraries seeded on the surface of the flow cell. In some examples, the location on the surface of the flow cell of sequencing libraries seeded from respective degradable hydrogel beads is used as a spatial index for reads generated from the sequencing of the sequence libraries.

Additionally, examples of systems, methods and compositions are provided herein relating to flow cell devices configured for nucleic acid library preparation and for single cell sequencing. In some examples, the flow cell device includes a solid support comprising a surface having a degradable hydrogel deposited thereon. In some examples, the degradable hydrogel comprises pores that are sized to allow diffusion of a reagent through the hydrogel, but are too small to allow genetic material to traverse the pores. Some examples provided herein relate to a system, for example, a system for single cell sequencing. In some examples, the system includes a stage configured to hold a flow cell device as described herein that includes a solid support comprising a surface having a degradable hydrogel deposited thereon, the flow cell device itself, and a detector for obtaining sequencing data. Some examples provided herein relate to a method of preparing a nucleic acid library on a flow cell device. In some examples, the method includes providing a flow cell device as described herein that includes a solid support comprising a surface having a degradable hydrogel deposited thereon, isolating nucleic acids from the genetic material in the hydrogel, and preparing a nucleic acid library from the isolated nucleic acids.

It should be appreciated that all combinations of the foregoing concepts and additional concepts discussed in greater detail below (provided such concepts are not mutually inconsistent) are contemplated as being part of the inventive subject matter disclosed herein.

The foregoing and other features and advantages of this disclosure will become more apparent from the following detailed description of several examples which proceeds with reference to the accompanying figures.

BRIEF DESCRIPTION OF THE DRAWINGS

FIGS. 2A and 2B are flow diagrams of examples of a disclosed method for seeding sequencing libraries produced from genetic material (for example, target nucleic acid molecules such as genomic DNA) on a sequencing flow cell.

FIGS. 3A-3D are schematic illustrations and micrographs showing production and loading of hydrogel beads containing genetic material onto a sequencing flow cell. (FIG. 3A) A solution of target nucleic acid molecules mixed with polymer precursor was loaded into a sample reservoir of a droplet generator cartridge, the cartridge was loaded onto a droplet generator, and processed to generate droplets of polymer precursor containing the target nucleic acid molecules. (FIG. 3B) Micrograph of hydrogel beads containing encapsulated target nucleic acid molecules. In this example, the beads have an average diameter of about 120 µm. The hydrogel beads were formed by exposing the droplets prepared using the droplet generator to radical initiators dissolved in oil, or exposing the droplets to UV irradiation with a UV radical initiator. (FIG. 3C) Illustration and micrograph of the hydrogel beads captured on a sequencing flow cell. In this example, the beads have an average diameter of about 120 µm, and were loaded onto the sequencing flow cell where they were captured due to physical constraint in the 100 µm high channel of the flow cell. (FIG. 3D) The sequencing flow cell was inserted into a SBS sequencer for further processing and sequencing.

FIGS. 4A-4C are schematic illustrations and micrographs showing in-bead sequencing library preparation and flow cell seeding. (FIG. 4A) Schematic diagram showing hydrogel beads containing encapsulated target nucleic acid molecules that were captured on a sequencing flow cell. In this example, the beads have an average diameter of about 120 µm, and were loaded onto the sequencing flow cell where they were captured due to physical constraint in the 100 µm high channel of the flow cell. The captured hydrogel beads had a pore size that allows the diffusion of enzymes, chemicals and smaller sized oligonucleotides (for example, less than 50 base pairs), but retains larger sized nucleic acid molecules (for example, greater than 300 base pairs). (FIG. 4B) Schematic diagram showing in-bead preparation of sequencing library from the target DNA encapsulated within the hydrogel beads. Library preparation solution containing enzymes and reagents for preparation of the sequencing library from the target nucleic acid molecules was loaded onto the flow cell to prepare the sequencing library in the hydrogel bead. In this example, sequencing library preparation was performed by tagmentation assay. (FIG. 4C) Schematic diagram and micrograph showing a liquid diffusion barrier loaded onto the sequencing flow cell to fill the void volume between beads and to surround the captured hydrogel beads containing the sequencing libraries. In this example, the liquid diffusion barrier was mineral oil. The flow cell was then heated to degrade the hydrogel gel beads and allow transport of the sequencing library to the flow cell surface where the sequencing libraries are captured. In another example, mineral oil containing a sufficient concentration of DTT to depolymerize the beads and release the library can be used instead of or in addition to applying heat to the beads. In several implementations, the flow cell is heated to denature the library before seeding. The presence of the mineral oil inhibited diffusion of the sequencing library beyond the diameter of the hydrogel beads. Thus, in the presence of the oil, seeding occurred in close proximity to the footprint of each hydrogel bead (from 120 µm diameter hydrogel beads, library seeding was limited to about 120 µm diameter area).

FIGS. 5A-5C depict schematic illustrations of three different workflows for nucleic acid molecule sequencing.

FIG. 8 depicts sequencing results of flow cell seeded with hydrogel beads containing human genomic DNA having a fragment size of ~10 kb with ~100 fragments per bead. The genomic DNA in the hydrogel beads was amplified by MDA amplification prior to flow cell capture and in-bead library generation.

FIGS. 9A-9C depicts a schematic diagram (FIG. 9A) and a set of micrographs (FIGS. 9B and 9C) illustrating hollow hydrogel beads for use in the disclosed examples. FIG. 9A provides a schematic diagram illustrating construction of the hollow hydrogel beads. First, an inner hydrogel layer (inner core) is formed that contains encapsulated sample (e.g., genetic material, such as a cell or target nucleic acid molecule). The inner core is then encapsulated with an outer hydrogel layer (outer shell). The inner hydrogel layer is then depolymerized using an agent that does not depolymerize the outer hydrogel layer, leaving the outer hydrogel layer with a hollow space containing the genetic material.

FIG. 13A shows steps (a)-(d) for preparing a gel matrix containing cells or genomic DNA on a flow cell surface. FIG. 13B depicts steps (a)-(e) for preparing a nucleic acid library on the flow cell surface of FIG. 1A.

FIGS. 14A-14F depict a schematic representation of trapping of hydrogel beads within a flow cell. In FIGS. 14A-14C hydrogel beads are shown as trapped in a flow cell and used for downstream assays with different reagents. In FIG. 14D a sample of DNA fragments are shown being trapped within hydrogel for on-flow library preparation. In FIG. 14E, a microbiome is shown being trapped within hydrogel for on-flow library preparation. In FIG. 14F, mammalian cells are shown as being trapped inside the hydrogel beads for on-flow cell library preparation.

FIG. 15A shows a cross-section view of the structure of hydrogel beads captured on microarray patterned flow cells. FIG. 15B is a bright field image of rehydrated gel beads located and centered on patterned wells. FIG. 15C is an image that shows fluorescent imaging of rehydrated hydrogel beads in the wells. Scale bar, 50 µm.

In FIG. 16A, hydrogel beads are shown as dehydrated and having an initial size of around 70 µm in diameter. In FIG. 16B, the beads from FIG. 16A are partially rehydrated and begin to enlarge. In FIG. 16C, the beads are fully hydrated at a diameter of about 105 µm. Scale bar, 200 µm.

FIG. 17 shows micrographs of 10-100 µm-sized reversible hydrogel beads illustrating release of encapsulated genetic material from hydrogel beads. Reversible hydrogel beads carrying dye-stained bacteria are shown as degraded upon contact with a reducing agent, resulting in the release of bacteria. Each image is 300 µm×225 µm.

FIGS. 18A-18B depict the results of an experiment of flow cell library preparation and cluster generation using chemically decomposable hydrogel beads. In FIG. 18A, hydrogel beads in oil are shown as merging together. In FIG. 18B, clusters of amplified DNA fragments are shown that have derived from the hydrogel beads shown in FIG. 18A. Scale bar, 100 µm.

FIG. 20A is an overall Q-Score of the reads from a first experiment. FIG. 20B shows the mismatch rate from the same experiment.

FIGS. 21A-21D depict examples of flow cell library preparation and cluster generation and release of DNA libraries from hydrogel beads, as seen with SYTOX intercalator dye. FIG. 21A is a schematic diagram of an example of a library preparation. FIG. 21B is a micrograph showing DNA of lysed bacteria cells in hydrogel bead stained with SYTOX intercalator dye. FIG. 21C is a micrograph of a hydrogel bead during the release of DNA from the hydrogel bead. FIG. 21D is a micrograph of DNA libraries seeded and clustered on a flow cell surface, as shown with SYTOX intercalator dye staining. Scale bar, 100 µm.

DETAILED DESCRIPTION

Figure 1:
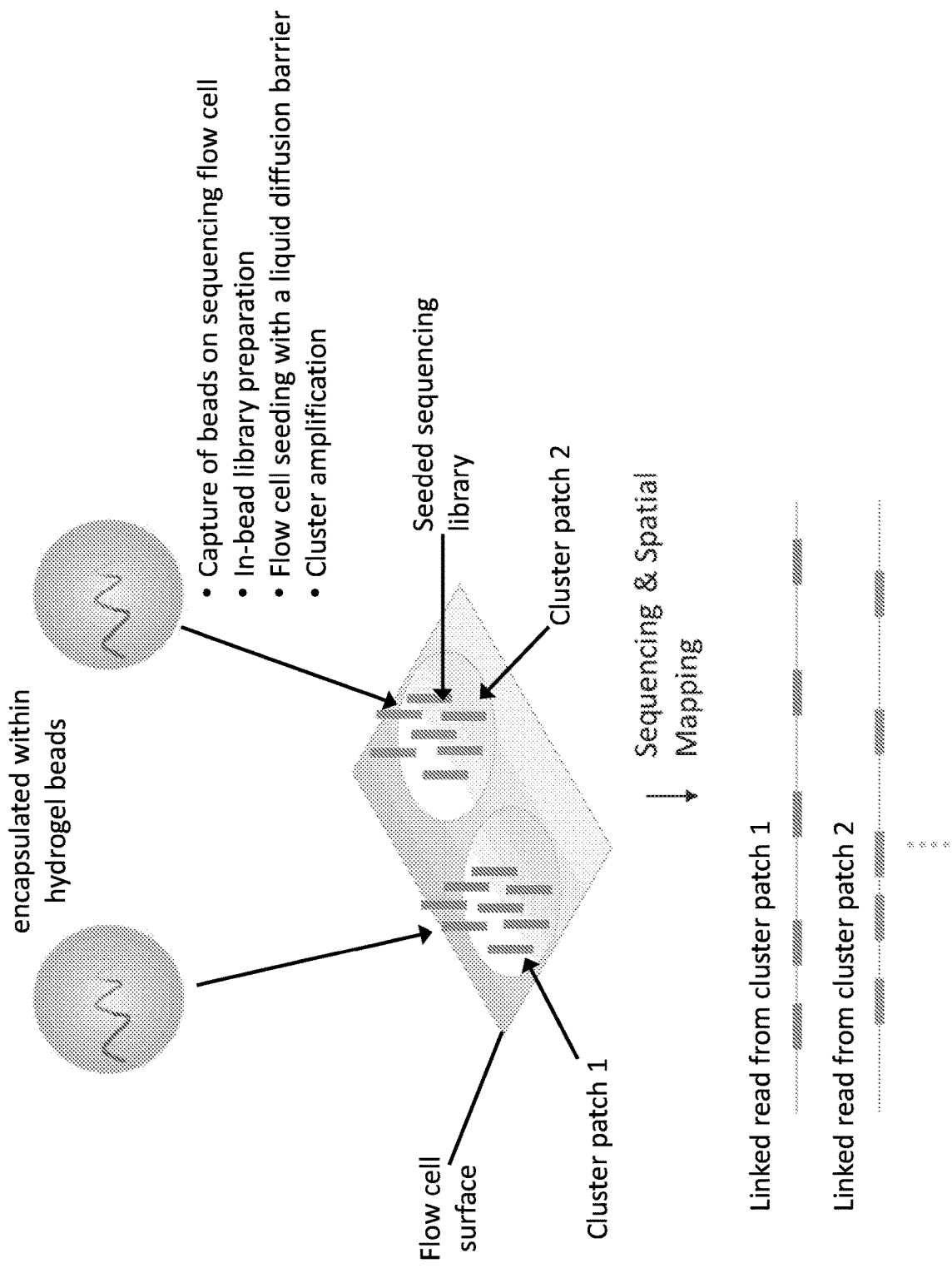
FIG. 1 is a schematic illustration of an example of a disclosed method for seeding sequencing libraries produced from genetic material (for example, target nucleic acid molecules such as genomic deoxyribonucleic acid (DNA)) on a sequencing flow cell and sequencing the sequencing libraries.

Provided herein are examples of a method for seeding a plurality of sequence libraries on a sequencing flow cell that allow for spatial segregation of the libraries in the plurality. The spatial segregation can be used to index sequence reads from individual sequencing libraries to increase efficiency of subsequent data analysis.

Additional implementations pertain to devices, systems, and methods for preparing nucleic acid libraries on a flow cell device. For example, the flow cell device may include a hydrogel that includes genetic material, wherein the hydrogel may be configured to retain the genetic material, while allowing reagents, enzymes, chemicals, and smaller sized primers of less than about 50 base pairs to pass through the hydrogel.

In some examples of the standard sample preparation methods, each template contains an adapter at either end of the insert and often a number of steps are used to both modify the nucleic acid and to purify the desired products of the modification reactions. These steps are performed in solution prior to the addition of the adapted fragments to a flow cell where they are coupled to the surface by a primer extension reaction that copies the hybridized fragment onto the end of a primer covalently attached to the surface. These seeding templates then give rise to monoclonal clusters of copied templates through several cycles of amplification.

The number of steps involved to transform nucleic acids into adapter-modified templates in solution ready for cluster formation and sequencing can be reduced, or in some instances even minimized, by the use of transposase mediated fragmentation and tagging. This process, referred to herein as "tagmentation," involves the modification of nucleic acids by a transposome complex comprising transposase enzyme complexed with adapters comprising transposon end sequence. Tagmentation may result in the simultaneous fragmentation of the DNA and ligation of the adapters to the 5' ends of both strands of duplex fragments. In one example, following a purification step to remove the transposase enzyme, additional sequences are added to the ends of the adapted fragments by PCR. In some instances, solution-based tagmentation has drawbacks and may involve several labor-intensive steps. Additionally, bias can be introduced during PCR amplification steps.

The devices, systems, and methods presented herein overcome these drawbacks and allow unbiased sample preparation, cluster formation, and sequencing to occur on a single solid support with minimal requirements for sample manipulation or transfer, and also allow for sequencing of distinct genetic material, for example, single cell sequencing, on a solid support. In some implementations, spatial indexing of the sequencing libraries allows for simplified processing and sequence reconstruction of genetic material (for example, target nucleic acid molecules) from which sequencing libraries are generated (for example, by reducing the need for a barcoding step). Implementations described herein also increase data resolution for sequencing of target nucleic acid molecules, and further simplify the assembly of genomes (e.g., for new organisms), and provide improved identification of rare genetic variations and co-occurrence of mutations in target nucleic acid molecules.

I. Summary of Terms

Unless otherwise noted, technical terms are used according to conventional usage. As used herein, the singular forms "a," "an," and "the," refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particular suitable methods and materials are described herein. Unless context indicates otherwise, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one example," "an example," "certain examples," or "some examples," etc., means that a particular feature, configuration, composition, or characteristic described in connection with the example is included in at least one example of the disclosure. Thus, the appearances of such phrases in various places throughout this specification are not necessarily referring to the same example of the disclosure.

In this disclosure, reference is made to the accompanying drawings, which form a part hereof. In the drawings, similar symbols identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

For any method disclosed herein that includes discrete steps, the steps may be conducted in any feasible order. And, as appropriate, any combination of two or more steps may be conducted simultaneously. Furthermore, the particular features, configurations, compositions, or characteristics may be combined in any suitable manner in one or more examples.

In case of conflict, the present specification, including explanations of terms, will control. To facilitate review of the various examples, the following explanations of terms are provided:

Adapter: A linear oligonucleotide that can be fused to a nucleic acid molecule, for example, by ligation or tagmentation. In some examples, the adapter is substantially non-complementary to the 3' end or the 5' end of any target sequence present in the sample. In some examples, suitable adapter lengths are in the range of about 10-100 nucleotides, about 12-60 nucleotides, or about 15-50 nucleotides in length. Generally, the adapter can include any combination of nucleotides and/or nucleic acids. In some aspects, the adapter can include one or more cleavable groups at one or more locations. In another aspect, the adapter can include a sequence that is complementary to at least a portion of a primer, for example a primer including a universal nucleotide sequence, such as a P5 or P7 sequence. In some examples, the adapter can include a barcode (also referred to herein as a tag or index) to assist with downstream error correction, identification, or sequencing. The terms "adapter" and "adaptor" are used interchangeably.

In some examples, an adapter can be modified to prevent the formation of concatemers, for example by the addition of blocking groups that prevent extension of the adapter at one or both ends. Examples of 3' blocking groups include a 3'-spacer C3, a dideoxynucleotide, and attachment to a substrate. Examples of 5' blocking groups include a dephosphorylated 5' nucleotide, and attachment to a substrate.

In some examples, the adapter can include a spacer polynucleotide, which may be from about 1 to about 20, such as about 1 to about 15, or about 1 to about 10, nucleotides, such as about 2, about 3, about 4, about 5, about 6, about 7, about 8, about 9, or about 10 nucleotides in length. In some examples, the spacer includes 10 nucleotides. In some examples, the spacer is a polyT spacer, such as a 10T spacer. Spacer nucleotides may be included at the 5' ends of polynucleotides, which may be attached to a suitable support via a linkage with the 5' end of the polynucleotide. Attachment can be achieved through a sulphur-containing nucleophile, such as phosphorothioate, present at the 5' end of the polynucleotide. In some examples, the polynucleotide will include a polyT spacer and a 5' phosphorothioate group.

Amplify, Amplifying, and Amplification: An action or process whereby at least a portion of a nucleic acid molecule is replicated or copied into at least one additional nucleic acid molecule. In some examples, such amplification can be performed using isothermal conditions; in other examples, such amplification can include thermocycling. In some examples, the amplification is a multiplex amplification that includes the simultaneous amplification of a plurality of target sequences in a single amplification reaction. Non-limiting examples of amplification reactions include polymerase chain reaction (PCR), ligase chain reactions, strand displacement amplification reaction (SDA), rolling circle amplification reaction (RCA), multiple annealing and looping based amplification cycles (MALBAC), transcription-mediated amplification (TMA) methods such as NASBA, loop mediated amplification methods (e.g., "LAMP" amplification using loop-forming sequences. The nucleic acid molecule that is amplified can be DNA comprising, consisting of, or derived from DNA or ribonucleic acid (RNA) or a mixture of DNA and RNA, including modified DNA and/or RNA. The products resulting from amplification of a nucleic acid molecule or molecules (for example, "amplification products" or "amplicons"), whether the starting nucleic acid is DNA, RNA or both, can be either DNA or RNA, or a mixture of both DNA and RNA nucleosides or nucleotides, or they can comprise modified DNA or RNA nucleosides or nucleotides. A "copy" does not necessarily mean perfect sequence complementarity or identity to the target sequence. For example, copies can include nucleotide analogs such as deoxyinosine or deoxyuridine, intentional sequence alterations (such as sequence alterations introduced through a primer comprising a sequence that is hybridizable, but not complementary, to the target sequence, and/or sequence errors that occur during amplification.

Several examples include solid-phase amplification, which is an amplification reaction carried out on or in association with a solid support such that all or a portion of the amplified products are immobilized on the solid support as they are formed. Non-limiting examples of solid-phase amplification include solid-phase polymerase chain reaction (solid-phase PCR) and solid phase isothermal amplification, which are reactions analogous to standard solution phase amplification, except that one or both of the forward and reverse amplification primers is/are immobilized on the solid support.

Amplification site: A site on a surface of a sequencing flow cell where one or more amplicons of an amplification reaction can be generated. An amplification site can be further configured to capture, hold or attach at least one amplicon that is generated at the site.

Array: A population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Example features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Example arrays in which separate substrates are located on a surface include, without limitation, those having beads in wells.

Capture: Immobilization of a target entity (such as a hydrogel bead) on a surface of interest (such as a flow cell surface). A capture site is a site on a surface of a sequencing flow cell where one or more hydrogel beads or adapted fragments of a target nucleic acid molecule can be captured.

Capture agent: A material, chemical, molecule or moiety thereof that is capable of attaching, retaining or binding to a target molecule (e.g. a target nucleic acid). Example capture agents include, without limitation, a capture nucleic acid (also referred to herein as a capture oligonucleotide) that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

Hydrogel and Hydrogel Bead: A colloid gel formed from an organic polymer (natural or synthetic) that is cross-linked via covalent, ionic, or hydrogen bonds to create a three-dimensional open-lattice structure that entraps water molecules to form the gel. In several examples, the hydrogel beads are spherical in shape, although other shapes are also possible. In some examples, the hydrogel and hydrogel beads used in the disclosed methods include 60-90% fluid, such as water, and 10-30% polymer. In certain examples, the water content of hydrogel or hydrogel beads is about 70-80%.

A biocompatible hydrogel or hydrogel bead is a hydrogel or hydrogel bead that is not toxic to living cells, and allows sufficient diffusion of oxygen and nutrients to the entrapped cells to maintain viability.

A degradable hydrogel or hydrogel bead is a hydrogel or hydrogel bead that can be selectively de-polymerized. The de-polymerization reduces or destroys the lattice structure of the hydrogel, which increases porosity to an extent that large nucleic acid molecules (e.g., greater than 1 kb) can diffuse through the hydrogel. The degradation time is a function of polymer composition and morphology.

Hydrogel porosity: The fractional volume (dimensionless) of a hydrogel that is composed of open space, for example, pores or other openings. Therefore, porosity measures void spaces in a material and is a fraction of volume of voids over the total volume, as a percentage between 0 and 100% (or a fraction between 0 and 1). In some examples, the porosity of the hydrogel may range from about 50% to about 99%, from about 75% to about 99%, or from about 80% to about 95%.

Index: A sequence of nucleotides that can be used as a molecular identifier and/or barcode to tag a nucleic acid, and/or to identify the source of a nucleic acid. In some examples, an index can be used to identify a single nucleic acid, or a subpopulation of nucleic acids.

Liquid diffusion barrier: A liquid in which polynucleotides have little to no solvation. The sequencing libraries disclosed herein are poorly soluble in liquid diffusion barriers. In a non-limiting example, the liquid diffusion barrier is oil, such as mineral oil. Additional liquid diffusion barriers include viscous solutions that impede diffusion of DNA libraries such as buffers containing polymers such as polyethylene glycol (PEG), poly-vinyl-pyrrolidone, pluronic dextran, sucrose, and the like. The liquid diffusion barrier can also be a temperature responsive gel, where it is a non-viscous solution at non-seeding temperatures, and upon heating to the seeding conditions turns into a gel and forms a barrier for DNA diffusion. Examples include poly(N-isopropylacrylamide) and polyethylene oxide-polypropylene oxide-polyethylene oxide (PEO—PPO—PEO)/laponite nanoparticle composites.

Nucleic acid molecule: a polymeric form of nucleotides of any length, and may include ribonucleotides, deoxyribonucleotides, analogs thereof, or mixtures thereof. The terms should be understood to include, as equivalents, analogs of either DNA or RNA made from nucleotide analogs and to be applicable to single stranded (such as sense or anti sense) and double stranded polynucleotides. The term as used herein also encompasses cDNA, that is complementary or copy DNA produced from an RNA template, for example by the action of reverse transcriptase. This term refers only to the primary structure of the molecule. Thus, the term includes triple-, double- and single-stranded DNA, as well as triple-, double- and single-stranded RNA. The terms nucleic acid molecule and polynucleotide are used interchangeably herein.

The term "target," when used in reference to a nucleic acid molecule, is intended as a semantic identifier for the nucleic acid in the context of a method set forth herein and does not necessarily limit the structure or function of the nucleic acid beyond what is otherwise explicitly indicated.

The nucleotides in the nucleic acid molecule can include naturally occurring nucleic acids and functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in DNA) or a ribose sugar (e.g. found in RNA). A nucleic acid can contain any of a variety of analogs of these sugar moieties that are known in the art. A nucleic acid can include native or non-native bases. In this regard, a native DNA can have one or more bases selected from the group consisting of adenine, thymine, cytosine or guanine and a ribonucleic acid can have one or more bases selected from the group consisting of adenine, uracil, cytosine or guanine. Useful non-native bases that can be included in a nucleic acid are known in the art. Examples of non-native bases include a locked nucleic acid (LNA) and a bridged nucleic acid (BNA). LNA and BNA bases can be incorporated into a DNA oligonucleotide and increase oligonucleotide hybridization strength and specificity.

P5 and P7: P5 and P7 may be used when referring to a universal P5 or P7 sequence or P5 or P7 primer for capture and/or amplification purposes. P5' and P7' designate to the complement of P5 and P7, respectively. It will be understood that any suitable universal sequence can be used in the methods presented herein, and that the use of P5 and P7 are examples only. In some examples, the P5 sequence comprises a sequence defined by SEQ ID NO: 1 (AATGATACGGCGACCACCGA) and the P7 sequence comprises a sequence defined by SEQ ID NO: 2 (CAAGCAGAAGACGGCATACGA). Non-limiting uses of P5 and P7 or their complements on flow cells are exemplified by the disclosures of WO 2007/010251, WO 2006/064199, WO 2005/065814, WO 2015/106941, WO 1998/044151, and WO 2000/018957, each of which is incorporated by reference herein in its entirety.

Primer: A nucleic acid molecule that can hybridize to a target sequence of interest. In several implementations, the primer functions as a substrate onto which nucleotides can be polymerized by a polymerase. However, in some examples, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some examples, the primer is a single-stranded oligonucleotide or polynucleotide.

Reagent: An agent or a mixture of two or more agents useful for reacting with, interacting with, diluting, or adding to a sample, and may include, for example, agents used in nucleic acid amplification, tagmentation, and sequencing reactions, including, for example buffers, chemicals, enzymes, polymerase, primers having a size of less than 50 base pairs, template nucleic acids, nucleotides, labels, dyes, or nucleases. In some examples, the reagent includes lysozyme, proteinase K, random hexamers, polymerase (for example, Φ29 DNA polymerase, Taq polymerase, Bsu polymerase), transposase (for example, Tn5), primers (for example, P5 and P7 adapter sequences), ligase, catalyzing enzyme, deoxynucleotide triphosphates, buffers, or divalent cations. In some examples, reagents can include lysis agents, nucleic acid purification agents, DNA amplification agents, tagmentation agents, PCR agents, or other agents used in processing of genetic materials.

Seeding a sequencing library: Immobilization of adapted fragments of a target nucleic acid molecule on a solid support a sequencing flow cell.

Sequencing flow cell: A chamber comprising a surface across which one or more fluid reagents can be flowed and to which adapted fragments of sequencing libraries can transport and bind. Non-limiting examples of sequencing flow cells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and U.S. 2008/0108082, each of which is incorporated by reference herein in its entirety.

A sequencing flow cell includes a solid support having a surface on which sequencing libraries bind. In some examples, the surface contains a lawn of capture nucleotides that can bind to adapted fragments of a sequencing library. In some examples, the surface is a patterned surface. A "patterned surface" refers to an arrangement (such as an array) of different regions (such as amplification sites) in or on an exposed surface of a solid support. For example, one or more of the regions can be features where one or more amplification and/or capture primers are present. The features can be separated by interstitial regions where primers are not present. In some examples, the pattern can be an x-y format of features that are in rows and columns. In some examples, the pattern can be a repeating arrangement of features and/or interstitial regions. In some examples, the pattern can be a random arrangement of features and/or interstitial regions. In some examples, the surface is a patterned surface that contains an array of wells with capture and/or amplification nucleotides that bind to adapted fragments of a sequencing library, with interstitial regions between the wells that lack the capture and/or amplification nucleotides.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide) (PAZAM, see, for example, U.S. Pub. No. 2013/184796, WO 2016/066586, and WO 2015/002813, each of which is incorporated by reference herein in its entirety). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However, in many examples the gel need not be covalently linked to the wells. For example, in some conditions silane free acrylamide (SFA, see, for example, U.S. Pat. No. 8,563,477, which is incorporated by reference herein in its entirety) which is not covalently attached to the wells of the surface, can be used as the gel material. Examples of flow cells with patterned surfaces that can be used in the methods set forth herein are described in U.S.

Pat. Nos. 8,778,848, 8,778,849 and 9,079,148, and U.S. Pub. No. 2014/0243224, each of which is incorporated by reference herein in its entirety.

The features in a patterned surface can have at any of a variety of densities including, for example, at least about 10 (such as at least about 100, at least about 500, at least about 1000, at least about 5,000, at least about 10,000, at least about 50,000, at least about 100,000, at least about 1,000,000, or at least about 5,000,000, or more) features/cm$^2$.

Sequencing library: A collection of nucleic acid fragments of one or more target nucleic acid molecules, or amplicons of the fragments. In several implementations, the nucleic acid fragments of the sequencing library are linked to known universal sequences (such as P5 and P7 sequences) at their 3' and 5' ends. In several examples a sequencing library is prepared from one or more target nucleic acid molecules encapsulated within a hydrogel or hydrogel bead as described herein.

Tagmentation: Modification of a nucleic acid molecule by a transposome complex to fragment the nucleic acid molecule and ligate adapters to the 5' and 3' ends of the fragments in a single step. Tagmentation reactions can be used for preparation of sequencing libraries. Tagmentation reactions combine random fragmentation and adapter ligation into a single step to increase the efficiency of the sequencing library preparation process.

Transport: Movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecule in a desired direction or to a desired location such as an amplification site.

Transposome complex: An integration enzyme and a nucleic acid including an integration recognition site. A transposome complex is a functional complex formed by a transposase and a transposase recognition site that is capable of catalyzing a transposition reaction (see, for instance, Gunderson et al., WO 2016/130704). Examples of integration enzymes include, but are not limited to, an integrase or a transposase. Examples of integration recognition sites include, but are not limited to, a transposase recognition site.

Under conditions sufficient for: A phrase that is used to describe any environment that permits a desired activity.

Universal nucleotide sequence: A region of sequence that is common to two or more nucleic acid molecules where the molecules also have regions of sequence that differ from each other. A universal sequence that is present in different members of a collection of molecules can allow capture of multiple different nucleic acids using a population of universal capture nucleic acids, e.g., capture oligonucleotides that are complementary to a portion of the universal sequence, e.g., a universal capture sequence. Non-limiting examples of universal capture sequences include sequences that are identical to or complementary to P5 and P7 primers. Similarly, a universal sequence present in different members of a collection of molecules can allow the amplification or replication (e.g., sequencing) of multiple different nucleic acids using a population of universal primers that are complementary to a portion of the universal sequence, e.g., a universal anchor sequence. A capture oligonucleotide or a universal primer therefore includes a sequence that can hybridize specifically to a universal sequence. Two universal sequences that hybridize are referred to as a universal binding pair. For instance, a capture oligonucleotide and a universal capture sequence that hybridize are a universal binding pair.

II. Spatial Indexing and Sequencing of Target Nucleic Acid Molecules

Provided herein are examples of a method for seeding a plurality of sequence libraries on a sequencing flow cell that allow for spatial segregation of the libraries in the plurality. The spatial segregation can be used to index sequence reads from individual sequencing libraries to increase efficiency of subsequent data analysis. This "spatial indexing" of the sequencing libraries allows for simplified processing and sequence reconstruction of the target nucleic acid molecules from which the sequencing libraries are generated. Among other improvements, the disclosed methods obviate the need for cumbersome barcoding steps to identify sequence reads pertaining to a particular target nucleic acid molecule. Implementations described herein also increase data resolution for sequencing of target nucleic acid molecules, and further simplify the assembly of genomes (e.g., for of new organisms), and provide improved identification of rare genetic variations and co-occurrence of mutations in target nucleic acid molecules.

FIG. 1 illustrates certain features of the disclosed examples, which are described in detail herein. As shown in FIG. 1, in some examples of the disclosed method, hydrogel beads containing encapsulated target nucleic acid molecules are captured on a sequencing flow cell. Sequencing libraries are prepared from the target nucleic acid molecules encapsulated in the hydrogel beads, and the sequencing libraries are seeded onto the flow cell surface in the presence of a liquid diffusion barrier, which results in spatially segregated seeding of the sequencing libraries from individual hydrogel beads. In the illustrated example, the two seeded sequencing libraries are amplified by cluster amplification, forming two groups of clusters termed "cluster-patches." The spatial indexing of the cluster patches on the flow cell surface enables the target nucleic acid molecule sequence to be reconstructed from shorter sequence reads from individual cluster-patches.

Figure 2A:
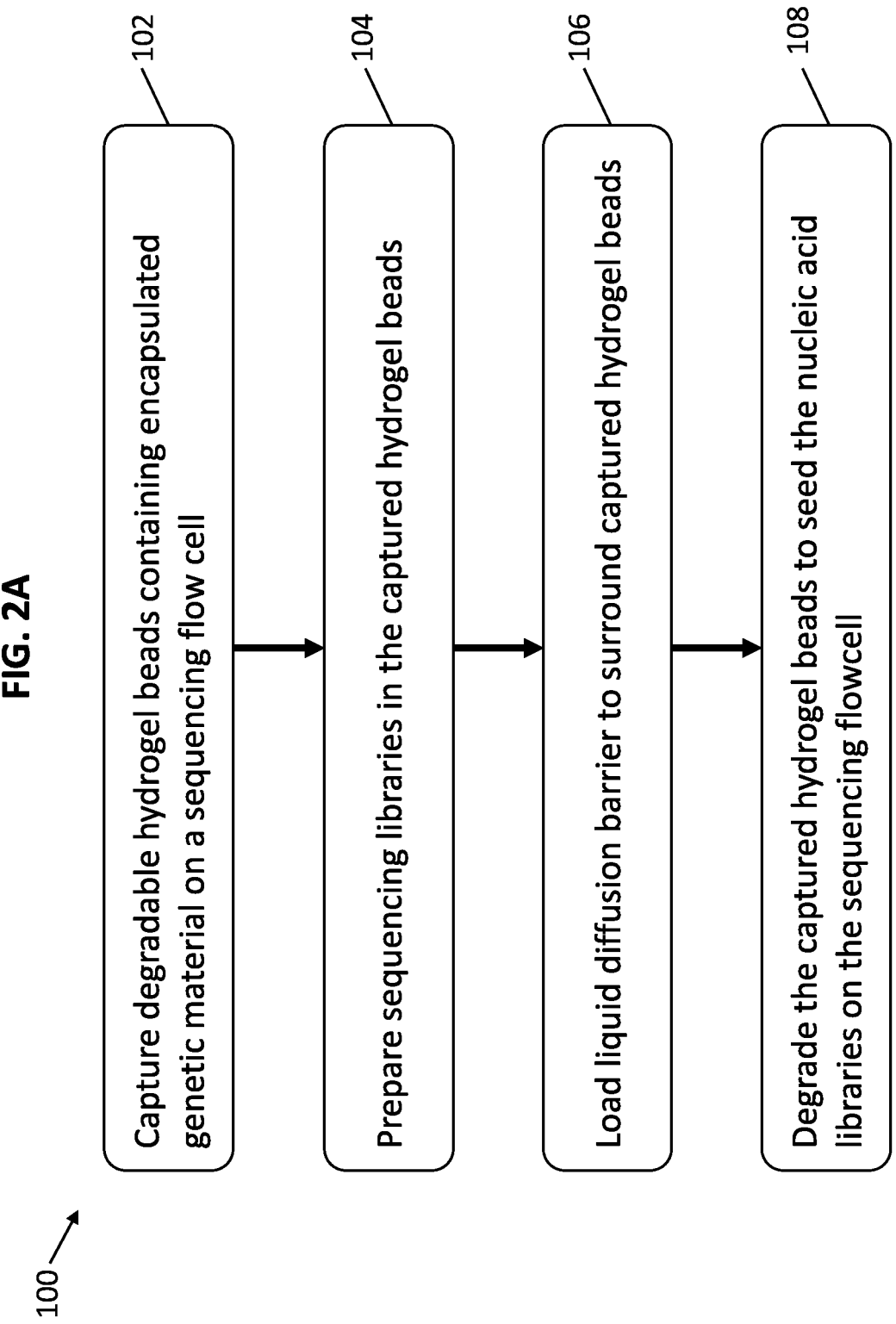

FIG. 2A illustrates an example method 100 for seeding sequencing libraries pertaining to a particular genetic material on a sequencing flow cell.

At step 102, degradable hydrogel beads containing encapsulated genetic material (for example, target nucleic acid molecules or cells containing target nucleic acid molecules) are captured on a sequencing flow cell. The beads are loaded onto the sequencing flow cell under conditions sufficient for capture of the hydrogel beads on the flow cell. Capture of the beads on the flow cell can be accomplished, for example, by physical constraint of the hydrogel beads on the flow cell, for example where the hydrogel beads have a diameter that is about 10% larger than the height of the flow cell.

At step 104, sequencing libraries are prepared from the genetic material in the captured hydrogel beads. In several examples, the hydrogel beads include pores that allow diffusion of reagents through the hydrogel bead while retaining the genetic material within the bead. Sequencing libraries are prepared from the genetic material in the captured hydrogel beads by flowing appropriate enzymes, reagents and components through the flow cell. The enzymes, reagents and components pass through the pores of the hydrogel beads for sequencing library preparation, whereas the genetic material (for example, target nucleic acid molecules) and the resulting sequencing libraries remain encapsulated within the hydrogel beads. As a result, individual hydrogel beads contain separate sequencing libraries produced from the encapsulated genetic material.

At step 106, a liquid diffusion barrier is loaded onto the sequencing flow cell to surround the hydrogel beads. The liquid diffusion barrier is a liquid in which the sequencing libraries encapsulated within the hydrogel beads have little to no solvation. Surrounding the captured hydrogel beads with the liquid diffusion barrier inhibits diffusion of the sequencing libraries outside of the bead volume when the bead is degraded in step 108.

At step 108, the hydrogel beads are degraded to allow transport of the sequencing libraries to the surface of the sequencing flow cell, by, for example, passive diffusion. The sequencing libraries bind to capture agents on the flow cell surface. The liquid diffusion barrier inhibits diffusion of the sequencing libraries beyond the diameter of the hydrogel beads. Thus, in the presence of the liquid diffusion barrier, seeding occurs in close proximity to the footprint of each hydrogel bead. In some examples, a cluster amplification reaction is performed to amplify the sequencing library on the flow cell surface prior to the sequencing step. The seeded nucleic acid molecules from a single bead group together as a cluster patch on the flow cell. Knowing that the nucleic acid molecules inside each cluster patch originate from a single hydrogel bead simplifies subsequent analysis of sequence reads and reconstruction of the target nucleic acid sequences originally encapsulated in the hydrogel bead.

FIG. 2B illustrates an example method 200 for seeding sequencing libraries pertaining to a particular genetic material (for example, target nucleic acid molecules) on a sequencing flow cell.

At step 202, degradable hydrogel beads containing encapsulated sequencing libraries prepared from genetic material (such as target nucleic acid molecules or cells containing target nucleic acid molecules) are captured on a sequencing flow cell. Prior to capture of the hydrogel beads on the sequencing flow cell, the beads are prepared to encapsulate the genetic material. The hydrogel beads include pores that allow diffusion of reagents through the hydrogel bead while retaining the genetic material within the bead. Sequencing libraries are prepared from the genetic material in the captured hydrogel beads by incubating the beads encapsulating the genetic material with appropriate enzymes, reagents and components to generate the sequencing libraries. The enzymes, reagents and components pass through the pores of the hydrogel beads for sequencing library preparation, whereas the genetic material and the resulting sequencing libraries remain encapsulated within the hydrogel beads. As a result, individual hydrogel beads contain separate sequencing libraries produced from the encapsulated genetic material. The degradable hydrogel beads containing the encapsulated sequencing libraries are then loaded onto the sequencing flow cell under conditions sufficient for capture of the hydrogel beads on the flow cell. Capture of the beads on the flow cell can be accomplished, for example, by physical constraint of the hydrogel beads on the flow cell, for example where the hydrogel beads have a diameter that is about 10% larger than the height of the flow cell.

At step 204, a liquid diffusion barrier is loaded onto the sequencing flow cell to surround the hydrogel beads. The liquid diffusion barrier is a liquid in which the sequencing libraries encapsulated within the hydrogel beads have little to no solvation. Surrounding the captured hydrogel beads with the liquid diffusion barrier inhibits diffusion of the sequencing libraries outside of the bead volume when the bead is degraded in step 206.

At step 206, the hydrogel beads are degraded to allow transport of the sequencing libraries to the surface of the sequencing flow cell, by, for example, passive diffusion. The sequencing libraries bind to capture agents on the flow cell surface. The liquid diffusion barrier inhibits diffusion of the sequencing libraries beyond the diameter of the hydrogel beads. Thus, in the presence of the liquid diffusion barrier, seeding occurs in close proximity to the footprint of each hydrogel bead. In some examples, a cluster amplification reaction is performed to amplify the sequencing library on the flow cell surface prior to the sequencing step. The seeded nucleic acid molecules from a single bead group together as a cluster patch on the flow cell. Knowing that the nucleic acid molecules inside each cluster patch originate from a single hydrogel bead simplifies subsequent analysis of sequence reads and reconstruction of the sequence of the genetic material (such as target nucleic acid molecules) originally encapsulated in the hydrogel bead.

In some examples, the seeded sequencing libraries are sequenced. Any appropriate sequencing technique can be used, such as SBS. Additional description of the disclosed method is provided below.

A. Degradable Hydrogel Beads Encapsulating Genetic Material

Implementations provided herein relate to degradable hydrogel beads encapsulating genetic material, such as target nucleic acid molecules, as well as cells and cell lysate containing target nucleic acid molecules. The beads may include hydrogel polymers and crosslinkers that are mixed in the presence of the genetic material, and which form hydrogel beads that encapsulate the genetic material. The hydrogel beads may include pores that allow diffusion of reagents through the hydrogel bead while retaining the genetic material within the bead, thereby allowing reactions to take place within the beads.

Non-limiting examples of target nucleic acid molecules that can be encapsulated within the hydrogel bead include DNA, such as genomic or cDNA; RNA, such as mRNA, sRNA or rRNA; or a hybrid of DNA and RNA.

Example biological samples from which genetic material (such as target nucleic acid molecules) can be obtained include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a dictyostelium discoideum; a fungi such as *Pneumocystis carinii, Takifugu rubripes*, yeast, *Saccharamoyces cerevisiae* or *Schizosaccharomyces pombe*; or a *Plasmodium falciparum*. Genetic material can also be obtained from a prokaryote such as a bacterium, *Escherichia coli*, staphylococci or *Mycoplasma pneumoniae*; an archae; a virus such as Hepatitis C virus or human immunodeficiency virus; or a viroid. Target nucleic acid molecules can be obtained from a homogeneous culture or population of the above organisms or alternatively from a collection of several different organisms, for example, in a community or ecosystem. Genetic material need not be obtained from natural sources and can instead be synthesized using known techniques.

In some examples, target nucleic acid molecules for encapsulation within the hydrogel beads can be obtained from the genetic material of single cells. For example, single cells can be encapsulated within the hydrogel beads and nucleic acid molecules (for example, genomic DNA) isolated from the single cells using an in-bead isolation assay.

In some examples, target nucleic acid molecules for encapsulation within the hydrogel beads can be obtained from cell lysate that is encapsulated within the hydrogel beads. Target nucleic acid molecules (for example, genomic DNA) are prepared in-bead from the lysate, and processed to generate sequencing libraries for use in the methods provided herein.

The genetic material encapsulated with the hydrogel bead is of sufficient size that it is entrapped within the hydrogel bead such that it cannot pass through the pores of the hydrogel bead. In some examples, the target nucleic acid molecule encapsulated within the hydrogel bead is at least about 100 nucleotides in length, at least about 150 nucleotides in length, at least about 200 nucleotides in length, at least about 300 nucleotides in length, at least about 500 nucleotides in length, at least about 1,000 nucleotides in length, at least about 5,000 nucleotides in length, at least about 10,000 nucleotides in length, at least about 20,000 nucleotides in length, at least about 50,000 nucleotides in length, at least about 100,000 nucleotides in length, or more nucleotides in length. In several examples, the nucleic acid molecules encapsulated within the hydrogel beads are genomic DNA fragments of from about 1,000 to about 10,000 nucleotides in length, from about 10,000 to about 20,000 nucleotides in length, from about 10,000 to about 50,000 nucleotides in length, from about 50,000 to about 100,000 nucleotides in length, or about 300, about 500, about 1000, about 10,000, about 20,000, about 50,000 or about 100,000 nucleotides in length, or a range between any two of the foregoing sizes, or a length longer than the foregoing sizes. In some examples, the encapsulated nucleic acid molecules are up to about 3 Mbases in length.

The hydrogel beads for use in the disclosed methods can have any diameter appropriate for the methods described herein. In some examples, the hydrogel beads have a diameter of about 2, about 3, about 4, about 5, about 10, about 15, about 20, about 30, about 40, about 50, about 60, about 70, about 80, about 90, about 100, about 110, about 120, about 130, about 140, or about 150 μm. In some examples, the hydrogel beads have a diameter of 2, 3, 4, 5, 10, 15, 20, 30, 40, 50, 60, 70, 80, 90, 100, 110, 120, 130, 140, or 150 μm, or a size within a range defined by any two of the aforementioned values. In some examples, the size of the beads is non-uniform, and thus, the size of the beads includes beads of various diameters.

The hydrogel beads may be prepared by cross-linking hydrophilic biopolymers or synthetic polymers under appropriate conditions. Thus, in some examples, the hydrogel bead may include a crosslinker. As used herein, the term "crosslinker" refers to a molecule that can form a three-dimensional network when reacted with the appropriate base monomers. Examples of the polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-meth)acrylate, PEO—PPO—PEO copolymers (Pluronics), poly(phosphazene), poly (methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis (acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations or mixtures thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO).

In some examples, a crosslinker forms a disulfide bond in the polymer of the hydrogel bead.

In some examples, the crosslinker is a reversible crosslinker. In some examples, a reversible crosslinker is capable of reversibly crosslinking the hydrogel polymer and is capable of being un-crosslinked in the presence of a cleaver. In some examples, a crosslinker can be cleaved by the presence of a reducing agent, by elevated temperature, or by an electric field. In some examples, the reversible crosslinker may be N,N'-bis(acryloyl)cystamine, a reversible crosslinker for polyacrylamide gels, wherein a disulfide linkage may be cleaved in the presence of a suitable reducing agent. Contacting the crosslinker with a reducing agent cleaves the disulfide bonds of the crosslinker, breaking down the hydrogel beads. The hydrogel beads degrade, and release the contents, such as DNA libraries retained therein. In some examples, the crosslinker is cleaved by increasing the temperature to greater than about 50, about 55, about 60, about 65, about 70, about 75, about 80, about 85, about 90, about 95, or about 100° C. In some examples, the crosslinker is cleaved by contacting the hydrogel beads with a reducing agent. In some examples, the reducing agents include phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or β-mercaptoethanol (BME), 2-mercaptoethanol or aminoethanethiol, glutathione, thioglycolate or thioglycolic acid, 2,3-dimercaptopropanol, tris(2-carboxyethyl)phosphine (TCEP), tris(hydroxymethyl)phosphine (THP), or P[tris(hydroxymethyl)phosphine] propionic acid (THPP), or a combination of two or more thereof. In some examples, the crosslinker may be N,N'-(1,2-Dihydroxyethylene)bisacrylamide, a reversible crosslinker for polyacrylamide gels, wherein a 1,2-diol linkage may be cleaved in the presence of an oxidation agent such as sodium periodate, and the amidomethylol linkage can be cleaved in the presence of a strong acid such as periodic acid, or a strong base such sodium hydroxide to degrade the bead. In some examples, the crosslinker is cleaved by increasing the temperature to greater than about 80, about 85, about 90, about 95, or about 100° C.

In some examples, the reagents including reagents for processing genetic material, such as reagents for isolating nucleic acids from a cell, for amplifying or sequencing nucleic acids, or for preparation of sequencing libraries. The reagents pass through the pores of the hydrogel beads, whereas the genetic material (such as target nucleic acid molecules) and sequencing libraries generated therefrom are retained within the hydrogel beads.

In some examples, crosslinking the polymers of the hydrogel bead forms a hydrogel matrix having pores (for example, a porous hydrogel matrix). These pores are capable of retaining sufficiently large genetic material within the hydrogel bead, but allow small materials, such as reagents, to pass through the pores, thereby passing in and out of the hydrogel beads. The hydrogels can have any pore size having a diameter sufficient to allow diffusion of reagents through the bead while retaining the encapsulated nucleic acid molecules. The term "pore size" can also refer to an average diameter or an average effective diameter of a cross-section of the pores, based on the measurements of a plurality of pores. The effective diameter of a cross-section that is not circular equals the diameter of a circular cross-section that has the same cross-sectional area as that of the non-circular cross-section. In some examples, the hydrogel bead can be swollen when the hydrogel is hydrated. The sizes of the pores can then change depending on the water content in the hydrogel of the hydrogel bead. In some examples, the pores have a diameter of from about 10 nm to about 100 nm.

In some examples, the pore size of the hydrogel beads is tuned by varying the ratio of the concentration of polymer to the concentration of crosslinker. In some examples, the ratio of polymer to crosslinker is about 30:1, about 25:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:15, about 1:20, or about 1:30, or about any one of these rations, or a ratio within a range defined by any two of the aforementioned ratios. In some examples, additional functions such as DNA primer, or charged chemical groups can be grafted to polymer matrix to meet the requirements of different applications.

Any appropriate method can be used to make the hydrogel beads containing the encapsulated nucleic acid molecules.

In some examples, the hydrogel beads are prepared by vortex assisted emulsion. As used herein, vortex assisted emulsion refers to vortexing of a hydrogel monomers or polymer with long nucleic acid molecules in a container, such as in a tube, vial, or reaction vessel. The components are mixed, for example by manual or mechanical vortexing or shaking.

In some examples, the beads are prepared by microfluidic flow techniques. Microfluidic flow includes use of a microfluidic device for assisted gel emulsion generation, such as shown in FIG. 2. In some implementations, the microfluidic device includes microchannels configured to produce a hydrogel bead of a desired size and configured to encapsulate a selected amount of genetic material (such as a single cell or a predetermined amount of target nucleic acid molecules) per bead. In addition to the size of the microfluidic device and the width of the channels, the flow rate of the aqueous channel and the immiscible fluid channel may also affect the size of the hydrogel beads. In some examples, the microfluidic device has a height of about 50, about 60, about 70, about 80, about 90, about 100, about 110, about 120, about 130, about 140, about 150, about 160, about 170, about 180, about 190, or about 200 µm, or a height within a range defined by any two of the aforementioned values. In some examples, the microfluidic device includes one or more channels. In some examples, the microfluidic device includes a channel for an aqueous stream and a channel for an immiscible fluid, such as an oil. In some examples, the width of the one or more channels is identical. In some examples, the width of the one or more channels is different. In some examples, the width of the one or more channels is about 40, about 45, about 50, about 55, about 60, about 65, about 70, about 75, about 80, about 85, about 90, about 95, about 100, about 105, about 110, about 115, about 120, about 125, about 130, about 135, about 140, about 145, or about 150 µm, or a width within a range defined by any two of the aforementioned values. In some examples, the width of the aqueous channel is about 75 µm. In some examples, the width of the immiscible fluid channel is about 78 µm. Other width values are possible as width can vary to finely tune the size of the bead. In addition to the size of the microfluidic device and the width of the channels, the flow rate of the aqueous channel and the immiscible fluid channel also affects the size of the hydrogel beads. In some examples, the flow rate of the solution in the aqueous phase channel is about 10, about 20, about 30, about 40, about 50, about 60, about 70, about 80, about 90, about 100, about 110, about 120, about 130, about 140, or about 150 µL/min, or a rate within a range defined by any two of the aforementioned values. In some examples, the flow rate of the immiscible fluid in the immiscible fluid channel is about 150, about 160, about 170, about 180, about 190, about 200, about 225, about 250, about 275, about 300, about 325, about 350, about 375, or about 400 µL/min, or a rate within a range defined by any two of the aforementioned values. In some examples, the solution in the aqueous phase includes a hydrogel polymer, a crosslinker, and genetic material, which flows through the aqueous channel into an immiscible fluid, such as a carrier oil at a flow rate less than the flow rate of the immiscible fluid, thereby forming droplets. In some examples, the hydrogel droplets containing genetic material are formulated in a uniform size distribution. In some examples, the size of the hydrogel beads is finely tuned by adjusting the size of the microfluidic device, the size of the one or more channels, or the flow rate of either or both of the aqueous solution or immiscible fluid. In some examples, the resulting hydrogel bead has a diameter ranging from about 2 to about 150 µm, for example, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, or about 150 µm, or a diameter within a range defined by any two of the aforementioned values.

In some examples, the size and uniformity of the hydrogel bead encapsulating genetic material can be further controlled by contacting hydrogel polymer prior to bead formation with a fluidic modifier, such as with an alcohol, including isopropyl alcohol. In the absence of isopropyl alcohol, beads form at a greater diameter than beads formed in the presence of isopropyl alcohol. Isopropyl alcohol influences the fluidic property of the hydrogel polymer, allowing modulation of the hydrogel beads.

Figure 9B:
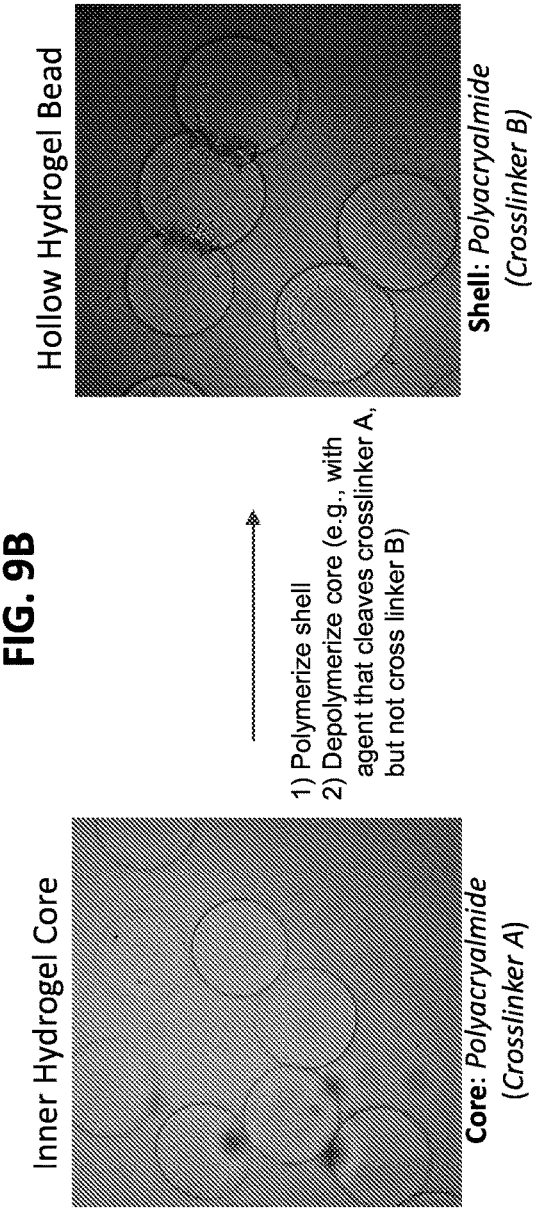
Figure 9C:
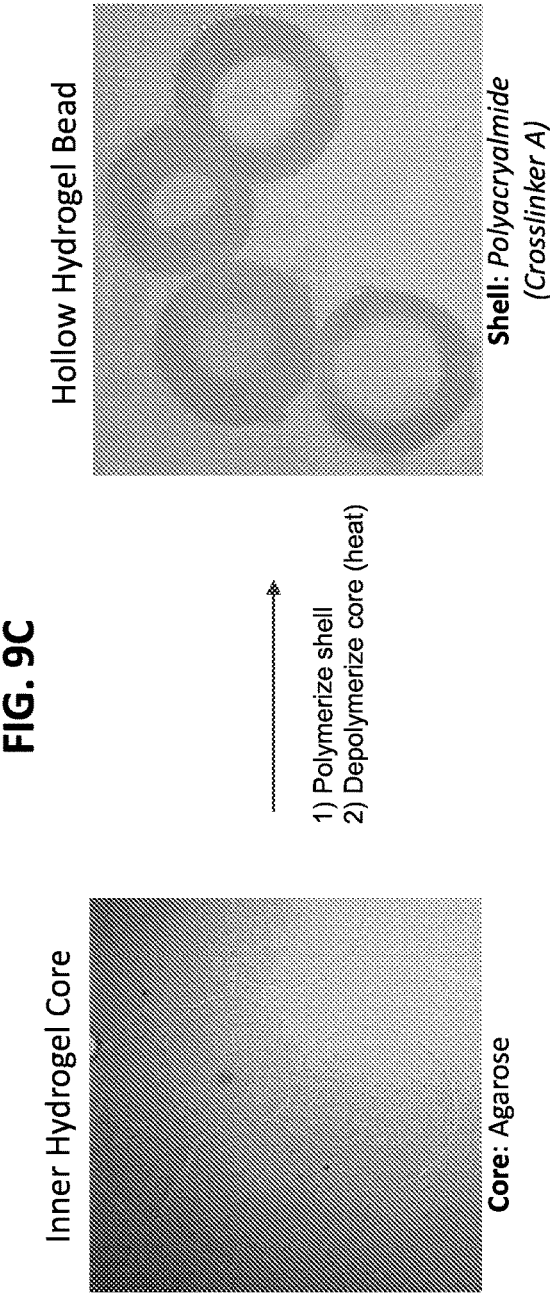

In another example, the hydrogel bead contains a hollow core and an outer shell, wherein the genetic material (such as target nucleic acid molecules) and/or the sequencing libraries are contained in the hollow core (see, e.g., FIGS. 9A-9C). The diameter of the hollow core is in the range of about 5% to about 75% of the hydrogel bead diameter. The hydrogel bead containing the hollow core and the outer shell can be made, for example, by encapsulating an inner hydrogel layer in an outer hydrogel layer, and subsequently selectively degrading the inner hydrogel layer, but not the outer hydrogel layer. The inner hydrogel layer is a hydrogel bead that contains the genetic material (such as target nucleic acid molecule) and/or sequencing libraries, for example, as described above. The inner hydrogel layer is depolymerized using a method that does not depolymerize the outer hydrogel layer to generate the hollow hydrogel bead. In an example, the inner layer is made of agarose and can be depolymerized by heating to 60° C. and the outer hydrogel layer is made of acrylamide with a chemically reversible cross-linker and is resistant to depolymerization at 60° C. In another example, both the inner and the outer layers are made of acrylamide, but orthogonal cross-linker chemistries are used for the two layers. For example, the inner layer cross-linker is cleaved by an oxidizing reagent such as sodium periodate and outer layer cross-linker is cleaved by a reducing reagent such as DTT. Depolymerization of the inner layer, but not the outer layer, produces the hydrogel bead with the hollow core and outer shell, where the genetic material and/or sequencing libraries are contained in the hollow core. The hollow inner core provides an aqueous medium for homogenous enzymatic and chemical reaction on the encapsulated nucleic acid.

In some examples, the amount of genetic material (such as target nucleic acid molecule) within a bead can be controlled by diluting or concentrating the genetic material within the inputted sample. The sample including the genetic material is mixed with hydrogel polymer, and the hydrogel polymer containing the genetic material is submitted to vortex assisted emulsion or microfluidic flow assisted emulsion, as described herein.

The hydrogel beads can include any amount of genetic material that is appropriate for the methods provided herein. For example, any suitable number of target nucleic acid molecules of any suitable length can be encapsulated in the hydrogel beads. In some examples, the encapsulated nucleic acid molecules are up to about 3 Mbases in length. In some examples, the hydrogel beads encapsulate an average of 1-1000 target nucleic acid molecules that are from about 1,000 to about 500,000 nucleotides in length. In some examples, the hydrogel beads encapsulate an average of 1-1000 target nucleic acid molecules that are from about 1,000 to about 100,000 nucleotides in length. In some examples, the hydrogel beads encapsulate an average of about 1-1000 target nucleic acid molecules that are from about 10,000 to about 150,000 nucleotides in length. In some examples, the hydrogel beads encapsulate an average of 1-1000 target nucleic acid molecules that are from about 50,000 to about 150,000 nucleotides in length. In some examples, the hydrogel beads encapsulate an average of about 1-1000 target nucleic acid molecules that are from about 10,000 to about 20,000 nucleotides in length. In some examples, the hydrogel beads encapsulate an average of about 1-100 target nucleic acid molecules that are from about 1,000 to about 500,000 nucleotides in length. In some examples, the hydrogel beads encapsulate an average of about 1-100 target nucleic acid molecules that are from about 1,000 to about 100,000 nucleotides in length. In some examples, the hydrogel beads encapsulate an average of about 1-100 target nucleic acid molecules that are from about 10,000 to about 150,000 nucleotides in length. In some examples, the hydrogel beads encapsulate an average of 1-100 target nucleic acid molecules that are from about 50,000 to about 150,000 nucleotides in length. In some examples, the hydrogel beads encapsulate an average of about 1-100 target nucleic acid molecules that are from about 10,000 to about 20,000 nucleotides in length. In some examples, the hydrogel beads encapsulate an average of about 10-100 target nucleic acid molecules that are from about 1,000 to about 500,000 nucleotides in length. In some examples, the hydrogel beads encapsulate an average of about 10-100 target nucleic acid molecules that are from about 1,000 to about 100,000 nucleotides in length. In some examples, the hydrogel beads encapsulate an average of about 10-100 target nucleic acid molecules that are from about 10,000 to about 150,000 nucleotides in length. In some examples, the hydrogel beads encapsulate an average of about 10-100 target nucleic acid molecules that are from about 50,000 to about 150,000 nucleotides in length. In some examples, the hydrogel beads encapsulate an average of about 10-100 target nucleic acid molecules that are from about 10,000 to about 20,000 nucleotides in length. In some examples, the hydrogel beads encapsulate an average of about 50-150 target nucleic acid molecules that are from about 1,000 to about 500,000 nucleotides in length. In some examples, the hydrogel beads encapsulate an average of about 50-150 target nucleic acid molecules that are from about 1,000 to about 100,000 nucleotides in length. In some examples, the hydrogel beads encapsulate an average of about 50-150 target nucleic acid molecules that are from about 10,000 to about 150,000 nucleotides in length. In some examples, the hydrogel beads encapsulate an average of about 50-150 target nucleic acid molecules that are from about 50,000 to about 150,000 nucleotides in length. In some examples, the hydrogel beads encapsulate an average of about 50-150 target nucleic acid molecules that are from about 10,000 to about 20,000 nucleotides in length.

In some examples, transposons are bound to the target nucleic acid molecule (e.g., genomic DNA), while keeping the target nucleic acid molecule intact, before encapsulating the target nucleic molecule into hydrogel beads. This can be accomplished, for example, by reacting the target nucleic acid molecule with Tn5 transposase in the absence of catalytic metal ion $Mg^{2+}$ (e.g., as described in the U.S. Patent Pub. 2015/0368638 of Gunderson et al., which is incorporated by reference herein in its entirety). After the pre-tagmented DNA is encapsulated in the hydrogel beads, they are captured on the flow cell surface and buffer containing $Mg^{2+}$ ions is flowed into the flow cell to complete the tagmentation process. This is followed by extension or gap-fill/ligation reaction to complete the addition of adapters to the DNA fragment to generate the sequencing library. The liquid diffusion barrier is then loaded onto the flow cell and the hydrogel beads are degraded to release the sequencing library in a spatially confined manner for seeding on the sequencing flow cell.

In another example, the target nucleic acid molecule (e.g., genomic DNA) is first tagmented outside the flow cell using tagmentation beads (e.g., 0.5-20 µm size) containing transposons on the bead surface (e.g., as described in the U.S. Patent Pub. 2014/0194324 of Gormley et al., which is incorporated by reference herein). The tagmented DNA is bound to the tagmentation beads after the tagmentation reaction. These beads are then encapsulated into larger hydrogel beads using a droplet generator for capture on a flow cell. Library preparation is continued on the flow cell by loading PCR mix containing P5/P7 primers to release the tagmented DNA from the tagmentation beads and to add adapters. In alternative examples, the tagmentation beads contain complete adapter sequences attached to the transposons which are attached to the tagmentation beads via hybridization and the library is released from tagmentation beads via denaturation. The liquid diffusion barrier is then loaded onto the flow cell and the hydrogel beads are degraded to release the sequencing library in a spatially confined manner for seeding on the sequencing flow cell.

B. Flow Cell Capture of Hydrogel Beads

Implementations provided herein include capture of hydrogel beads containing encapsulated genetic material on a sequencing flow cell. The hydrogel gel beads containing the encapsulated genetic material are loaded onto the sequencing flow cell under conditions sufficient for capture of the hydrogel beads on the sequencing flow cell.

Any appropriate approach can be used to capture the hydrogel beads on the flow cell surface. In some examples, the hydrogel beads are captured on the flow cell by physical constraint of the hydrogel beads on the flow cell due a size difference between the diameter of the hydrogel beads and the height of the flow cell. For example, wherein the diameter of the hydrogel beads is from about 5% to about 30% greater (such as about 5%, about 10%, about 15%, about 20%, about 25%, or about 30% greater) than the height of the flow cell to constrain the beads in the flow cell. In some examples, the diameter of the hydrogel beads is about 10% greater than the height of the flow cell to constrain the beads in the flow cell, for example, the diameter of the hydrogel beads is about 110 μm and the height of the flow cell is about 100 μm. This size difference causes the hydrogel beads to "stick" on the flow cell.

In some examples, the hydrogel beads are captured on the flow cell by the interaction of a capture agent on a surface of the flow cell with the hydrogel bead. Example capture agents for immobilizing a hydrogel bead on the surface of a flow cell in the disclosed methods include, without limitation, a capture nucleic acid that is complementary to at least a portion of a nucleic acid linked to the hydrogel or crosslinker of the bead, or a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

In some examples, the capture agent is a first member of a specific binding pair that is located on the sequencing flow cell, and binds to a second member of the specific binding pair located on the hydrogel bead. For example, the flow cell is functionalized with a first member of a specific binding pair and the hydrogel bead is functionalized with the second member of the specific binding pair.

In some examples, the capture agent is present at segregated locations on the flow cell. For example, in examples where the flow cell is a patterned flow cell containing an array of wells, the capture agent can be present at wells of the patterned flow cell.

Additionally, flow cells may contain bead trapping structures such as pillars/posts, weirs, cup-shaped structures, to immobilize/capture the beads in defined location within the flowcell. These trapping structures can be made by etching in glass or silicone, or by photolithography of photopatternable materials.

C. In-Bead Sequencing Library Preparation

In some examples, sequencing libraries can be prepared from the genetic material (such as target nucleic acid molecules) encapsulated within the hydrogel beads. The sequencing libraries can be prepared before, during, or after bead capture on the surface of the sequencing flow cell. In several examples, the sequencing libraries can be prepared from the genetic material encapsulated within the hydrogel beads when the beads are captured on the surface of the sequencing flow cell.

The genetic material (such as target nucleic acid molecules) encapsulated within a hydrogel bead are contacted with one or more reagents for preparation of the sequencing libraries. The sequencing libraries are retained within the hydrogel beads, and reagents are able to pass through the pores of the hydrogel beads. Thus, the hydrogel beads provide a microenvironment for controlled reactions of the encapsulated genetic material allowing a barrier for reagents to pass in and out of the hydrogel beads, while retaining the corresponding sequencing libraries within the beads. The entire sequencing library preparation process can be accomplished inside the hydrogel beads with multiple reagent exchanges through the porous hydrogel while retaining sequencing library products within the hydrogel matrix.

In several examples, preparing the sequencing libraries includes fragmenting the target nucleic acid molecules encapsulated within the hydrogel beads and adding adapters including universal nucleotide sequences to the fragments of the target nucleic acid molecules. Any appropriate method can be used to fragment the target nucleic acid molecules and add the adapters. Fragments of the target nucleic acid molecules that are linked to one or more adapters are referred to as "adapted fragments." The adapted fragments of the target nucleic acid molecules in each bead collectively provide a library of nucleic acids representing the target nucleic acid molecules from that bead that can be immobilized and then sequenced.

In several examples, the target nucleic acid molecules are subjected to a tagmentation procedure within the hydrogel beads for fragmentation and addition of adapters. In a non-limiting example, the tagmentation procedure is performed using Nextera™ (Illumina, San Diego, Calif.) tagmentation protocols and reagents. Tagmentation reactions combine random fragmentation and adapter ligation into a single step to increase the efficiency of the sequencing library preparation process. The result of the fragmenting is a population of fragments of the target nucleic acid molecules encapsulated in the hydrogel bead that include sequences from the parent target nucleic acid molecules of the hydrogel bead linked to one or more adapters. In several implementations, the fragments include at least one strand having the transposase index. The transposase enzyme is washed away, and additional sequences can be added to the ends of the adapted fragments, for example by PCR, ligation, or any other suitable methodology.

Some examples can include the use of a hyperactive Tn5 transposase and a Tn5-type transposase recognition site (see, e.g., Goryshin and Reznikoff, *J. Biol. Chem.*, 273:7367 (1998), which is incorporated by reference herein in its entirety), or MuA transposase and a Mu transposase recognition site comprising R1 and R2 end sequences (see, e.g., Mizuuchi, K., *Cell*, 35: 785, 1983 and Savilahti, H, et al, *EMBO J.*, 14: 4893, 1995, each of which is incorporated by reference herein in its entirety). Tn5 Mosaic End (ME) sequences can also be used.

More examples of transposition systems that can be used with certain examples of the methods provided herein include *Staphylococcus aureus* Tn552 (see, e.g., Colegio et al., *J. Bacteriol*, 183:2384-8, 2001 and Kirby et al., *Mol. Microbiol*, 43:173-86, 2002, each of which is incorporated by reference herein in its entirety), Ty1 (see, e.g., Devine & Boeke, *Nucleic Acids Res.*, 22:3765-72, 1994 and International Publication WO 95/23875, each of which is incorporated by reference herein in its entirety), Transposon Tn7 (see, e.g., Craig, *Science.* 271:1512, 1996, and Craig, Review in: *Curr Top Microbiol Immunol*, 204:27-48, 1996, each of which is incorporated by reference herein in its entirety), Tn/O and IS10 (see, e.g., Kleckner et al., *Curr Top Microbiol Immunol*, 204:49-82, 1996, which is incorporated by reference herein in its entirety), Mariner transposase (see, e.g., Lampe, et al., *EMBO J.*, 15: 5470-9, 1996, which is incorporated by reference herein in its entirety), Tel (see, e.g., Plasterk, *Curr. Topics Microbiol. Immunol*, 204:125-43, 1996, which is incorporated by reference herein in its entirety), P Element (see, e.g., Gloor, *Methods Mol. Biol,* 260:97-114, 2004, which is incorporated by reference herein in its entirety), Tn3 (see, e.g., Ichikawa & Ohtsubo, *J Biol. Chem.* 265:18829-32, 1990, which is incorporated by reference herein in its entirety), bacterial insertion sequences (see, e.g., Ohtsubo & Sekine, *Curr. Top. Microbiol. Immunol.,* 204:1-26, 1996, which is incorporated by reference herein in its entirety), retroviruses (see, e.g., Brown et al, *Proc Natl Acad Sci USA,* 86:2525-9, 1989, which is incorporated by reference herein in its entirety), and retrotransposon of yeast (see, e.g., Boeke & Corces, *Annu Rev Microbiol.* 43:403-34, 1989, which is incorporated by reference herein in its entirety). More examples include IS5, Tn10, Tn903, IS911, and engineered versions of transposase family enzymes (see, e.g., Zhang et al, *PLoS Genet.* 5:e1000689, 2009, and Wilson et al, *J. Microbiol. Methods* 71:332-5, 2007, each of which is incorporated by reference herein in its entirety).

Non-limiting examples of transposon sequences useful with the methods described herein are provided in U.S. Patent Application Pub. No. 2010/0120098, U.S. Patent Application Pub. No. 2012/0208705, U.S. Patent Application Pub. No. 2012/0208724 and Int. Patent Application Pub. No. WO 2012/061832 (each of which is incorporated by reference herein in its entirety). In some examples, a transposon sequence includes a first transposase recognition site, a second transposase recognition site, and an index sequence present between the two transposase recognition sites.

In some examples, the target nucleic acid molecules are fragmented using appropriate methods, and subsequently adapters are ligated to the fragments for sequencing library preparation. An example method includes dephosphorylating the 5' ends of fragments target nucleic acid molecules to prevent the formation of concatemers in subsequent ligation steps; ligating first adapters to the 3' ends of the dephosphorylated targets using a ligase, in which the 3' ends of the first adapters are blocked; re-phosphorylating of the 5' ends of the ligated targets; ligating a second adapter to the 5' ends of the dephosphorylated targets using the single stranded ligase, in which the 5' ends of the second adapters are non-phosphorylated.

Another example includes partial digestion of the fragments of the target nucleic acid molecules with a 5' exonuclease to form a double-stranded nucleic acid with single-stranded 3' overhangs. An adapter containing a 3' blocking group can be ligated to the 3' ends of double-stranded nucleic acid with 3' overhangs. The double-stranded nucleic acid with 3' overhangs with ligated adapters can be dehybridized to form single-stranded nucleic acids. An adapter containing a non-phosphorylated 5' end can be ligated to the 5' end of the single-stranded nucleic acid.

Methods to dephosphorylate nucleic acids, such as the 5' nucleotide of a nucleic acid include contacting a nucleic acid with a phosphatase. Examples of phosphatases include calf intestinal phosphatase, shrimp alkaline phosphatase, antarctic phosphatase, and APEX alkaline phosphatase (Epicentre).

Methods to ligate nucleic acids include contacting nucleic acids with a ligase. Examples of ligases include T4 RNA ligase 1, T4 RNA ligase 2, RtcB ligase, Methanobacterium RNA ligase, and TS2126 RNA ligase (Circligase™).

Methods to phosphorylate nucleic acids, such as the 5' nucleotide of a nucleic acid include contacting a nucleic acid with a kinase. Examples of kinases include T4 polynucleotide kinase.

In several implementations, the adapters that are linked to the fragments of the target nucleic acid molecules include sequences for subsequent seeding, sequencing, and analysis of sequence reads pertaining to the fragments of the target nucleic acid molecules. Adapters can include, for example, capture sequences, sequencing primer binding sites, amplification primer binding sites, and indexes.

In several examples, the adapters include universal nucleotide sequences for capture of the nucleic acid molecules of the sequencing library on the surface of a sequencing flow cell containing a lawn or wells having corresponding capture oligonucleotides that bind to the universal nucleotide sequence. The universal sequences present at ends of the fragments can be used for the binding of universal anchor sequences which can serve as primers and be extended in an amplification reaction. In several implementations, two different universal primers are used. One primer hybridizes with universal sequences at the 3' end of one strand of the indexed nucleic acid fragments, and a second primer hybridizes with universal sequences at the 3' end of the other strand of the indexed nucleic acid fragments. Thus, the anchor sequence of each primer can be different. Suitable primers can each include additional universal sequences, such as a universal capture sequence, and another index sequence. Because each primer can include an index, this step results in the addition of one or two index sequences, which can be the reverse complements of each other, or can have sequences that are not the reverse complements of each other.

The adapted fragments can be any appropriate size for subsequent seeding and sequencing steps. In some examples, the adapted fragments are from about 150 to about 400 nucleotides in length, such as from about 150 to about 300 nucleotides.

In some examples, the target nucleic acid molecules, or fragments or adapted fragments thereof may be amplified within the hydrogel beads according to any suitable amplification methodology.

In some examples, the amplification is isothermal amplification. Example isothermal amplification methods that can be used include, but are not limited to, multiple displacement amplification (MDA), which is a widely used technique for amplifying low quantities of DNA and is exemplified by, for example Dean et al., *Proc. Natl. Acad. Sci. USA* 99:5261-66 (2002) or isothermal strand displacement nucleic acid amplification exemplified by, for example U.S. Pat. No. 6,214,587, each of which is incorporated herein by reference in its entirety.

In additional examples, the amplification can include, but is not limited to, the PCR, SDA, TMA, and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify encapsulated nucleic acids. In some examples, primers directed specifically to the nucleic acid of interest are included in the amplification reaction.

In some examples, the amplification method can include ligation probe amplification or oligonucleotide ligation assay (OLA) reactions that contain primers directed specifically to the nucleic acid of interest. In some examples, the amplification method can include a primer extension-ligation reaction that contains primers directed specifically to the nucleic acid of interest, and which are capable of passing through the hydrogel pores. As a non-limiting example of primer extension and ligation primers that can be specifically designed to amplify a nucleic acid of interest, the amplification can include primers used for the GoldenGate assay (Illumina, Inc., San Diego, Calif.) as exemplified by U.S. Pat. Nos. 7,582,420 and 7,611,869, each of which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. *Nucleic Acids Res.* 21(5): 1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

In some examples, the adapted fragments encapsulated within the hydrogel beads can be further modified or reacted in preparation for seeding on the sequencing flow cell and sequencing. In some examples, the adapted fragments are reacted with a capture oligonucleotide having specificity for the adapted fragments (for example, by binding to an adapter sequence), and the capture oligonucleotides can be immobilized on a surface of a solid substrate. For instance, the capture oligonucleotide can include a first member of a universal binding pair, and wherein a second member of the binding pair is immobilized on a surface of a solid substrate.

D. Bead Degradation and Sequencing Library Seeding

The hydrogel beads are degraded while surrounded by a liquid diffusion barrier to release the sequencing libraries from the beads and seed the sequencing libraries on the sequencing flow cell. The liquid diffusion barrier is loaded onto the sequencing flow cell to fill the void volume between the hydrogel beads and to surround the hydrogel beads. Surrounding the captured hydrogel beads with the liquid diffusion barrier inhibits diffusion of the sequencing libraries outside of the bead volume when the bead is degraded. After bead degradation, the encapsulated sequencing libraries transport to the surface of the flow cell, where they are captured. Thus, in the presence of the liquid diffusion barrier, seeding on the flow cell occurs in close proximity to the footprint of each hydrogel bead.

An individual hydrogel bead contains a sequencing library produced from the target nucleic acid molecules within the bead. Accordingly, the sequencing library seeded from a single hydrogel bead corresponds to the target nucleic acid molecules that were encapsulated within that bead. Because seeding occurs in close proximity to the footprint on the flow cell of each hydrogel bead, the seeded sequencing library from each bead is spatially segregated (or "indexed") on the flow cell based on the location of the bead.

In some examples, the liquid diffusion barrier can be a hydrophobic liquid, such as oil, for example, mineral oil or Silicone oil, or perfluorinated oil, or a combination of two or more thereof. In other examples, the liquid diffusion barrier can be a viscous solution that impedes diffusion of DNA libraries such as buffers containing polymers such as polyethylene glycol (PEG), poly-vinyl-pyrrolidone, pluronic dextran, sucrose, and the like. In some examples, a temperature responsive material can be used as the liquid barrier. The temperature responsive material is a non-viscous liquid at non-seeding temperature, and can be easily loaded onto the flow cell and occupy the interstitial space between the hydrogel beads. Upon heating to seeding temperature, the material solidifies to form a physical barrier and prevent library diffusion. In some examples, the temperature responsive material can be a poly(N-isopropylacrylamide) or polyethylene oxide-polypropylene oxide-polyethylene oxide (PEO—PPO—PEO)/laponite nanoparticle composite material. In some examples, the liquid diffusion barrier used in the disclosed implementations is composed of a combination of any two or more of the liquid diffusion barriers discussed above.

The hydrogel beads can be degraded using any appropriate method that does not substantially reduce the effectiveness of the liquid diffusion barrier for inhibiting diffusion of the sequencing libraries beyond the diameter of the hydrogel beads. The hydrogel beads do not need to be completely degraded to release the sequencing libraries from the beads and seed the sequencing libraries on the sequencing flow cell. Sufficient degradation includes an increase in porosity of the hydrogel beads to allow for diffusion of the encapsulated sequencing libraries and transport of the sequencing libraries to the surface of the flow cell.

In some examples, the hydrogel beads are degraded by applying sufficient heat to the beads to disrupt the hydrogel matrix and allow diffusion of the sequencing libraries within the degraded hydrogel matrix and seeding of the sequencing library on the flow cell surface. In some examples, the heat can be applied to the hydrogel beads by heating the flow cell to about 90° C. for a sufficient about of time (such as 5 minutes) to degrade the hydrogel matrix.

In examples where the hydrogel matrix contains a reversible cross linker, the matrix can be degraded by un-crosslinking the matrix with an appropriate cleaver. For example, where the crosslinker contains disulfide bonds that crosslink polymers of the hydrogel, the cleaver can be a reducing agent, such as DTT. In some examples, the crosslinker contains 1,2-diol bond that can be cleaved by an oxidizing agent, a strong base, or a strong acid, such as sodium periodate and periodic acid. In some examples, the crosslinker contains a photo-cleavable moiety, the cleavage of which un-crosslinks the hydrogel matrix. In such examples, the hydrogel matrix can be exposed to light of an appropriate wavelength to cleave the photo-cleavable moiety and degrade the hydrogel matrix.

In another example, the reducing agent is activated by UV light. These photo-degradable reducing moieties can be present in the oil phase or can be introduced in the hydrogel bead via diffusion before the melting step.

After sufficient bead degradation, the encapsulated sequencing libraries transport to the surface of the flow cell, where they are captured. Any appropriate approach can be used to capture the sequencing libraries on the flow cell surface.

In some examples, the sequencing libraries are captured on the flow cell by the interaction of a capture agent on the flow cell with the adapted fragments of the sequencing libraries.

In some examples, the capture agent is a first member of a specific binding pair that is located on the sequencing flow cell, and binds to a second member of the specific binding pair located on the adapted fragments of the sequencing library. For example, the flow cell is functionalized with a first member of a specific binding pair and the adapters of the adapted fragments contain the second member of the specific binding pair.

In some examples, the capture agent, such as a capture oligonucleotide, can be attached to the surface of the sequencing flow cell. For example, the capture agent can be attached to wells on the surface of a patterned flow cell. The attachment can be via an intermediate structure such as a bead, particle, or gel. Attachment of capture agents to surface of a sequencing flow cell via a gel is exemplified by flow cells available commercially from Illumina Inc. (San Diego, Calif.) or described in WO 2008/093098, which is incorporated herein by reference in its entirety.

In particular examples, a patterned flow cell contains a surface for binding to sequencing libraries made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer and capture nucleic acids can be attached to gel material for capture and amplification of the sequencing libraries. The sequencing libraries can then be transported to the patterned surface such that individual adapted fragments in the libraries will seed individual wells via interactions with primers attached to the gel material; however, the adapted fragments will not occupy the interstitial regions between wells due to absence or inactivity of the gel material. Amplification of the adapted fragments will be confined to the wells since absence or inactivity of gel in the interstitial regions between wells prevents outward migration of the growing nucleic acid colony. The process can be conveniently manufactured, being scalable and utilizing conventional micro- or nano-fabrication methods.

In some examples, the seeded sequencing libraries may be amplified prior to sequencing. For example, the seeded sequencing libraries may be amplified using primer sites in the adapter sequences, and subsequently sequenced using sequencing primer sites in the adapter sequences.

In some examples, the seeded sequencing libraries are amplified by solid-phase amplification. Primers (such as capture primers) for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular example, the primer may include a sulphur-containing nucleophile, such as phosphorothioate or thiophosphate, at the 5' end. In the case of solid-supported polyacrylamide hydrogels, this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described in WO 05/065814, which is incorporated by reference herein in its entirety.

Although the disclosure encompasses solid-phase amplification methods in which only one amplification primer is immobilized (the other primer usually being present in free solution), in some examples it is preferred for the solid support to be provided with both the forward and the reverse primers immobilized. In practice, there will be a 'plurality' of identical forward primers and/or a 'plurality' of identical reverse primers immobilized on the solid support, since the amplification process uses an excess of primers to sustain amplification. References herein to forward and reverse primers are to be interpreted accordingly as encompassing a 'plurality' of such primers unless the context indicates otherwise. The surface of the sequencing flow cell can include a plurality of primers that are used to produce amplicons from a sequencing libraries seeded on the flow cell. In some examples, the primers can have a universal priming sequence that is complementary to a universal sequence that is present in an adapter sequence ligated to of each target nucleic acid. In particular examples, the plurality of primers can be attached to the amplification site. The primers can be attached to an amplification site as set forth above for capture nucleic acids.

In some examples, the seeded sequencing libraries can be amplified using cluster amplification methodologies as exemplified by the disclosures of U.S. Pat. Nos. 7,985,565 and 7,115,400, the contents of each of which are incorporated herein by reference in their entirety. The incorporated materials of U.S. Pat. Nos. 7,985,565 and 7,115,400 describe methods of nucleic acid amplification which allow amplification products to be immobilized on a solid support in order to form arrays comprised of clusters or "colonies" of immobilized nucleic acid molecules. Each cluster or colony on such an array is formed from a plurality of identical or substantially identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons.

It will be appreciated that a small amount of contamination can be present in a colony or cluster without negatively affecting a subsequent sequencing reaction. Example levels of contamination that can be acceptable at an individual amplification site for particular applications include, but are not limited to, at most 0.1%, 0.5%, 1%, 5%, 10% or 25% contaminating amplicons.

Other suitable methodologies can also be used to produce immobilized amplicons from immobilized DNA fragments produced according to the methods provided herein. For example one or more clusters or colonies can be formed via solid-phase PCR whether one or both primers of each pair of amplification primers are immobilized. In some examples, the encapsulated nucleic acids are amplified within the beads, and then deposited in an array or on a solid support in a cluster.

E. Sample Multiplexing

In some examples, sample indexing methods can be used to interrogate multiplex nucleic acid samples on a single sequencing flow cell. Any appropriate multiplexing approach can be used.

For example, in some examples, in order to generate linked-long-read information from multiple samples in the same flow cell lane, different indexed transposons are used to identify the hydrogel patches from each sample. For example, the target nucleic acid molecules can be tagmented prior to bead capture on the flow cell. Different nucleic acid samples (encapsulated in hydrogel beads as discussed herein) are separately tagmented using different indexed transposons and subsequently loaded on the flow cell for completing the sequencing library preparation and release of library from the hydrogel beads. This provides seeded patches containing different index sequences corresponding to different samples that can be separated from each other during post-sequencing read analysis.

Alternatively, the hydrogel beads from each sample are processed sequentially on the flow cell. The beads containing a first sample are loaded onto the flow cell and target nucleic acids are tagmented using indexed transposon. Once the library from first sample is released from the bead and seeded on to the flow cell, a second round of hydrogel beads containing a second target nucleic acid sample are loaded onto the flow cell and are tagmented using a distinct indexed transposon to generate a second indexed library which is released in spatially confined manner for seeding on the flow cell surface. This provides seeded patches containing different DNA index sequences corresponding to different samples that can be separated from each other during post-sequencing read analysis.

In an additional approach for sample multiplexing, exogenous nucleic acid molecules can be spiked into different target nucleic acid samples at the bead encapsulation step. The exogenous nucleic acid molecule can be, for example, double or single stranded DNA. Non-limiting examples of exogenous DNA that can be spiked into samples as a marker include Phi-X, λ1, λ3, or λ3 DNA. Multiple samples are processed into hydrogel beads separately (each different sample containing a distinct spiked-in exogenous marker), and the beads are then pooled for loading on the flow cell. After tagmentation and library preparation and seeding on the flow cell, each resulting cluster patch of seeded library contains clusters/reads from the spiked DNA sample, which can be used to identify sample origin during read analysis.

In some examples, in order to maximize utilization of the flow cell for sequencing data generation, an additional step can be added to the workflow following seeding of sequencing library from the hydrogel beads. At this stage, the interstitial space between the hydrogel bead footprints has a low density of seeded library. In order to utilize this interstitial space, an additional seeding step can be performed using a regular short read library from the same or different sample and library seeds in the empty regions in the interstitial spaces and within the hydrogel patch. This short read library contains a different DNA index to separate the reads from the linked-long read and short read libraries.

F. Sequencing

In some examples, the seeded sequencing libraries are sequenced in full or in part. The seeded sequencing libraries can be sequenced according to any suitable sequencing methodology, such as direct sequencing, including SBS, sequencing by ligation, sequencing by hybridization, nanopore sequencing and the like. Non-limiting examples of methods for determining the sequence of immobilized nucleic acid fragments are described, for instance, in Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502), each of which is incorporated by reference herein in its entirety.

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Implementations in which images are obtained in different color channels, for example, coinciding with different labels used to distinguish one nucleotide base type from another are particularly applicable. In some examples, the process to determine the nucleotide sequence of a fragment can be an automated process.

One sequencing methodology is SBS. In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS Implementation, fluorescently labeled nucleotides are added to a primer (thereby extending the primer) in a template dependent fashion such that detection of the order and type of nucleotides added to the primer can be used to determine the sequence of the template.

In one example, a nucleotide monomer includes locked nucleic acids (LNAs) or bridged nucleic acids (BNAs). The use of LNAs or BNAs in a nucleotide monomer increases hybridization strength between a nucleotide monomer and a sequencing primer sequence present on an immobilized fragment.

SBS can use nucleotide monomers that have a terminator moiety or those that lack any terminator moieties. Methods using nucleotide monomers lacking terminators include, for example, pyrosequencing and sequencing using γ-phosphate-labeled nucleotides, as set forth in further detail herein. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxy nucleotides, or the terminator can be reversible as is the case for sequencing methods developed by Solexa (now Illumina, Inc.).

SBS techniques can use nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In Implementations where two or more different nucleotides are present in a sequencing reagent, the different nucleotides can be distinguishable from each other, or alternatively the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Some examples include pyrosequencing techniques. Pyrosequencing detects the release of inorganic pyrophosphate (PPi) as particular nucleotides are incorporated into the nascent strand (Ronaghi et al., *Analytical Biochemistry*, 242(1):84-9, 1996, Ronaghi, *Genome Res.*, 11(1):3-11, 2001, Ronaghi, Uhlen, and Nyren, *Science*, 281(5375), 363, 1998, and U.S. Pat. Nos. 6,210,891; 6,258,568 and 6,274,320, each of which is incorporated by reference herein in its entirety). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another example type of SBS, cycle sequencing is accomplished by stepwise addition of reversible terminator nucleotides containing, for example, a cleavable or photobleachable dye label as described, for example, in WO 04/018497, WO 91/06678, WO 07/123,744, and U.S. Pat. No. 7,057,026, each of which is incorporated by reference herein in its entirety. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In some reversible terminator-based sequencing implementations, the labels do not substantially inhibit extension under SBS reaction conditions. However, the detection labels can be removable, for example, by cleavage or degradation. Images can be captured following incorporation of labels into arrayed nucleic acid features. In particular examples, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such examples, each image will show nucleic acid features that have incorporated nucleotides of a particular type. Different features will be present or absent in the different images due to the different sequence content of each feature. However, the relative position of the features will remain unchanged in the images. Images obtained from such reversible terminator-SB S methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth herein.

In particular examples some or all of the nucleotide monomers can include reversible terminators. In such examples, reversible terminators/cleavable fluorophores can include fluorophores linked to the ribose moiety via a 3' ester linkage (see, e.g., Metzker, *Genome Res.*, 15:1767-1776, 2005, which is incorporated by reference herein in its entirety). Other approaches have separated the terminator chemistry from the cleavage of the fluorescence label (see, e.g., Ruparel et al., *Proc Natl Acad Sci USA* 102: 5932-7, 2005, which is incorporated by reference herein in its entirety). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorophore and effectively reverses the termination. Examples of modified nucleotides are also described in U.S. Pat. Nos. 7,427,673, and 7,057,026, each of which is incorporated by reference herein in its entirety.

Additional example SBS systems and methods which can be utilized with the methods and systems described herein are described in U.S. Pub. Nos. 2007/0166705, 2006/0188901, 2006/0240439, 2006/0281109, 2012/0270305, and 2013/0260372, U.S. Pat. No. 7,057,026, PCT Publication No. WO 05/065814, U.S. Patent Application Publication No. 2005/0100900, and PCT Publication Nos. WO 06/064199 and WO 07/010,251, each of which is incorporated by reference herein in its entirety.

Some examples use detection of four different nucleotides using fewer than four different labels. For example, SBS can be performed using methods and systems described in U.S. Pub. No. 2013/0079232, which is incorporated by reference herein in its entirety. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three example configurations are not considered mutually exclusive and can be used in various combinations. An example that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some examples can use sequencing by ligation techniques. Such techniques use DNA ligase to incorporate oligonucleotides and identify the incorporation of such oligonucleotides. In several implementations, the oligonucleotides have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Example SBS systems and methods which can be utilized with the methods and systems described herein are described in U.S. Pat. Nos. 6,969,488, 6, 172,218, and 6,306,597.

Some examples can use nanopore sequencing (see, e.g., Deamer & Akeson, "Nanopores and nucleic acids: prospects for ultrarapid sequencing," *Trends Biotechnol.*, 18, 147-151, 2000, Deamer and Branton, "Characterization of nucleic acids by nanopore analysis", *Acc. Chem. Res.*, 35:817-825, 2002, Li, Gershow, Stein, Brandin, and Golovchenko, "DNA molecules and configurations in a solid-state nanopore microscope," *Nat. Mater.*, 2:611-615, 2003, each of which is incorporated by reference herein in its entirety). In such examples, the fragment passes through a nanopore. The nanopore can be a synthetic pore or biological membrane protein, such as a-hemolysin. As the fragment passes through the nanopore, each base-pair can be identified by measuring fluctuations in the electrical conductance of the pore (see, e.g., U.S. Pat. No. 7,001,792, Soni & Meller, "A. Progress toward ultrafast DNA sequencing using solid-state nanopores," *Clin. Chem.* 53, 1996-2001, 2007, Healy, "Nanopore-based single-molecule DNA analysis," *Nanomed.*, 2, 459-481, 2007, Cockroft, Chu, Amorin, and Ghadiri, "A single-molecule nanopore device detects DNA polymerase activity with single-nucleotide resolution," *J. Am. Chem. Soc.*, 130, 818-820, 2008, each of which is incorporated by reference herein in its entirety). Data obtained from nanopore sequencing can be stored, processed and analyzed as set forth herein. In particular, the data can be treated as an image in accordance with the example treatment of optical images and other images that is set forth herein.

Some examples can use methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated by reference herein in its entirety), or nucleotide incorporations can be detected with zero-mode waveguides as described, for example, in U.S. Pat. No. 7,315,019 (which is incorporated by reference herein in its entirety), and using fluorescent nucleotide analogs and engineered polymerases as described, for example, in U.S. Pat. No. 7,405,281 and U.S. Pub. No. 2008/0108082 (each of which is incorporated by reference herein in its entirety). The illumination can be restricted to a zeptoliter-scale volume around a surface-tethered polymerase such that incorporation of fluorescently labeled nucleotides can be observed with low background (see, e.g., Levene et al., *Science*, 299, 682-686, 2003, Lundquist et al., *Opt. Lett.*, 33:1026-1028, 2008, Korlach et al., *Proc. Natl. Acad. Sci. USA*, 105:1176-1181, 2008, each of which is incorporated by reference herein in its entirety). Images obtained from such methods can be stored, processed and analyzed as set forth herein.

Some SBS examples include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Pub. Nos. 2009/0026082; 2009/0127589; 2010/0137143; and 2010/0282617, each of which is incorporated by reference herein in its entirety. Methods set forth herein for amplifying target nucleic acids using kinetic exclusion can be readily applied to substrates used for detecting protons. More specifically, methods set forth herein can be used to produce clonal populations of amplicons that are used to detect protons.

G. Data Analysis

Any appropriate bioinformatics workflow can be used to analyze and process the sequence reads obtained using the disclosed methods.

In some examples, reads originating from the same long DNA fragment are labeled with the same barcode to enable linked-read analysis. Since clusters pertaining to the same DNA fragment are spatially co-located on the flow cell, falling within the boundary of the bead that contained the fragment, accurate barcode assignment can be based on the identification of the bead locations (or "cluster patches") on the flow cell. Bead location identification can be accomplished using real-time analysis (RTA) images directly (e.g., available on the Illumina MiSeq™ platform) and/or using the cluster coordinates reported by RTA. Thus, this workflow can be used, for example, on platforms supporting interrogation of cluster coordinates.

In some examples, given RTA (x,y) read coordinates on each tile (considering both surfaces and all tile swaths when appropriate), density-based spatial clustering can be performed to identify the bead locations on each tile, where each bead is assumed to correspond to a high-density cluster of reads compared to the lower-density background created by the reads that leaked into the interstitial space. The clustering procedure detects an unknown number of clusters (since the number of beads on each tile is not fixed), handles variable cluster shapes and sizes (in the event that the beads are not in a consistent size and a circular shape post-melting), and categorizes interstitial reads as noise. Any appropriate density-based clustering algorithms can be used to define clusters, for example the DBSCAN clustering algorithm. In several implementations, the bead boundary is computed from each resulting cluster by finding the convex hull of the points assigned to the cluster. To enhance the clustering results, a density-based read filtering procedure may be applied prior to clustering, which eliminates reads based on the sparsity of their neighborhood on the tile (for example, a read is filtered out if there are fewer than n other reads within a radius r around it on the tile, where n and r are configurable parameters). In some examples, a manual curation step to assess and correct the final results of the clustering procedure may be implemented.

In additional examples, bead location is determined from RTA coordinates using deep learning. For example, the U-Net convolutional neural network architecture for image segmentation or an appropriate CNN model can be used to determine cluster patch boundaries and corresponding bead location. In some such examples, the training dataset includes manually annotated images obtained from coordinate-based plots, as well as synthetically generated images. Synthetic data augmentation is achieved by applying a set of transformations to the manually annotated images; the transformations include shape deformations, size, number, and placement variations, as well as, inter- and intra-bead density variation.

When sequencing DNA from a known reference genome, genome alignment information can be used to further refine bead identification, rescue interstitial reads and improve the resulting barcode assignment. For example, beads assigned to the same cluster can be further separated by considering genome windows to which their reads mapped, along with their spatial proximity. Alternatively, inter-bead cross-talk can be quantified by counting reads that map to the same genome window in neighboring beads; bead pairs with significantly high cross-talk can then be merged to improve island contiguity and performance in several target applications, such as phasing. Probabilistic or "soft" barcode assignment is also considered for further performance improvement in several target applications, such as phasing and assembly.

In some examples, post-identification, each detected bead is associated with a unique barcode and the reads contained within the bead boundary are labeled with this barcode. As a result, reads that originate from the long DNA fragments initially trapped in the same bead are assigned to the same barcode and can be linked during subsequent analysis. In particular, for human genome phasing, barcoded reads can be linked into islands (corresponding to longer DNA fragments from which the reads originated) using the proximity in their genome alignment positions (e.g., reads in the same barcode can be linked if they map close by on the human genome), enabling the reconstruction of much larger phase blocks. In genome assembly, barcoding information can be used to disambiguate repeats and significantly increase the assembly contiguity, e.g. by first mapping reads to the partially assembled contigs and then using the barcoding information to link the contigs. Phasing and assembly pipelines have been implemented as subsequent steps of the data analysis workflow following the best practices for linked-read analysis and applying hydrogel-specific performance optimizations when appropriate.

III. Flow Cell Device and Use Thereof

In some implementations, the present disclosure relates to devices, systems, and methods for preparing nucleic acid libraries on a flow cell device. For example, the flow cell device may include a hydrogel that includes genetic material, wherein the hydrogel may be configured to retain the genetic material, while allowing reagents, enzymes, chemicals, and smaller sized primers of less than about 50 base pairs to pass through the hydrogel. The flow cell device may be used to prepare a nucleic acid library within the flow cell device and for sequencing genetic material retained within the hydrogel, including single cell sequencing.

In some examples the devices, systems, and methods eliminate complex single cell capture and library preparation methods by using a flow cell surface to capture and in situ convert the genomic content of individual cells to a sequencing library. The reads from the library can be mapped back to the original cells due to the spatial proximity of the clusters. In contrast to other flow cell library prep methods, examples provided herein begin with capture of individual single cells on a flow cell surface rather than long DNA molecules from cells with P5/P7 adapters added to the ends. Accordingly, examples provided herein reduce the complexities of DNA extraction, size-selection, and sequencing library preparation for long genomic fragments. Some examples of the devices, systems, and method also enables synthetic long read assembly using long DNA molecules (from 10 s to 100 s of kilobases) as input without any need for adapter ligation.

A. Hydrogel Flow Cell Device

Some examples relate to a flow cell device having a hydrogel material deposited thereon. In some examples, the hydrogel includes genetic material disposed therein. In some examples, the hydrogel includes pores that allow diffusion of reagents, enzymes, chemicals, and oligonucleotides or primers of less than about 50 base pairs through the pores, while retaining the genetic material therein.

In some examples, the flow cell device has a channel height of 50 µm, 60 µm, 70 µm, 80 µm, 90 µm, 100 µm, 110 µm, 120 µm, 130 µm, 140 µm, or 150 µm, or an amount within a range defined by any two of the aforementioned values.

The terms "solid surface," "solid support" and other grammatical equivalents herein refer to any material that is appropriate for or can be modified to be appropriate for the attachment of materials for the processing of nucleic acids, including, for example, materials for nucleic acid library preparation, including transposome complexes. As will be appreciated by those in the art, the number of possible solid support materials is very large. Possible materials include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful solid supports and solid surfaces for some examples are located within a flow cell apparatus.

In some examples, a solid support includes silica-based substrates, such as glass, fused silica, or other silica-containing materials. In some examples, silica-based substrates can also be silicon, silicon dioxide, silicon nitride, or silicone hydrides. In some examples, a solid support includes plastic materials such as polyethylene, polystyrene, poly(vinyl chloride), polypropylene, nylons, polyesters, polycarbonates, cyclic olefin polymers, or poly(methyl methacrylate). In some examples, the solid support is a silica-based material or plastic material. In some examples, the solid support has at least one surface comprising glass.

In some examples, the solid support can be, or can contain, a metal. In some such examples, the metal is gold. In some examples, the solid support has at least one surface including a metal oxide. In one example, the solid support includes a tantalum oxide or tin oxide.

Acrylamide, enone, or acrylate may also be utilized as a solid support material. Other solid support materials can include, but are not limited to gallium arsenide, indium phosphide, aluminum, ceramics, polyimide, quartz, resins, polymers and copolymers. The foregoing lists are intended to be illustrative of, but not limiting to the present application.

In some examples, the solid support and/or the solid surface can be quartz. In some examples, the solid support and/or the solid surface can be a semiconductor, such as GaAs or indium tin oxide (ITO).

Solid supports can include a single material or a plurality of different materials. Solid supports can be composites or laminates. Solid supports can be flat, round, textured and patterned. Patterns can be formed, for example, by metal pads that form features on non-metallic surfaces, for example, as described in U.S. Pat. No. 8,778,849, which is incorporated herein by reference. Another useful patterned surface is one having well features formed on a surface, for example, as described in U.S. Pat. App. Pub. No. 2014/0243224 A1, U.S. Pat. App. Pub. No. 2011/0172118 A1 or U.S. Pat. No. 7,622,294, each of which is incorporated herein by reference in its entirety. For examples that use a patterned surface, a gel can be associated with or deposited on the pattern features or alternatively the gel can be uniformly deposited across both the pattern features and the interstitial regions.

In some examples, the solid support comprises a patterned surface. A "patterned surface" refers to an arrangement of different regions in or on an exposed layer of a solid support. In some examples, the pattern can be an x-y format of features that are in rows and columns. In some examples, the pattern can be a repeating arrangement of features and/or interstitial regions. In some examples, the pattern can be a random arrangement of features and/or interstitial regions. Exemplary patterned surfaces that can be used in the methods and compositions set forth herein are described in U.S. Ser. No. 13/661,524 or US Pat. App. Publ. No. 2012/0316086 A1, each of which is incorporated herein by reference. Example patterned surfaces that can be used in the methods and compositions set forth herein are described in U.S. Ser. No. 13/661,524 or US Pat. App. Publ. No. 2012/0316086 A1, each of which is incorporated herein by reference.

In some examples, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate. In some examples, the array of wells or depressions are from about 10 μm to about 50 μm in diameter, such as about 10 μm, about 15 μm, about 20 μm, about 25 μm, about 30 μm, about 35 μm, about 40 μm, about 45 μm, or about 50 μm in diameter, or a diameter within a range defined by any two of the aforementioned values. In some examples, the wells or depressions have a depth of about 0.5 μm to about 1 nm, such as about 0.5 μm, about 0.6 μm, about 0.7 μm, about 0.8 μm, about 0.9 μm, or about 1 μm in depth, or a depth within a range defined by any two of the aforementioned values. In some examples, the wells or depressions are made of a hydrophobic material. In some examples, the hydrophobic material includes an amorphous fluoropolymer, including for example, CYTOP, Fluoropel®, or Teflon®. See, e.g., PCT App. No. PCT/US2017/033169, which is incorporated herein by reference in its entirety.

In some examples, a solid support described herein forms at least part of a flow cell or is located in a flow cell. In one example, a solid support in the flow cell device is coated with a surface polymer comprising functional groups capable of forming covalent bonds with oligonucleotides or modified oligonucleotides, such as those described in PCT Publ. Nos. WO 2013/184796 or WO2016/066586. In some examples, the surface polymer comprises a recurring unit of Formula (I) and a recurring unit of Formula (II):

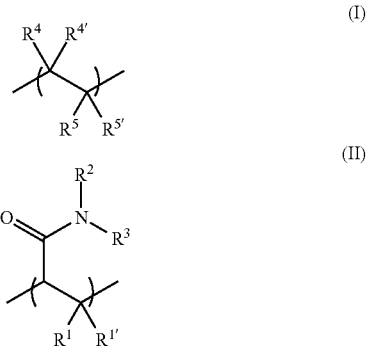

wherein $R^1$ and $R^{1'}$ are each independently hydrogen, halo, alkyl, alkoxy, alkenyl, cycloalkyl, aryl, heteroaryl, heterocyclyl, or an optionally substituted variant thereof;

$R^2$ and $R^3$ are each independently hydrogen, alkyl, alkylamino, alkylamido, alkylthio, aryl, or an optionally substituted variant thereof;

$R^4$, $R^{4'}$, $R^5$, and $R^{5'}$ are each independently hydrogen, $R^6$, $OR^6$, $-C(O)OR^6$, $-C(O) R^6$, $-OC(O) R^6$, $-C(O)NR^7R^8$, or $-NR^7R^8$;

wherein $R^6$ is hydrogen, hydroxyl, alkyl, cycloalkyl, hydroxyalkyl, aryl, heteroaryl, heterocyclyl, or an optionally substituted variant thereof; and $R^7$ and $R^8$ are each independently hydrogen or alkyl, or $R^7$ and $R^8$ taken together with the atom or atoms to which they are attached form a heterocycle.

In some examples, R', $R^{1'}$, $R^3$, $R^5$, and $R^{5'}$ are each hydrogen. In some examples, $R^{4'}$ is hydrogen or alkyl. In some examples, $R^4$ is $-C(O)NR^7R^8$. In some examples, $R^2$ is $-(CH2)5-NHC(O)CH_2N_3$. In some examples, the surface polymer is poly(N-(5-azidoacetamidylpentyl)acrylamide-co-acrylamide) (PAZAM) or silane free acrylamide (SFA). In some examples, the surface polymer is covalently bound to the solid support. In other examples, the surface polymer is non-covalently bound to the solid support. In this example, the flow cell device includes a solid support having a surface polymer coating, upon which a hydrogel including genetic material may be flowed.

As used herein, the term "alkyl" refers to a fully saturated, straight or branched, hydrocarbon chain. In some examples, the alkyl group contains from 1 to 20 carbon atoms, or from 1 to 6 carbon atoms, or from 1 to 4 carbon atoms. A "lower alkyl" has 1 to 4 carbon atoms and may be designated as $C_{1-4}$ alkyl. Exemple 1 to 6 carbon alkyl groups are methyl, ethyl, propyl, isopropyl, butyl, isobutyl, sec-butyl, tert-butyl, pentyl, isopentyl, or hexyl.

As used herein, the term "alkenyl" refers to an alkyl group that contains one or more double bonds.

As used herein, the term "cycloalkyl" refers to a completely saturated, mono- or polycyclic ring system. When multiple rings are present, they may be fused, bridged, or spirocyclic systems. Cycloalkyls may contain from 3 to 10 carbon ring atoms, or from 3 to 8 carbon ring atoms, or from 3 to 6 carbon ring atoms. Examples include cyclopropyl, cyclobutyl, cyclopentyl, cyclohexyl, cycloheptyl, and cyclooctyl.

As used herein, the term "aryl" refers to a carbocyclic, mono- or polycyclic aromatic ring system. Aryl rings may include fused non-aromatic rings. In some examples, the aryl group has 6, 10, or 14 carbon ring atoms. Exemple aryl groups are benzene, naphthalene, and anthracene.

The terms "heterocyclyl" and "heterocycle" refer to a ring system that includes at least one heteroatom, such as oxygen, nitrogen, or sulfur. Such systems can be unsaturated, partially saturated, aromatic, or a combination thereof.

As used herein, "heteroaryl" refers to a monocyclic or polycyclic aromatic ring system containing one or more heteroatoms, such as nitrogen, oxygen, or sulfur. "Heteroaryl" groups include fused systems comprising at least one aromatic, heteroatom-containing ring, while another ring may be carbocyclic or heterocyclic, and aromatic or not aromatic. Exemple heteroaryl groups include furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine.

As used herein, "alkylamino" refers to an alkyl group in which one or more of the hydrogen atoms are replaced by an amino group. Exemple alkylamino groups include but are not limited to aminomethyl, 2-aminoethyl, 3-aminoethyl.

As used herein, "alkylamido" refers to an alkyl group in which one or more of the hydrogen atoms are replaced by a C-amido group or an N-amido group.

The term "halo" refers to fluorine, chlorine, bromine, and iodine substituents, namely, fluoro, chloro, bromo, and iodo.

Whenever a group is described as being "optionally substituted" that group may be unsubstituted or substituted with one or more of the indicated substituents.

Some examples provided herein therefore relate to a hydrogel flow cell device. As used herein, a hydrogel flow cell device is a flow cell device having a solid support as described herein, and further including a hydrogel, wherein the hydrogel includes a hydrogel polymer and genetic material.

Hydrogels may be prepared by cross-linking hydrophilic biopolymers or synthetic polymers. Thus, in some examples, the hydrogel may include a crosslinker. Examples of the hydrogel polymers for the hydrogel flow cell device, which may include one or more crosslinkers, include but are not limited to, those described above for hydrogel beads.

Figure 10A:
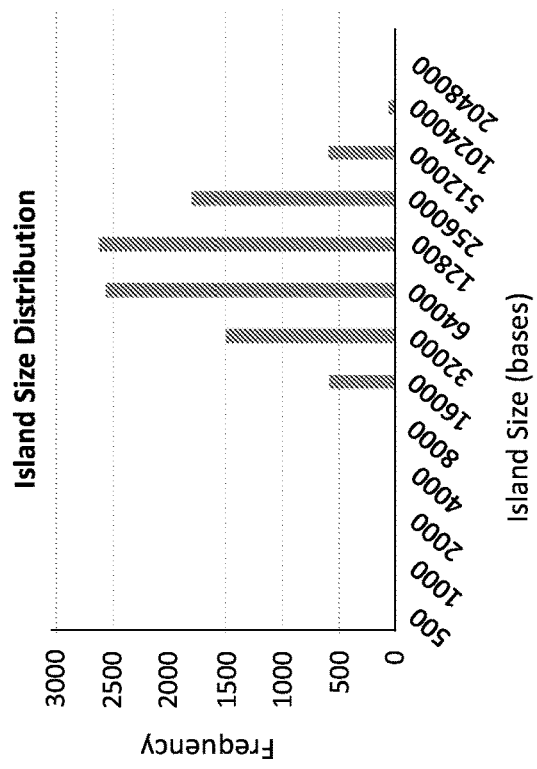
FIGS. 10A-10C show a schematic diagram (FIG. 10A), a graph of island size distribution (FIG. 10B), and an island diagram (FIG. 10C) for an example workflow using cell lysate input to generate hydrogel beads containing genetic material.

In some examples, the crosslinker is a reversible crosslinker, for example, as described above for hydrogel beads. In some examples, the hydrogel layer is a reversible hydrogel layer that can be crosslinked or uncrosslinked depending on the chemical that it is exposed to. In some examples, the reversible hydrogel layer is prepared with crosslinkers, such as bisacrylamide crosslinkers, containing disulfide bonds, which can be broken with reducing agents such as DTT, TCEP, or THP (phosphine). As shown in FIG. 17, 10-100 micron-size reversible hydrogel polymer encapsulating a load of dye-stained bacteria (top images) are degradable upon exposure to the reducing agent THP, resulting in the release of the bacteria (bottom images).

In some examples, elevating the temperature or contacting with a reducing agent degrades the crosslinker, thereby releasing encapsulated genetic material from the hydrogel polymer.

In some examples, the crosslinking of the crosslinker establishes pores within the hydrogel polymer, for example, as described above for hydrogel beads. In some examples, the size of the pores in the hydrogel polymer are regulatable and are formulated to encapsulate genetic material, such as cells or nucleic acids of greater than about 300 base pairs, but to allow smaller particles, such as reagents, enzymes, chemicals, or smaller sized nucleic acids of less than about 50 base pairs, such as primers, to pass through the pores. In some examples, the reagents including reagents for processing genetic material, such as reagents for isolating nucleic acids from a cell, for amplifying or sequencing nucleic acids, or for preparation of nucleic acid libraries. The hydrogels can have any pore size and any porosity, for example a pore size or porosity as described above for hydrogel beads.

"Genetic material," as used herein, refers to cells, microbiomes, or nucleic acids. In some examples, the cell is a single cell, including a prokaryotic or a eukaryotic cell. In some examples, the cell is a mammalian cell. In some examples, the cell is a human cell. In some examples, the cell is a bacterial cell. In some examples, the genetic material is a viral particle. In some examples, the nucleic acid is a long DNA molecule, genomic DNA, viral nucleic acids, bacterial nucleic acids, or mammalian nucleic acids. In some examples, the genetic material is retained within the hydrogel, whereas reagents, enzymes, chemicals, and small nucleic acids of less than about 50 base pairs are capable of passing in and out of the hydrogel.

In some examples, the hydrogel is a hydrogel layer that covers the solid surface of the flow cell device. In some examples, the hydrogel layer is prepared from a hydrogel precursor solution that includes genetic material, and that flows onto the surface of a flow cell device, and which can be further cross-linked while on the surface of the flow cell device to form a polymerized hydrogel layer. In some examples, the hydrogel precursor solution includes a viscosity-modifying agent, such as PEG or dextran, to modulate the viscosity of the solution. In some examples, the hydrogel precursor solution includes a sample containing genetic material.

In some examples, the hydrogel is a hydrogel bead that is captured within the flow cell device. For example, in some examples, the hydrogel bead forms columns along a channel within the flow cell device. In some examples, the hydrogel bead includes genetic material. In some examples, the hydrogel bead includes a hydrogel polymer, a crosslinker, and genetic material. In some examples, the hydrogel polymer includes about 60% to about 90% fluid, such as water, and 10% to about 30% polymer. In certain examples, the water content of hydrogel is about 70-80%.

The hydrogel bead may be prepared using any suitable method, for example, a preparation method as described above for hydrogel beads, such as vortex assisted emulsion or microfluidic flow techniques.

In some examples, a hydrogel bead, whether prepared by vortex assisted emulsion or microfluidic inertial flow assisted emulsion, encapsulates a single or distinct genetic material. For example, in some examples, the hydrogel bead encapsulates a single cell. In some examples, the amount of genetic material within a hydrogel bead can be controlled by diluting the sample containing genetic material. The sample including the genetic material is mixed with hydrogel polymer, and the hydrogel polymer containing the genetic material is submitted to vortex assisted emulsion or microfluidic inertial flow assisted emulsion, as described herein.

In some examples, after preparation of the hydrogel bead containing genetic material, the hydrogel bead is dehydrated to decrease the size of the hydrogel bead. In some examples, the size of the hydrogel bead is decreased by about 1%, about 2%, about 3%, about 4%, about 5%, about 6%, about 7%, about 8%, about 9%, about 10%, about 15%, about 20%, about 30%, about 40%, or about 50%, or an amount within a range defined by any two of the aforementioned values. Thus, for example, a hydrogel bead may be decreased from a hydrated size of 105 µm in diameter to a dehydrated size of less than 100 µm in diameter. In some examples, a dehydrated hydrogel bead having genetic material disposed therein flows onto a flow cell device and rehydrates to a diameter greater than the channel height of the flow cell device, resulting in capture of the hydrogel bead within the flow cell device.

B. Methods of Preparing a Hydrogel Flow Cell Device

Some examples provided herein relate to methods of preparing a hydrogel flow cell device. In some examples, a flow cell device having a solid surface is provided. In some examples, a surface of a flow cell device is coated with a surface polymer, such as those described herein, or such as PAZAM or SFA. In some examples, a hydrogel precursor solution as described herein having a hydrogel polymer, a crosslinker, and genetic material is flowed into the flow cell device, covering the solid surface of the flow cell device. In some examples, a bulk of a hydrogel precursor solution is removed by flowing an immiscible fluid through the flow cell device, which displaces a bulk of the hydrogel precursor solution, and leaves a residual layer of hydrogel precursor solution having genetic material in the flow cell device. In some examples, the immiscible fluid is oil, such as mineral oil, a hydrocarbon oil, a silicon oil, or a polydimethylsiloxane oil, or mixtures thereof. In some examples, the thickness of the hydrogel precursor solution that is retained in the residual layer may be controlled by the viscosity of the hydrogel precursor solution, which may be modulated with the presence of non-reactive polymer species, such as PEG or dextran. In some examples, oil containing a cross-linking agent, such as tetramethylethylenediamine (TEMED) is added to the flow cell device, which initiates cross-linking of the residual layer of the hydrogel precursor solution. In some examples, the oil containing the cross-linking agent is removed, leaving a cross-linked hydrogel layer having genetic material disposed therein on the surface of the flow cell device. In some examples, the cross-linked hydrogel layer covers the surface of the flow cell. In some examples, the flow cell device having the cross-linked hydrogel layer can be used for processing of the genetic material, as described herein.

Some examples provided herein relate to methods of preparing a flow cell device having columns of hydrogel layer disposed therein. In some examples, the method includes providing a flow cell device as described herein. In some examples, the method includes providing hydrogel bead that encapsulate genetic material as described herein. In some examples, the hydrogel beads are dehydrated to a diameter of less than the channel height of the flow cell device. In some examples, the flow cell has a channel height ranging from about 50 µm to about 100 µm, for example, about 50 µm, about 60 µm, about 70 µm, about 80 µm, about 90 µm, about 100 µm, about 110 µm, about 120 µm, about 130 µm, about 140 µm, or about 150 µm, or an amount within a range defined by any two of the aforementioned values. In some examples, the diameter of the dehydrated hydrogel bead ranges from about 2 to about 140 µm, for example, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, or about 140 µm, or a diameter within a range defined by any two of the aforementioned values. Thus, by way of example, a flow cell device may include a channel having a height of 100 µm and a corresponding dehydrated hydrogel bead has a diameter of less than 100 µm, for example, 70 µm in diameter. The dehydrated hydrogel beads are capable of rehydrating, and in so doing, increase in diameter by about 1% to about 50%, for example, about 1%, about 2%, about 3%, about 4%, about 5%, about 6%, about 7%, about 8%, about 9%, about 10%, about 15%, about 20%, about 30%, about 40%, or about 50%, or an amount within a range defined by any two of the aforementioned values. The dehydrated hydrogel beads containing genetic material are flowed into a flow cell device and rehydrated, thereby becoming fixed within the flow cell device. In some examples, the fixed hydrogel beads form pillar structures within the flow cell device. In some examples, the flow cell device having the fixed hydrogel beads that have genetic material encapsulated therein may be used for the processing of genetic material, as described herein.

C. Methods of Processing Genetic Material in a Hydrogel within a Flow Cell Device Some examples provided herein relate to methods of processing genetic material encapsulated within a hydrogel on a solid surface of a flow cell device. In some examples, the flow cell device includes a hydrogel layer that covers the surface of the flow cell device. In some examples, the flow cell device includes trapped hydrogel beads, or pillars, within the flow cell device. Thus, the hydrogel deposited within a flow cell device can include either a hydrogel layer or a hydrogel bead captured within the flow cell device. In some examples, genetic material encapsulated within the hydrogel is contacted with one or more reagents for nucleic acid processing. In some examples, the genetic material is retained within the hydrogel, and reagents are able to pass through the pores of the hydrogel, while at the same time retaining the genetic material within the hydrogel layer, thereby allowing reagents to pass in and out during the processing of the genetic material. In some examples, reagents can include lysis agents, nucleic acid purification agents, DNA amplification agents, tagmentation agents, PCR agents, or other agents used in processing of genetic materials. Thus, the hydrogel retains genetic material for efficient processing of the genetic material within the hydrogel by allowing a barrier for reagents to pass in and out of the hydrogel, while retaining the genetic material itself within the hydrogel.

In some examples, entire DNA library preparation can be accomplished seamlessly inside the hydrogel with multiple reagent exchanges by flowing reagents into the flow cell device while retaining the gDNA and its library products within the hydrogel.

In some examples, reagents are passed through the flow cell device, contacting the hydrogel encapsulating a cell or viral particle to purify and isolate nucleic acids from the cell or particle. Thus, for example lysis buffer is flowed through the flow cell device. As used herein, "lysis" means perturbation or alteration to a cell wall or viral particle facilitating access to or release of the cellular RNA or DNA. Complete disruption and breakage of the cell wall is typically no needed. By the term "lysis buffer" is meant a buffer that contains at least one lysing agent. Typical enzymatic lysing agents include, but are not limited to, lysozyme, glucolase, zymolose, lyticase, proteinase K, proteinase E, and viral endolysins and exolysins. Thus, for example, lysis of cells in the hydrogel may be performed by introducing lysing agents, such as lysozyme and proteinase K into the flow cell device. In some examples, following lysis treatment, isolated nucleic acid is retained within the hydrogel in the flow cell device, and may be used for further processing.

As used herein, the terms "isolated," "to isolate," "isolation," "purified," "to purify," "purification," and grammatical equivalents thereof as used herein, unless specified otherwise, refer to the reduction in the amount of at least one contaminant (such as protein and/or nucleic acid sequence) from a sample or from a source (e.g., a cell) from which the material is isolated. Thus purification results in an "enrichment," or an increase in the amount of a desirable protein and/or nucleic acid sequence in the sample.

In some examples, the isolated DNA following lysis of cells may be amplified by amplification techniques as described herein. In some examples, such as for single cell mRNA sequencing, cDNA synthesis and second strand synthesis ribosomal RNA and double stranded DNA depletion and second strand synthesis following cell lysis may be performed. In some examples, such as for synthetic load read, a lysis step is not required as the genetic material in the hydrogel precursor solution or in the hydrogel beads is nucleic acids, already isolated, and which may be amplified by amplification techniques described herein. One of skill in the art will recognize that the steps provided herein may be modified according to the specific application and the steps for the particular application, and that the disclosure herein generally encompasses nucleic acid library preparations.

The encapsulated nucleic acids that are isolated within the hydrogel can be amplified according to any suitable amplification methodology known in the art, including methods described herein. In some examples, the encapsulated nucleic acids are amplified within the hydrogel. In some examples, the hydrogel is degraded, wherein the encapsulated nucleic acids are released onto the solid support of the flow cell device, and the nucleic acids are amplified within the flow cell device. Amplification may be performed by techniques such as multiple displacement amplification (MDA), which is a widely used technique for amplifying low quantities of DNA, especially from single cells. In some examples, amplification primers and enzymes are introduced to the flow cell device and pass through the pores of the hydrogel and hybridize to the encapsulated nucleic acids. Thus, any of the amplification methodologies described herein or generally known in the art can be utilized with universal or target-specific primers to amplify encapsulated nucleic acids by flowing the appropriate amplification reagents through the flow cell device, thereby amplifying the nucleic acids encapsulated in the hydrogel of the flow cell device.

In some examples, the encapsulated nucleic acids are amplified using cluster amplification methodologies as exemplified by the disclosures of U.S. Pat. Nos. 7,985,565 and 7,115,400, the contents of each of which are incorporated herein by reference in their entirety. The incorporated materials of U.S. Pat. Nos. 7,985,565 and 7,115,400 describe methods of nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein. For example, one or more clusters or colonies can be formed via solid-phase PCR whether one or both primers of each pair of amplification primers are immobilized. In some examples, the encapsulated nucleic acids are amplified within the hydrogel, and then deposited in an array or in a cluster on the flow cell device. Clustering of individual seeded DNA molecules on the flow cell surface can be performed, for example, by standard clustering.

In some examples, the hydrogel is a reversible hydrogel that can be degraded under appropriate conditions, as described herein, including with elevated temperature or with contact with a reducing agent. For example, as shown in FIGS. 18A-18B, the hydrogel may be a hydrogel bead that may be degraded, thereby releasing the genetic material in clusters. In FIG. 18A, hydrogel beads are individually encapsulated and the beads chemically break to release DNA for clustering. As shown in FIG. 18B, DNA clustered on the flow cell surface, and is ready for sequencing.

Additional amplification methods include isothermal amplification. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'→3' exo- for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety. In some examples, the polymerases, reagents, and components for performing these amplification reactions are introduced to a flow cell device and are capable of passing through the pores of the hydrogel to interact with the encapsulated nucleic acids, thereby amplifying the nucleic acids within the hydrogel (whether the hydrogel is a layer coating the surface of the flow cell device or a hydrogel bead or pillar, as described herein).

In some examples, the encapsulated nucleic acids are sequenced in full or in part within the hydrogel. The encapsulated nucleic acids can be sequenced according to any suitable sequencing methodology including those described herein, such as direct sequencing, including sequencing by synthesis, sequencing by ligation, sequencing by hybridization, nanopore sequencing and the like.

In some examples, one or more amplified encapsulated nucleic acids can be subjected to an SBS or other detection technique that involves repeated delivery of reagents in cycles. For example, to initiate a first SBS cycle, one or more labeled nucleotides, DNA polymerase, etc., can be flowed into/through a hydrogel bead that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for examples that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemple SBS procedures, fluidic systems and detection platforms that can be readily adapted for use with amplicons produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Example methods for array-based expression and genotyping analysis that can be applied to detection according to the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference.

In the methods of isolating nucleic acids, amplification, and sequencing as described herein, various reagents are used for nucleic acid isolation and preparation. Such reagents may include, for example, lysozyme, proteinase K, random hexamers, polymerase (for example, Φ29 DNA polymerase, Taq polymerase, Bsu polymerase), transposase (for example, Tn5), primers (for example, P5 and P7 adapter sequences), ligase, catalyzing enzyme, deoxynucleotide triphosphates, buffers, or divalent cations. These reagents are introduced to the flow cell device, alone or in combination, as needed for each processing step, and pass through the pores of the hydrogel in the flow cell device, whereas the genetic material is retained within the hydrogel and processed therein. An advantage of the methods set forth herein is that they provide for an encapsulated microenvironment for the processing of nucleic acids within a hydrogel on a flow cell device, thereby providing a simplified nucleic acid processing system. This enables single cell processing for rapid and efficient processing of a target nucleic acid within a flow cell device. Adapters can include sequencing primer sites, amplification primer sites, and indexes. In some examples, nucleic acid libraries can be prepared within a hydrogel on a flow cell device. In some examples, for example, genetic material encapsulated within a hydrogel may be used for combinatorial indexing of the single cells, for example, using a contiguity preserving transposition (CPTSeq) approach. In some examples, nucleic acids from a single cell may be barcoded by encapsulation of single cells after WGA amplification with barcoded transposons dissolving the hydrogel by contacting it with a reducing agent, for example, to release genomic DNA for barcoding.

Additionally, examples of the "spatial indexing" methods and techniques described herein shorten data analysis and simplify the process of library preparation from single cells and long DNA molecules. Existing protocols for single cell sequencing involve efficient physical separation of the cells and uniquely barcoding each isolated cell and pooling everything back together to do sequencing. Current protocols for synthetic long reads typically utilize cumbersome barcoding steps, and pooling each barcoded fragments together for sequencing and letting data analysis to distinguish genetic information coming from each barcoded cell. During these long processes there is also loss of genetic material which causes dropouts in the sequences. Examples described herein not only shorten the process but also increase data resolution for single cells. Furthermore, examples provided herein simplify the assembly of genomes of new organisms. Examples described herein may be used to reveal rare genetic variations and co-occurrence of mutations. In some examples, DNA library confined in the hydrogel beads until release provide the opportunity to control the size of the fragments that is released on the surface by controlling the release process and hydrogel formulation.

D. Preparing Nucleic Acid Libraries on a Flow Cell Device within the Hydrogel

In some examples, sequencing libraries can be prepared from the genetic material (such as target nucleic acid molecules) encapsulated within the hydrogel on the flow cell device. For example, the sequencing library can be prepared as described above for preparation of sequencing libraries in hydrogel beads. In several examples, the target nucleic acid is isolated from a single cell encapsulated within the hydrogel on the flow cell device.

In some examples, the genetic material entrapped (for example, single cells) within the hydrogel on the hydrogel flow cell device is lysed, and isolated nucleic acids are further processed by amplification, tagmentation, or other nucleic acid library preparation method, and then seeded onto the surface of a flow cell device. In some examples, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate. In some examples, the array of wells or depressions are from about 10 µm to about 50 µm in diameter, such as about 10 µm, about 15 µm, about 20 µm, about 25 µm, about 30 µm, about 35 µm, about 40 µm, about 45 µm, or about 50 µm in diameter, or a diameter within a range defined by any two of the aforementioned values. In some examples, the wells or depressions have a depth of about 0.5 µm to about 1 µm, such as about 0.5 µm, about 0.6 µm, about 0.7 µm, about 0.8 µm, about 0.9 µm, or about 1 µm in depth, or a depth within a range defined by any two of the aforementioned values. In some examples, the wells or depressions are made of a hydrophobic material. In some examples, the hydrophobic material includes an amorphous fluoropolymer, including for example, CYTOP, Fluoropel®, or Teflon®. In some examples, the hydrophobic nature of the wells improves isolation of individual cell genomic DNA during enzymatic processing and reduces cross-talk between populations of seeded DNA.

Examples of the systems and methods provided herein include kits, containing any one or more of the hydrogel polymers, crosslinkers, or microfluidic devices for preparing hydrogel beads that encapsulate genetic material, and further including components useful for processing of the genetic material, including reagents for cell lysis, and nucleic acid amplification and sequencing, or for nucleic acid library preparation, including lysozyme, proteinase K, random hexamers, polymerase (for example, Φ29 DNA polymerase, Taq polymerase, Bsu polymerase), transposase (for example, Tn5), primers (for example, P5 and P7 adapter sequences), ligase, catalyzing enzyme, deoxynucleotide triphosphates, buffers, or divalent cations as described herein, and as used for the respective processing of genetic material.

Additional Examples

Clause 1. A flow cell device for performing single cell sequencing, comprising:
a solid support comprising a surface having a degradable hydrogel deposited thereon, wherein the degradable hydrogel comprises pores that are sized to allow diffusion of a reagent through the hydrogel, but are too small to allow genetic material to traverse the pores.

Clause 2. The flow cell device of Clause 1, wherein the solid support is functionalized with a surface polymer.

Clause 3. The flow cell device of Clause 2, wherein the surface polymer is poly(N-(5-azidoacetamidylpentyl) acrylamide-co-acrylamide) (PAZAM) or silane free acrylamide (SFA).

Clause 4. The flow cell device of any one of Clauses 1-3, wherein the flow cell comprises a patterned surface.

Clause 5. The flow cell device of Clause 4, wherein the patterned surface comprises wells.

Clause 6. The flow cell device of Clause 5, wherein the wells are from about 10 μm to about 50 μm in diameter, such as 10 μm, 15 μm, 20 μm, 25 μm, 30 μm, 35 μm, 40 μm, 45 μm, or 50 μm in diameter, or within a range defined by any two of the aforementioned values, and wherein the wells are about 0.5 μm to about 1 μm in depth, such as 0.5 μm, 0.6 μm, 0.7 μm, 0.8 μm, 0.9 μm, or 1 μm in depth, or within a range defined by any two of the aforementioned values.

Clause 7. The flow cell device of any one of Clauses 5-6, wherein the wells are comprised of hydrophobic material.

Clause 8. The flow cell device of Clause 7, wherein the hydrophobic material comprises an amorphous fluoropolymer, such as CYTOP, Fluoropel®, or Teflon®.

Clause 9. The flow cell device of any one of Clauses 1-8, wherein the degradable hydrogel is a hydrogel bead or a hydrogel layer.

Clause 10. The flow cell device of Clause 9, wherein the hydrogel bead has a diameter of about 2 μm to about 120 μm.

Clause 11. The flow cell device of any one of Clauses 1-10, wherein the hydrogel comprises polyethylene glycol (PEG)-thiol, PEG-acrylate, acrylamide, N,N'-bis(acryloyl) cystamine (BACy), PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations or mixtures thereof.

Clause 12. The flow cell device of Clause 11, wherein the hydrogel comprises PEG-thiol/PEG-acrylate, acrylamide/N, N'-bis(acryloyl)cystamine (BACy), or PEG/PPO.

Clause 13. The flow cell device of any one of Clauses 1-12, wherein the genetic material comprises a cell, a nucleic acid, or a microbiome.

Clause 14. The flow cell device of Clause 13, wherein the cell is a mammalian cell or bacterial cell.

Clause 15. The flow cell device of Clause 13, wherein the cell is a human cell.

Clause 16. The flow cell device of any one of Clauses 13-14, wherein the cell is an *Escherichia coli* cell, a *Bacillus subtilis* cell, an *Aeromonas hydrophila* cell, or a fibroblast cell.

Clause 17. The flow cell device of Clause 13, wherein the nucleic acid is DNA or RNA of 300 base pairs or greater.

Clause 18. The flow cell device of any one of Clauses 1-17, wherein the reagent comprises enzymes, chemicals, and primers having a size of less than 50 basepairs.

Clause 19. The flow cell device of any one of Clauses 1-18, wherein the reagent comprises lysozyme, proteinase K, random hexamers, polymerase (Φ29 DNA polymerase, Taq polymerase, Bsu polymerase), transposase (Tn5), primers (P5 and P7 adapter sequences), ligase, catalyzing enzyme, deoxynucleotide triphosphates, buffers, or divalent cations.

Clause 20. A system for single cell sequencing, comprising:
a stage configured to hold a flow cell device of any one of Clauses 1-19; a flow cell device of any one of Clauses 1-19; and
a detector for obtaining sequencing data.

Clause 21. A method of preparing a nucleic acid library on a flow cell device, comprising:
providing a flow cell device of any one of Clauses 1-19;
isolating nucleic acids from the genetic material in the hydrogel; and preparing a nucleic acid library from the isolated nucleic acids.

Clause 22. The method of Clause 21, further comprising:
releasing the nucleic acid library from the hydrogel, thereby seeding the nucleic acid library on the surface of the flow cell device; and
amplifying and sequencing the nucleic acid library.

Clause 23. The method of any one of Clauses 21-22, wherein isolating nucleic acids from the genetic material in the hydrogel comprises contacting the genetic material with a lysis agent to extract nucleic acids.

Clause 24. The method of Clause 23, wherein the lysis agent comprises lysozyme or proteinase K.

Clause 25. The method of any one of Clauses 21-24, wherein preparing a nucleic acid library comprises contacting genetic material with a transposase mixture comprising adapter sequences and transposomes.

Clause 26. The method of any one of Clauses 22-25, wherein releasing the nucleic acid library from the hydrogel comprises decomposing the hydrogel by contacting the hydrogel with a cleavage mix or by heating the hydrogel to a temperature of about 90° C., thereby releasing the nucleic acid library Clause 27. The method of Clause 26, wherein the cleavage mix comprises dithiothreitol (DTT), tris(2-carboxyethyl)phosphine (TCEP), or tris(3-hydroxypropyl)phosphine (THP).

WORKING EXAMPLES

The following examples are provided to illustrate particular features of certain examples, but the scope of the claims should not be limited to those features exemplified.

Example 1

Flow Cell Capture of Degradable Hydrogel Beads Containing Encapsulated Nucleic Acid Molecules This example illustrates preparation of hydrogel beads encapsulating nucleic acid molecules using manual vortexing and microfluidic droplet generators.

The pore size of the hydrogel bead was selected to allow the diffusion of enzymes, chemicals and smaller sized primers (<50 bps), but retained the larger sized DNA (>300 bps) such that the genomic DNA and the produced DNA library is retained inside the gel microbeads during library preparation.

A hydrogel solution of 12% was prepared from 40% acrylamide/bis 19:1 (BioRad #161-0144) diluted with deionized water. A 40% (w/v) acrylamide/N,N'bis(acryloyl) cystamine (BACy) (19:1) monomer stock solution (3.8 g of acrylamide, 0.2 g of BACy, and 6 mL of double distilled (dd) H20) was prepared. The mixture was brought to a final volume of 10 mL. To prepare the solution, the acrylamide was dissolved in 6 mL of ddH20, and the resulting solution was used to dissolve the BACy. The dissolution of the monomers is endothermic, so heating the mixture slightly will help completely dissolve the monomers. The hydrogel solution was maintained at 4° C. until use. 35 µL of saturated potassium persulfate solution (KPS; Sigma) was added to 200 µL of the 12% hydrogel solution and mixed well.

Samples of genomic DNA were transferred to a sterile 1.7 mL tube. The 235 µL hydrogel-KPS solution was added to each tube containing a genomic DNA sample. The hydrogel-genomic DNA solution was then loaded into 600 µL mineral oil with surfactant (4.5% Span 80, 0.4% Tween 20, and 0.05% Triton X-100). The solution was vortexed for 30 seconds to generate droplet emulsion, and 25 µL of TEMED (Sigma) was immediately added, followed by another 30 seconds of vortexing.

To make a 10% gel with acrylamide/BACy ratio of 19:1 (2 mL), 0.96 mL of ddH20, 0.5 mL of 40% acrylamide/BACy (19:1), 0.5 mL of 10× tris/borate/EDTA buffer (TBE), 20 µL of TEMED and 20 µL of KPS (saturated) were mixed.

To make a 5% gel with acrylamide/BACy ratio of 19:1 (2 mL), 1.21 mL of ddH20, 0.25 mL of 40% acrylamide/BACy (19:1), 0.5 mL of 1 0x TBE, 20 µL of TEMED and 20 µL of KPS (saturated) were mixed. The reaction was allowed to polymerize until gelation (6 min).

Hydrogel beads encapsulating genomic DNA were then generated. After incubation for 15 minutes to allow the hydrogel beads to fully cross-link, about 900 µL of petroleum ether was added to each tube. Tubes were vortexed to wash away the oil, and supernatant was removed. The hydrogel beads were washed, followed by vortexing, and spinning down the beads. The beads were resuspended and can be stored in 4° C. for at least 3 weeks.

The method described above using manual emulsion was used to generate hydrogel beads having a size distribution of from about 2 µm to about 100 µm in diameter.

To generate hydrogel beads of a uniform size distribution, a microfluidic droplet generator was used (see FIG. 3). An aqueous solution containing a hydrogel polymer and genomic DNA fragments was loaded onto the cartridge of a microfluidic droplet generator and introduced into mineral oil in the microfluidic droplet generator (FIG. 3A). The microfluidic device had a height of 120 µm, with an aqueous channel width of 75 µm and a carrier oil channel width of 78 µm. With this device, flow rates of 60 µl/min for the aqueous channel and 300 µl/min for the carrier oil channel were used.

Using this device, hydrogel beads of approximately 120 µm in diameter were generated (FIG. 3B). The size of the beads can be finely tuned by adjusting the channel widths, the microfluidic device size, and the flow rates.

The hydrogel beads containing the genomic DNA fragments were immobilized on a MiSeq™ sequencing flow cell (FIG. 3C) (Illumina, San Diego, Calif.). The beads were captured on the flow cell due to physical constraint. The hydrogel beads are about 120 µm in diameter and the channel of the sequencing flow cell is about 100 µm in height. The flow cell with the captured beads was inserted into a MiSeq™ sequencer for further processing (FIG. 3D).

Example 2

In-Bead Sequencing Library Preparation and Flow Cell Seeding

This example demonstrates a process for preparing a sequencing library from genomic DNA contained within a hydrogel bead captured on a sequencing flow cell, and the subsequent seeding of the prepared nucleic library on the flow cell.

Hydrogel beads containing encapsulated genomic DNA fragments were captured on the surface of a MiSeq™ flow cell as described in Example 1. Solution containing enzymes and reagents for preparation of DNA library from the genomic DNA in the beads captured on the sequencing flow cell was flowed onto the flow cell to prepare the DNA library in the hydrogel bead (FIGS. 4A and 4B). The captured hydrogel beads have a pore size that allows the diffusion of enzymes, chemicals and smaller sized primers (<50 bps), but retains larger sized DNA (>300 bps). Mineral oil was then loaded onto the sequencing flow cell to fill the void between beads and surround the captured hydrogel beads containing the DNA library. The temperature of the MiSeq™ flow cell was then raised to 90° C. for 3 minutes to denature the DNA library and degrade the hydrogel beads. As shown in FIG. 4C, the denatured DNA library diffused out of the hydrogel beads, and due to the presence of the mineral oil, remained in a region defined by the diameter of the bead. Thus, in the presence of the oil, seeding occurs in close proximity to the footprint of each hydrogel bead (from 120 µm diameter hydrogel beads, library seeding is limited to about 120 µm diameter area). The temperature of the MiSeq™ flow cell was lowered to 60° C. for 6 minutes, 40° C. for 2 minutes, and 20° C. for 2 minutes to allow the single stranded DNA library to hybridize to the surface P5/P7 primers on the flow cell to seed the library on the surface of the flow cell.

Subsequently, the seeded library can be clustered, and sequenced with standard SBS chemistry.

Example 3

Sequencing Nucleic Acids Using Hydrogel Beads

This example provides results of sequencing assays using hydrogel beads for spatial indexing of nucleic acid molecules on a flow cell surface.

Three different workflows were assayed for the sequencing of long DNA molecules (see FIGS. 5A-5C). Two different DNA fragment lengths (~100 kb and ~10 kb) were tested, as well as an in-bead MDA step to amplify the genomic DNA in the hydrogel beads prior to sequencing library preparation.

Hydrogel beads containing encapsulated genomic DNA fragments of ~100 kb or ~10 kb were generated as discussed in Example 1. For each fragment length, in-bead MDA prior to library generation was assessed.

The resulting hydrogel beads were loaded onto a MiSeq™ sequencing flow cell and sequencing libraries were generated by tagmentation reaction using Nextera™ (Illumina, San Diego, Calif.) reagents and procedures. Mineral oil was then loaded to the flow cell to surround the captured beads. The temperature of the flow cell was then raised to 90° C. for 3 minutes to denature the DNA library and degrade the hydrogel beads. The denatured DNA library diffused out of the hydrogel beads, and due to the presence of the mineral oil, remained in the region defined by the diameter of the bead. The temperature of the MiSeq™ Flow cell was lowered to 60° C. for 6 minutes, 40° C. for 2 minutes, and 20° C. for 2 minutes to allow the single stranded DNA library to hybridize to the surface P5/P7 primers on the flow cell to seed the library on the surface of the flow cell. Subsequently, the seeded library was clustered and sequenced with standard SBS chemistry and reads were processed using strobe- and linked-read analysis.

Figure 6:
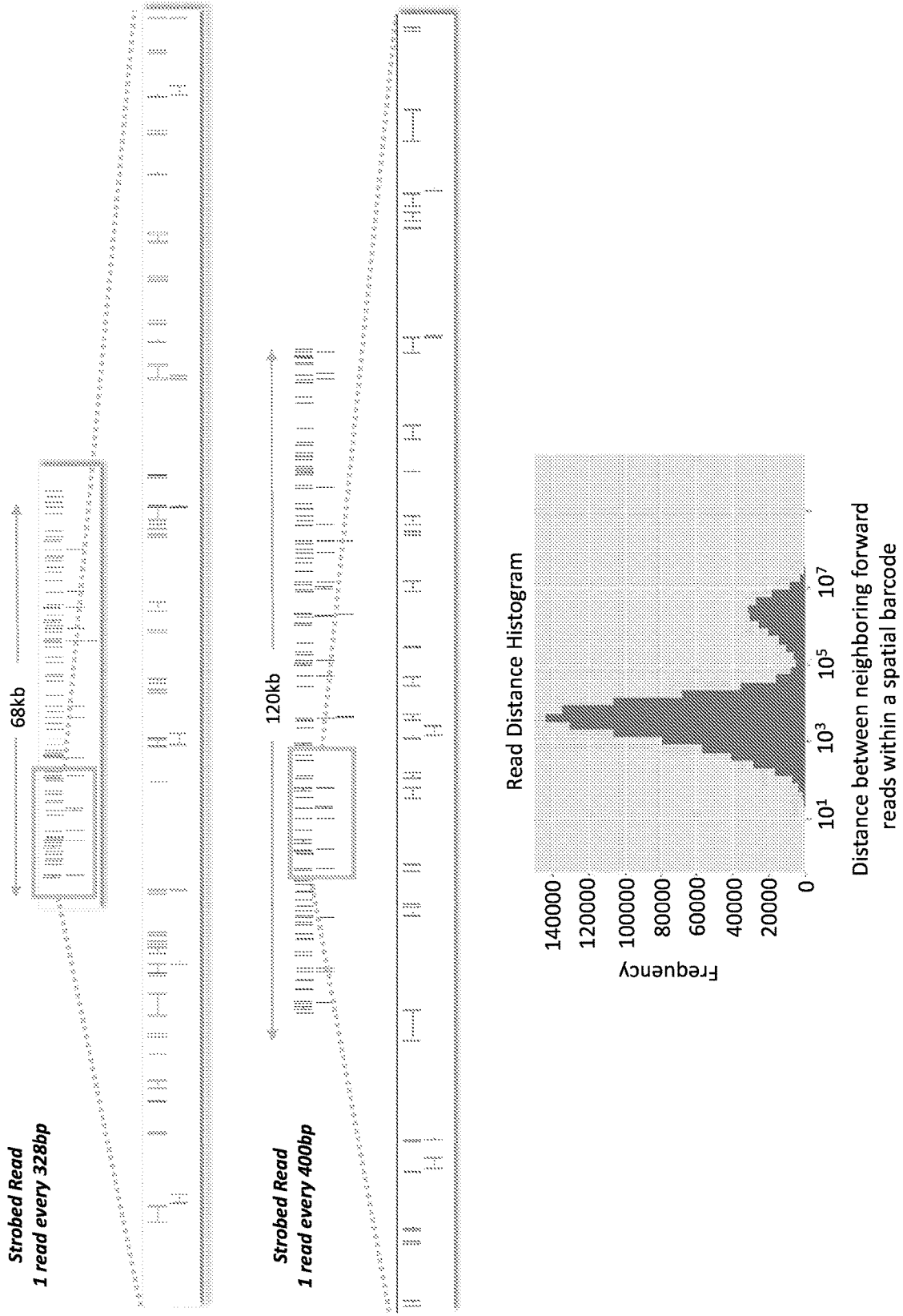
FIG. 6 depicts sequencing results of flow cell seeded with hydrogel beads containing human genomic DNA having a fragment size of ~100 kb with ~100 fragments per bead.

In the first assay (see FIG. 6), hydrogel beads were generated containing human (Corriell) genomic DNA having a fragment size of ~100 kb with ~100 fragments per bead. In-bead MDA amplification prior to in-bead sequencing library generation was not performed. Strobed read analysis of the resulting sequence reads (1 read every 328 or 400 bp) showed an average of ~405 sequence islands per bead, with an average island size of 64 kb and an average of 33 clusters per island.

Figure 7:
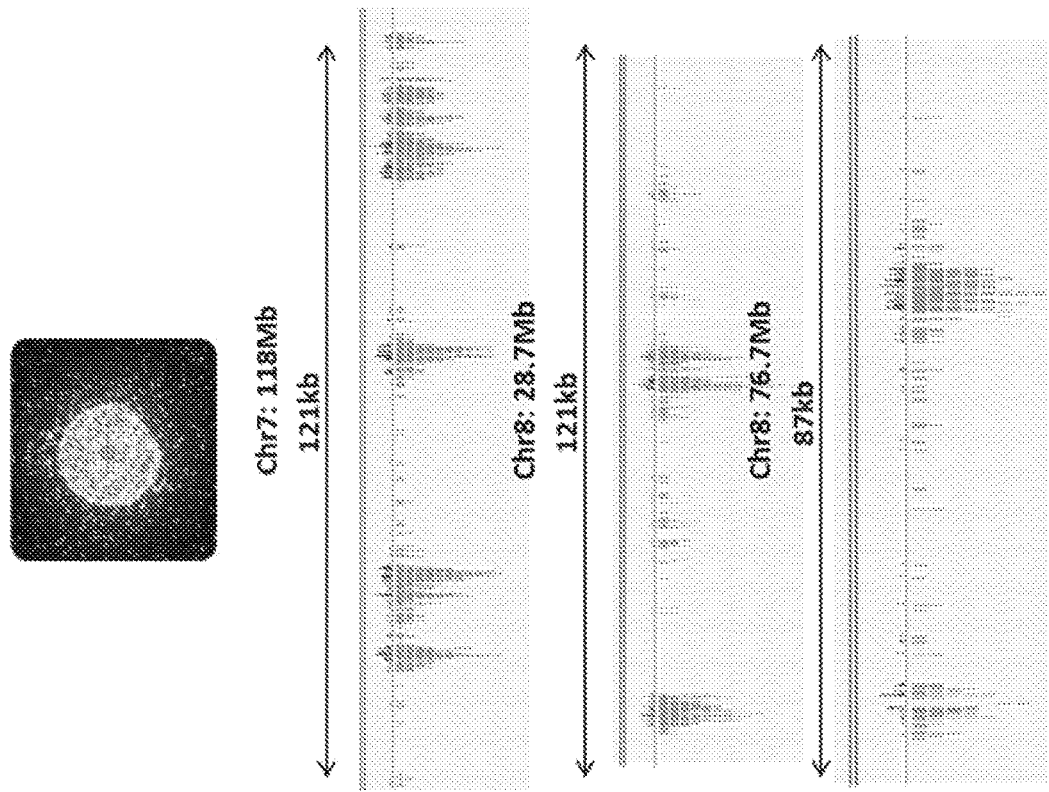
FIG. 7 depicts sequencing results of flow cell seeded with hydrogel beads containing human genomic DNA having a fragment size of ~100 kb with ~50 fragments per bead. The genomic DNA in the hydrogel beads was amplified by MDA amplification prior to flow cell capture and in-bead library generation.

In the second assay (see FIG. 7), hydrogel beads were generated containing human (Corriell) genomic DNA having a fragment size of ~100 kb with ~50 fragments per bead. MDA amplification prior to in-bead sequencing library generation was performed. Linked-read analysis of the resulting sequence reads showed an average of ~166 sequence islands per bead, with an average island size of 58 kb and an average of 85 clusters per island.

In the third assay (see FIG. 8), hydrogel beads were generated containing human (Corriell) genomic DNA having a fragment size of ~10 kb with ~100 fragments per bead. In-bead MDA amplification prior to in-bead sequencing library generation was performed. Linked-read analysis of the resulting sequence reads showed an average of ~85 sequence islands per bead, with an average island size of 10.4 kb and an average of 57 clusters per island.

Taken together, the results demonstrate the utility of assays using hydrogel beads provide spatial indexing for seeding and sequencing long DNA molecules. Further, the spatial segregation of the cluster patches on the flow cell surface enables the target nucleic acid molecules to be reconstructed from shorter sequence reads from individual cluster-patches.

Example 4

Hydrogel Beads with a Hollow Core

This example illustrates construction of hydrogel beads with a hollow core containing encapsulated target nucleic acid molecules.

FIG. 9A provides a schematic diagram illustrating construction of the hollow hydrogel beads. First, an inner hydrogel layer is formed that contain encapsulated genetic material, such as target nucleic acid molecules. The inner hydrogel layer is then encapsulated with an outer hydrogel layer. The inner hydrogel layer is then depolymerized using an agent that does not depolymerize the outer hydrogel layer, leaving the outer hydrogel layer with a hollow space containing the genetic material.

FIG. 9B shows micrographs of an inner polyacrylamide hydrogel core containing encapsulated nucleic acid molecules before (left) and after (right) encapsulation with an outer polyacrylamide shell and depolymerization of the core hydrogel using a depolymerization agent that cleaves the crosslinker used to form the inner hydrogel. FIG. 9C shows micrographs of an inner agarose hydrogel core containing encapsulated nucleic acid molecules before (left) and after (right) encapsulation with an outer polyacrylamide shell and depolymerization of the core hydrogel by heating to 60° C.

The resulting hollow hydrogel beads containing encapsulated nucleic acid molecules can be loaded onto a sequencing flow cell for sequencing of the nucleic acid molecules as described herein.

Example 5

Use of Cell Lysate to Generate Degradable Hydrogel Beads Encapsulating Target Nucleic Acid Molecules This example provides results of sequencing assays using hydrogel beads for spatial indexing of nucleic acid molecules on a flow cell surface, wherein the hydrogel beads contain encapsulated target nucleic acid molecules prepared in-bead from cell lysate.

Figure 10B:
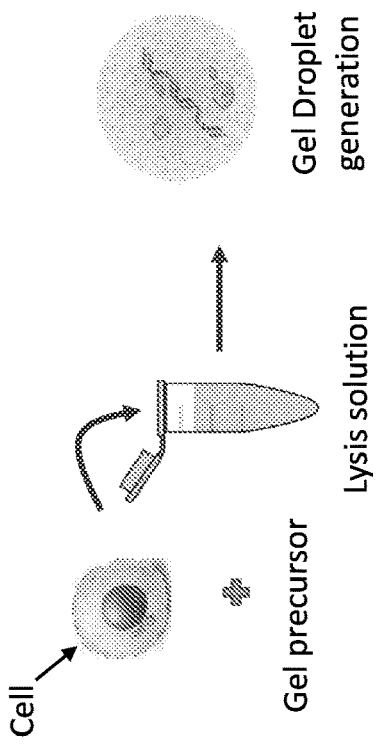
Figure 10C:
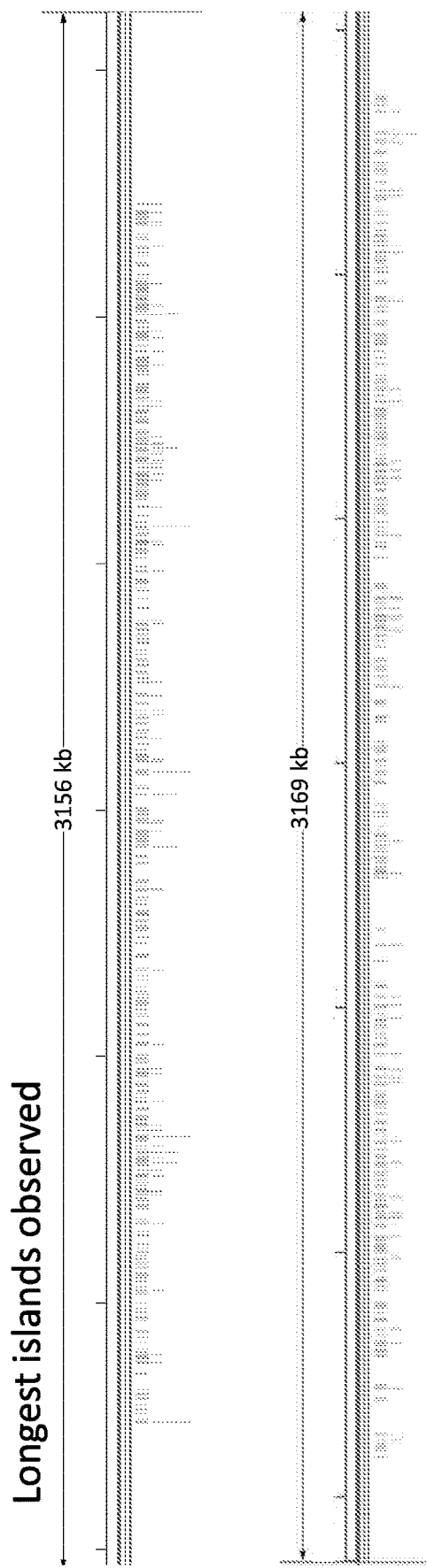

Human cells from tissue culture were directly added to lysis buffer (50 mM Tris-HCl pH 8.0, 5 mM EDTA, 0.5% SDS and 50 µg/ml RNAse A) and incubated for 5 mins. Then, hydrogel precursor solution as described in Example 1 was added to the lysate in 1:1 proportion and the resulting solution was provided to the input of a droplet generator to generate the hydrogel beads. The beads were loaded onto a sequencing flow cell, sequencing libraries were prepared and seeded onto the flow cell surface, and a sequencing assay was performed as described in Examples 2 and 3. Island size distribution and the longest islands observed are shown in FIGS. 10B and 10C.

Example 6

Sample Multiplexing

This examples illustrates examples of sample indexing methods can be used to interrogate multiple nucleic acid samples on a single sequencing flow cell.

To generate linked-long-read information from multiple samples in the same flow cell lane, transposons with different indexes can be used to label each sample with a different index that is subsequently relied upon to identify cluster patches corresponding to each sample. The target nucleic acid molecules are tagmented with a unique index for each sample prior to bead capture on the flow cell. Different human genomic DNA samples are encapsulated in hydrogel beads as discussed in Example 1 and are separately tagmented using different indexed transposons prior to loading of the beads on the flow cell. The hydrogel beads containing the tagmented DNA are pooled and captured on a sequencing flow cell, after which sequencing library preparation is completed, a liquid diffusion barrier is loaded onto the sequence flow cell, and the hydrogel beads are degraded in the presence of the liquid diffusion barrier to seed the sequencing libraries on the flow cell surface. The seeded patches contain different DNA index sequences corresponding to different samples and can be separated from each other during post-sequencing read analysis.

Figure 11:
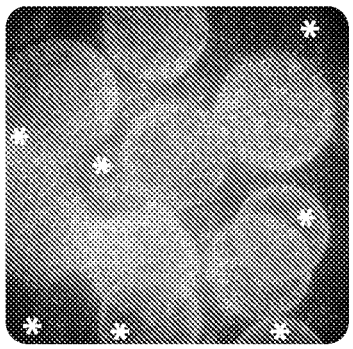
FIG. 11 shows an image generated from superimposed hydrogel DNA patches from two different samples (each carrying a different DNA barcode introduced during the tagmentation step) processed using a sequential seeding strategy. Cluster patches from the first sample are marked with an asterisk (*); patches from the second sample are unmarked.

In an additional example, to generate linked-long-read information from multiple samples in the same flow cell lane, the hydrogel beads from each sample were processed sequentially on the flow cell, using differently indexed transposons for each sample, to identify cluster patches corresponding to each sample. The beads containing the first sample were loaded onto the flow cell and target nucleic acids were tagmented using indexed transposon. After the library from first sample was released from the bead and seeded on to the flow cell, a second round of hydrogel beads containing a second target nucleic acid sample was loaded onto the flow cell and was tagmented using a distinct indexed transposon to generated a second indexed library which was released in spatially confined manner for seeding on the flow cell surface. This provides seeded patches containing different DNA index sequences corresponding to different samples that can be separated from each other during post-sequencing read analysis. FIG. 11 shows an image generated from superimposed hydrogel DNA patches from two different samples (each carrying a different DNA barcode introduced during the tagmentation step) processed using this sequential seeding strategy. Cluster patches from the first sample are marked with an asterisk (*); patches from the second sample are unmarked.

In an additional example, to generate linked-long-read information from multiple samples in the same flow cell lane, exogenous nucleic acid molecules can be spiked into different target nucleic acid samples at the encapsulation step. Different human genomic DNA samples are mixed with distinct exogenous DNA markers (such as Phi-X, λ1, λ3 or λ3 DNA), and the mixture is encapsulated in hydrogel beads as discussed in Example 1. The hydrogel beads generated from each sample are pooled, loaded on the sequencing flow cell, tagmented to generate sequencing libraries, and degraded in the presence of a liquid diffusion barrier to seed the sequencing libraries on the flow cell surface. The exogenous nucleic acid molecules serve as a marker to identify seeded patches corresponding to each sample.

Figure 12B:
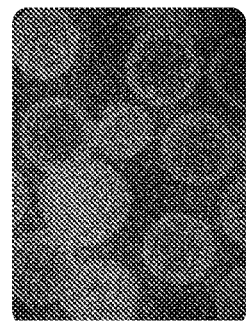
FIGS. 12A and 12B show a set of micrographs showing the seeding of interstitial space between hydrogel bead clusters with standard short read library to maximize flow-cell utilization. The micrographs show seeded library using hydrogel beads for spatial indexing before (FIG. 12A) and after (FIG. 12B) seeding of the interstitial space between cluster patches from hydrogel beads with standard short read library to maximize flow cell utilization.
Figure 12A:
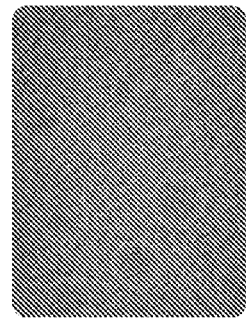

In an additional example, to maximize utilization of the flow cell for sequencing data generation, and optionally to generate read information from multiple samples in the same flow cell lane, an additional step was added to the workflow following seeding of sequencing library from the hydrogel beads. At this stage, the interstitial space between the hydrogel bead footprints on the flow cell has a low density of seeded library. To utilize this interstitial space, an additional seeding step was performed using a regular short read sequencing library produced from the same target nucleic acid sample as that encapsulated in the hydrogel beads. This short read library was seeded onto the sequencing flow cell using standard methods and contains a DNA index distinct from that used for the library encapsulated within the hydrogel beads to separate the reads from the linked-long read and short read libraries. FIG. 12 shows corresponding pseudo-images from before and after seeding of the interstitial space. Using this approach, greater coverage of the target DNA sample was achieved, which provides improved SNP identification accuracy.

Example 7

Method of Making Flow Cell Device with a Hydrogel Layer

The following example demonstrates a method of making a flow cell device having a hydrogel layer deposited thereon.

Figure 13A:
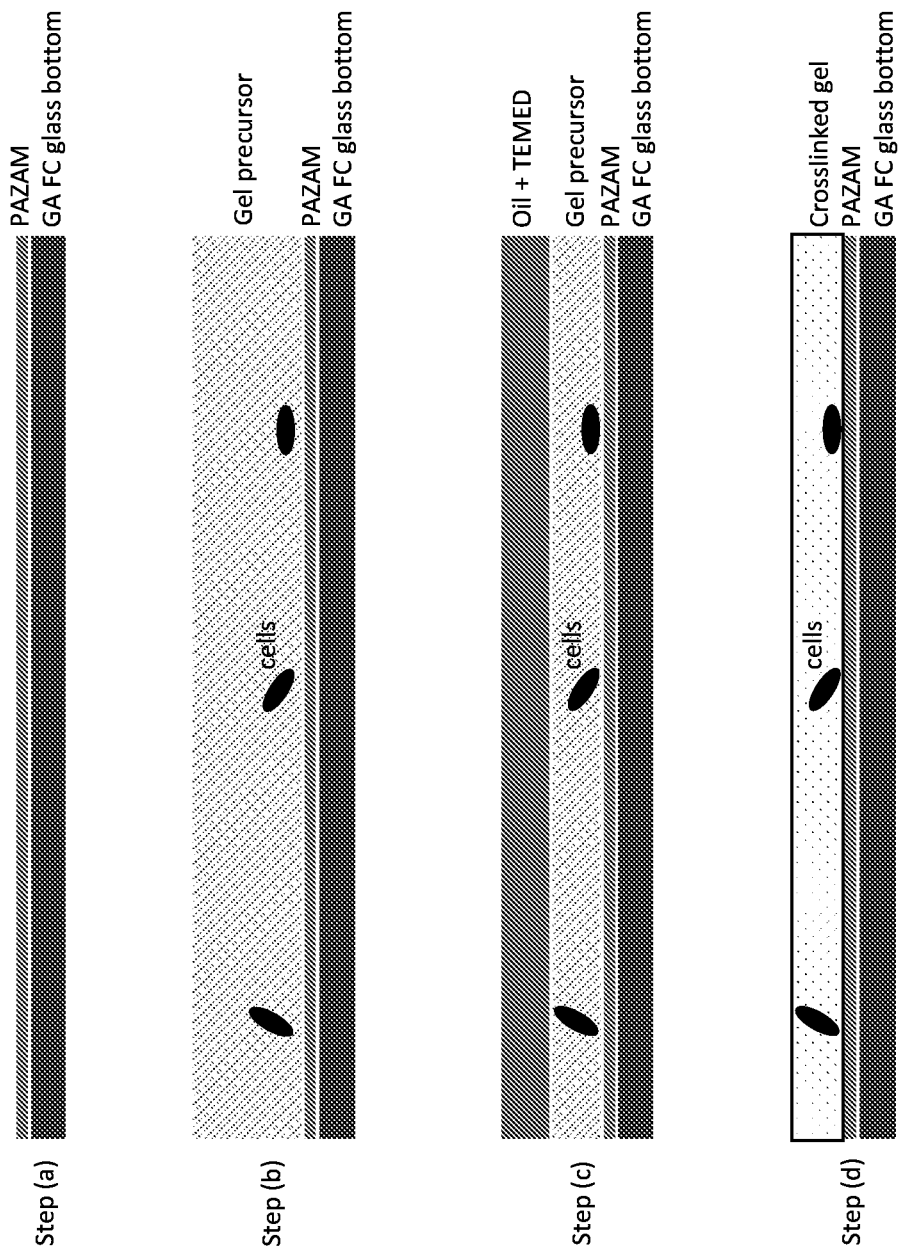
FIGS. 13A and 13B depict a schematic outline according to one example of a method to prepare a nucleic acid library.

A flow cell device having a surface was coated with a surface polymer, such as PAZAM or SFA, as shown in FIG. 13A, step (a). As shown in step (b), a hydrogel precursor solution having a hydrogel polymer, a crosslinker, and cells was flowed into the flow cell device, covering the solid surface of the flow cell device. The bulk of the hydrogel precursor solution was displaced with oil to create a residual hydrogel film containing genetic material. Oil containing TEMED (25 µL of TEMED in 600 µL of mineral oil) was then flowed across the surface to initiate crosslinking of the residual hydrogel film, as shown in step (c). The oil containing the cross-linking agent was removed, leaving behind cells in cross-linked hydrogel matrix, as shown in step (d).

Example 8

Method of Clustering Seeded DNA Molecules in a Flow Cell Device Having a Hydrogel Layer The following example demonstrates a method of clustering seeded DNA molecules in a flow cell device made in Example 7, having cells encapsulated in the hydrogel layer.

Figure 13B:
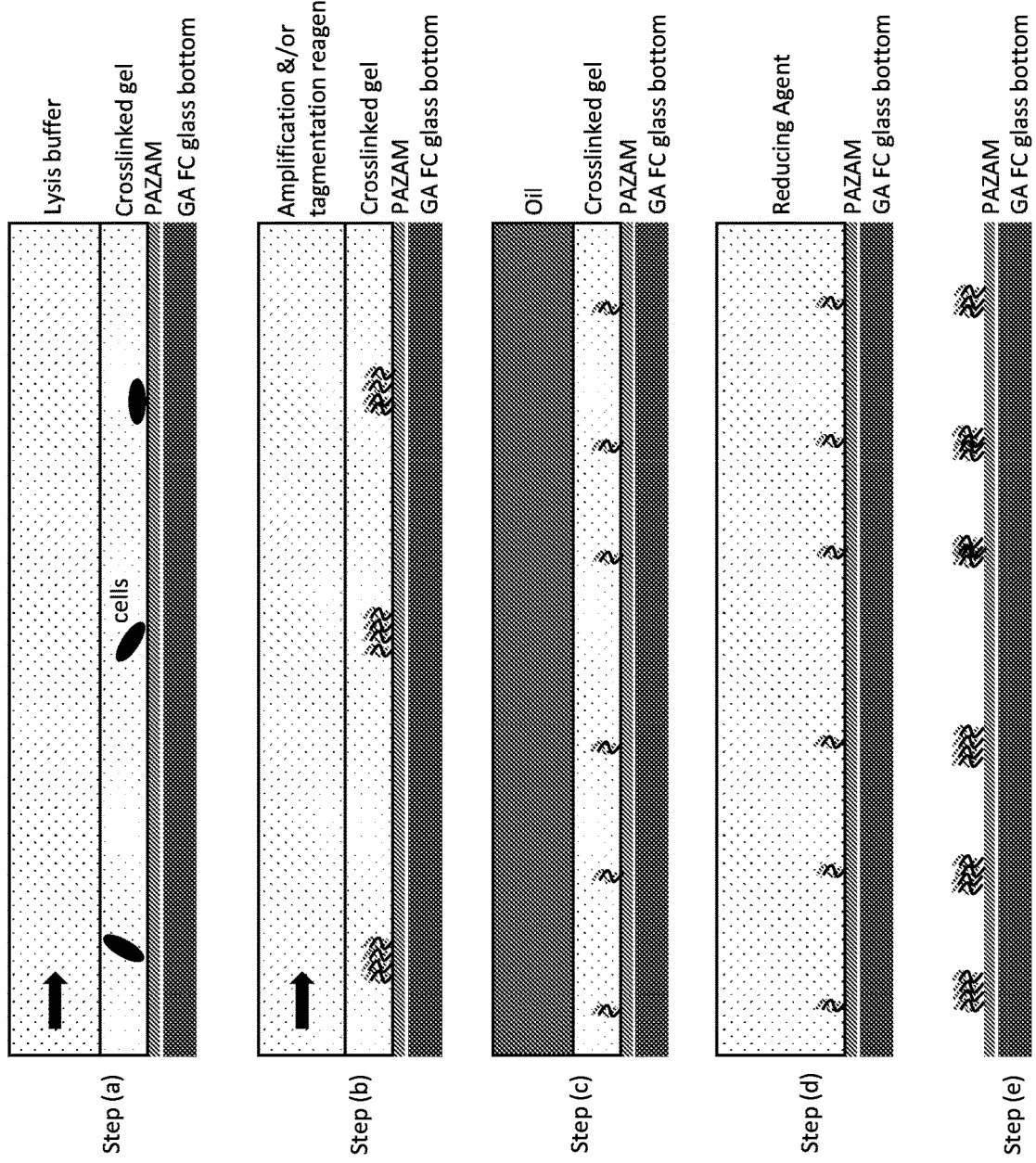

A flow cell device of Example 7, having a hydrogel layer with cells deposited therein was prepared. Lysis buffer was introduced to the flow cell device, as shown in FIG. 13B, step (a). Lysis agents in the lysis buffer permeabilized the cell wall of cells in the cross-linked hydrogel layer. Lysis agents used included lysozymes or detergents. Proteinase K was introduced to the flow cell device to release nucleic acids from bound complexes.

Next, the single cell genomic DNA molecules were amplified using MDA to create several copies of the DNA, as shown in FIG. 13B, step (b), by introducing MDA reagents to the flow cell device. The surface of the flow cell device was then washed with buffer to allow short amplicons to diffuse out of the hydrogel layer and oil was introduced to the flow cell device, covering the layer. The surface was heated to 80° C. to promote lateral diffusion of the DNA molecules to seed them apart from the initial capture location, as shown in FIG. 13B, step (c). Once the DNA was seeded on the PAZAM layer, the cross-linked gel was washed out using a reducing agent, such as THP, TCEP, or DTT, which uncrosslinks the gel, as shown in FIG. 13B, step (d).

Finally the individual seeded DNA molecules were clustered using eXAMP or standard clustering, as shown in FIG. 13B, step (e). The resulting sequencing data was assembled using spatial information of the clusters, which was obtainable because the clusters from the same cell are seeded in the same physical proximity.

Example 9

Method of Making Flow Cell Device with a Hydrogel Pillar

The following example demonstrates a method of making a flow cell device having a hydrogel deposited thereon in the form of pillars.

Hydrogel beads were prepared having genetic material encapsulated therein. To prepare the hydrogel beads, the following process was used.

A hydrogel solution of 12% (w/v) was prepared from 40% acrylamide/bis 19:1 (BioRad #161-0144) diluted with deionized water. A 40% (w/v) acrylamide/N,N'-bis(acryloyl) cystamine (BACy) (19:1) monomer stock solution (3.8 g of acrylamide, 0.2 g of BACy, and 6 mL of double distilled (dd)

H₂O) was prepared, and the final volume brought to 10 mL. The solution was prepared by first dissolving the acrylamide in 6 mL of ddH₂O, which was then used to dissolve the BACy. The dissolution of the monomers is endothermic, so heating the mixture slightly assists help completely dissolve the monomers. The hydrogel solution was maintained at 4° C. until use. 35 µL of saturated potassium persulfate solution (KPS; Sigma) was added to 200 µL of 12% hydrogel solution and mixed well. This hydrogel solution may be used to encapsulate genetic material, including DNA or cells, as described herein.

For DNA encapsulation, 20 µL of Coriell DNA solution (10 ng/µL) was added to the 235 µL of hydrogel/KPS solution. 20 µL of the hydrogel solution with Coriell DNA was added into each sample well of a droplet generator plate (BioRAD QX200), and 70 µL of oil was add to each well. After loading the plate to the droplet generator for 2 minutes, 20,000 droplets were formed. 50 µL of TEMED oil (25 µL TEMED in 600 µL mineral oil) was added into each droplet collected well to cross-link the beads. After 15 minutes of incubation, the hydrogel was fully cross-linked. The hydrogel beads containing Coriell DNA were loaded directly into a MiSeq™ Flow cell (Illumina, Inc., San Diego, Calif.) followed by a wash with PR2, as shown in FIG. 14. The hydrogel beads had a diameter of around 120 µm, which causes them to be fixed within the 100 µm high flow cell channel, forming pillars within the flow cell device. The flow cell device having hydrogel beads captured therein was then ready for DNA processing.

For cell encapsulation, samples containing *E. coli* cells stored at −80° C. were thawed at room temperature. 100 µL, of bacterial solution was transferred to a sterile 1.7 mL tube, and the sample was washed once with 1 mL 0.85% NaCl. The sample was pelleted and wash solution is removed. The bacteria pellet was saved for mixture with the hydrogel solution described as follows.

5 µL, of *E. coli* resuspension in PR2 was transferred in a clean PCR tube, 200 µL of the hydrogel plus KPS mix was added and mixed well. 20 µL *E. coli* polymer mix solution as described above was added into each sample well on a droplet generator plate (BioRAD QX200), and 70 µL of oil in each oil well was added. After loading the plate to droplet generator, around 20,000 droplets were formed in 2 minutes, and 50 µL of TEMED oil (25 µL TEMED in 600 µL mineral oil) was added into each droplet collected well. After 15 minutes incubation, the hydrogel was fully cross-linked. The beads were directly loaded into a MiSeq™ Flow cell followed by PR2 wash, and the gel beads had a diameter of around 120 µm, and became stuck inside the 100 µm high flow cell channel. The flow cell may then be used for processing the bacterial cells and the nucleic acids for nucleic acid library preparation.

Figure 16A:
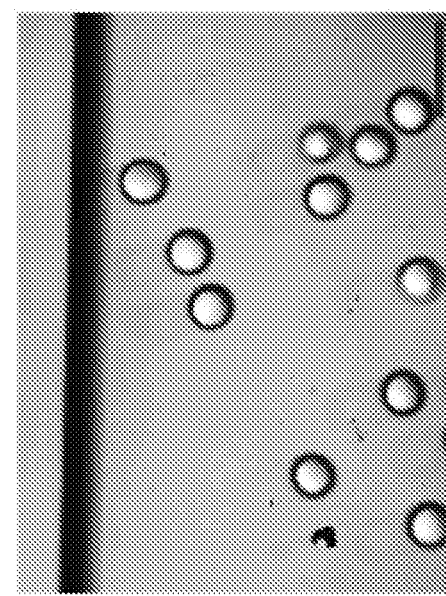
FIGS. 16A-16C depict the hydration of hydrogel beads in one example described herein.
Figure 16B:
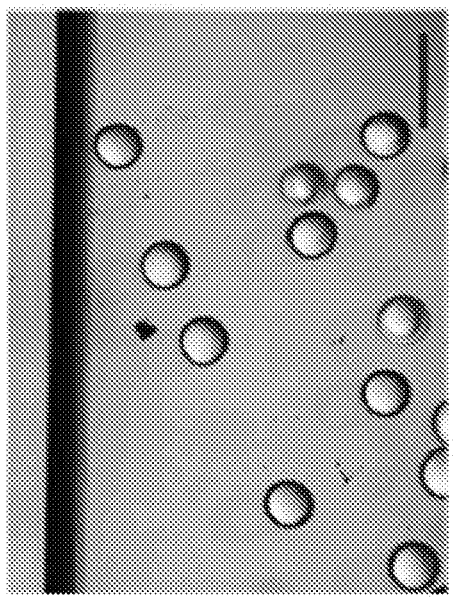
Figure 16C:
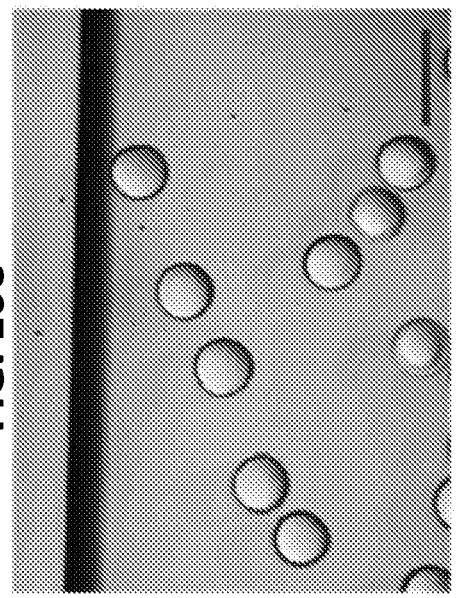

The hydrogel beads that contain the Coriell DNA or bacterial cells can be dehydrated to shrink the bead size prior to introducing the beads to the flow cell device. As shown in FIGS. 16A-16C, dehydrated beads containing the samples were engineered to be dynamically tuned by tailoring their hydration level. Dehydrated beads of about 70 µm (FIG. 16A) can readily be loaded into a flow cell having a channel height of 100 µm. As the hydrogel beads hydrate, they begin to enlarge (FIG. 16B), and eventually reach their original size of 105 µm at full hydration (FIG. 16C).

Figure 15C:
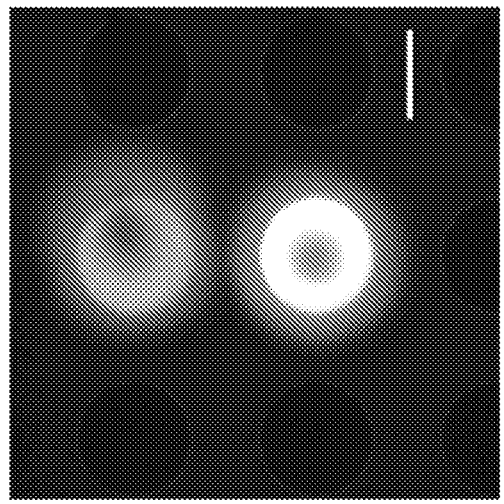
FIGS. 15A-15C depict an example of a patterned surface to capture hydrogel beads.
Figure 15B:
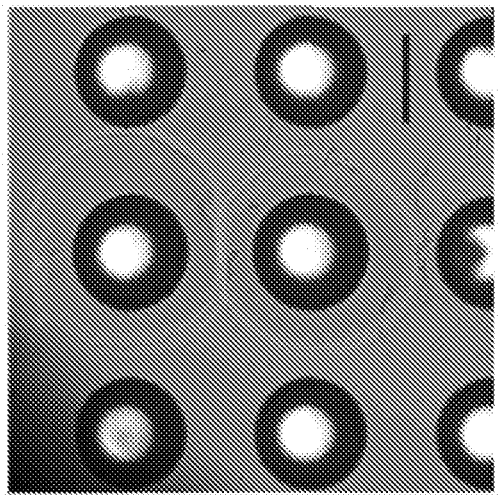
Figure 15A:
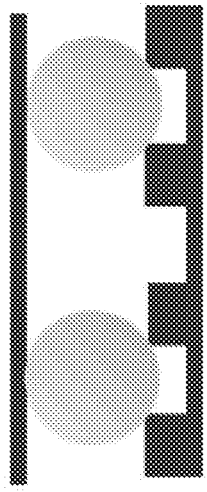

As shown in FIGS. 15A-15C, the flow cell device can include an etched surface that includes a pattern in order to individually separate and locate each hydrogel bead. A patterned array of microwells can be used to capture the hydrogel beads while they are in the dehydrated condition. Reagent may then be flowed through the flow cell to rehydrate the hydrogel beads to fix them in the channel and continue on with the downstream assays. The device can be a silicon based or glass substrate coated with hydrophobic material (which can be CYTOP, Fluoropel®, or Teflon®, or other hydrophobic material), and then photo-lithographically patterned with arrays of microwells (diameters and pitches vary with targeted hydrogel bead sizes) and etched out, so that the wells may be etched or the surface functionalized to capture hydrogel beads with the array. The patterned surface of the flow cell device may be used for increasing the quantity of hydrogel beads within the flow cell device and for the precise release of DNA at designated locations within the flow cell device.

Example 10

DNA Library Preparation in a Flow Cell Device

The following example demonstrate a method of preparing a DNA library on a flow cell device that has a hydrogel deposited therein in the form of hydrogel pillars.

The flow cell device as described in Example 9 having hydrogel beads fixed therein, forming hydrogel columns was used in DNA library preparation. Tn5 transposome reagent (Nextera™, Illumina Inc.) was loaded in to the flow cell and incubated for five minutes at 55° C. The adapters containing P5 and P7 ends were inserted to the DNA. 50 µL of stop buffer was loaded into the flow cell to knock out the Tn5 enzymes. Extension mix with Bsu polymerase and nucleotides for gap fill was loaded into the flow cell device to prepare the nucleic acid library, which was prepared and pinned inside the hydrogel bead matrix. PR2 wash buffer was loaded onto the flow cell device, and the temperature was raised to 90° C. for three minutes to denature the DNA library, which diffused out of the hydrogel beads. The temperature was then decreased to 60° C. for six minutes, 40° C. for two minutes, and 20° C. for two minutes to allow the single stranded DNA library to hybridize to the surface P5/P7 primers for cluster amplification. The flow cell was used directly in a 30-cycle bridge amplification, linearization, and sequencing primer fabrication. 2×150 cycle of sequencing was then performed and the determined sequences aligned with the Coriell sequences.

Figure 19B:
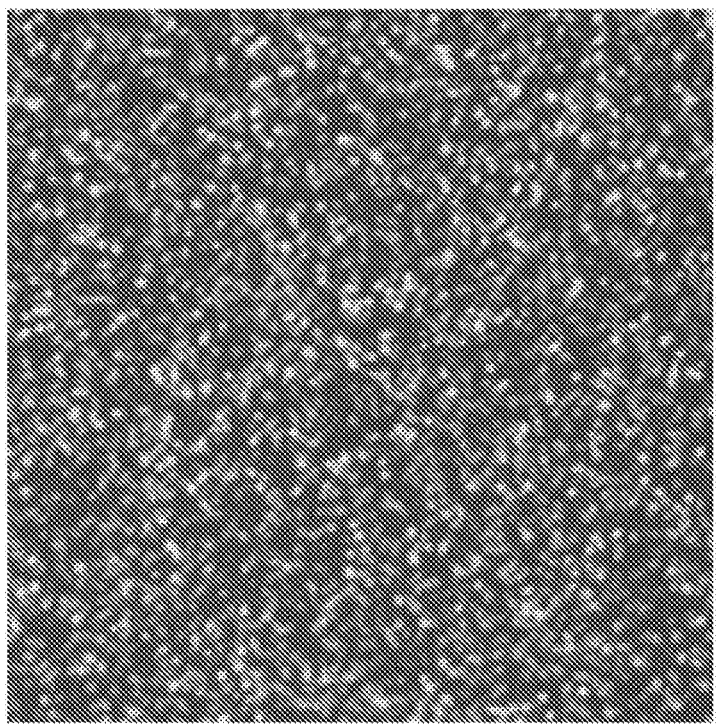
FIGS. 19A-19B depict fluorescent imaging of hydrogel containing stained human gDNA (FIG. 19A) and cluster gradient density of seeded amplified DNA (FIG. 19B). Scale bar, 100 µm.
Figure 19A:
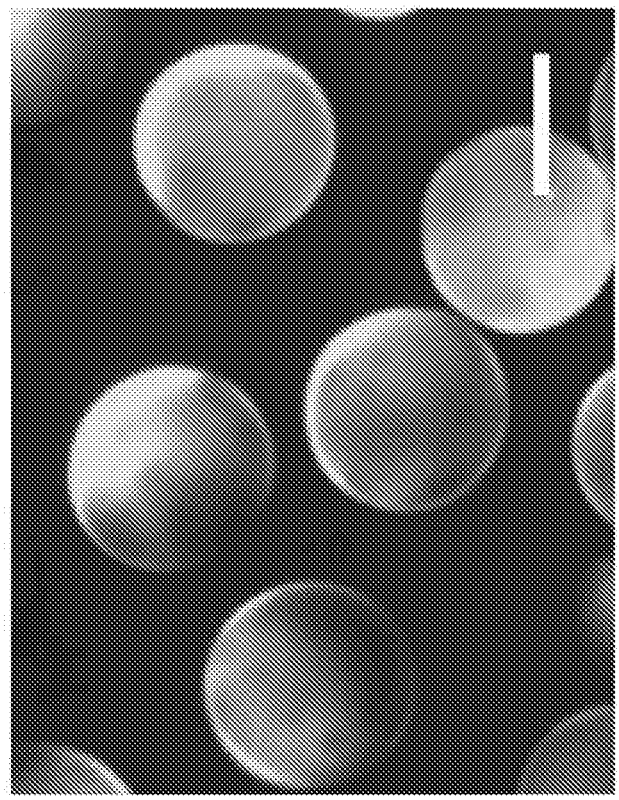
Figure 20B:
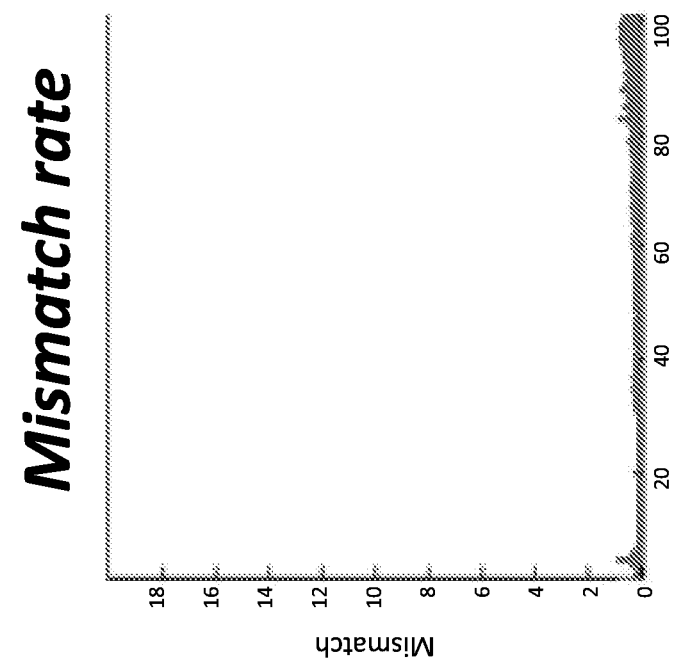
FIGS. 20A-20B provide the sequencing results of human gDNA that was prepared and sequenced on a flow cell device.
Figure 20A:
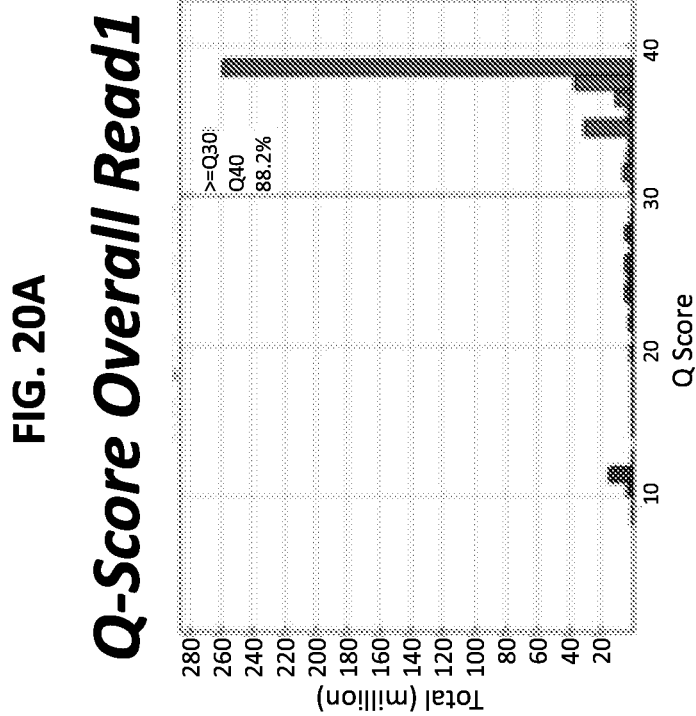

FIGS. 19A and 19B shows fluorescent imaging of stained hydrogel beads containing Coriell DNA (FIG. 19A) and cluster gradient density of seeded amplified DNA (FIG. 19B). The sequencing results of human gDNA is provided in FIG. 20. FIG. 20A is an overall Q-Score of the reads from a single experiment. FIG. 20B shows the mismatch rate from the same experiment. The sequencing results included 151, 101 clusters/tile, 92% clusters, 67% alignment, 0.41% mismatch rate, and a median length of 186.

Example 11

DNA Isolation and Library Preparation from Bacterial Cells in a Flow Cell Device The following example demonstrates a method of isolating DNA from bacterial cells in a flow cell device and preparing a DNA library on the flow cell device that has a hydrogel deposited therein in the form of hydrogel pillars encapsulating bacterial cells.

The flow cell device of Example 9 having hydrogel beads with bacterial cells encapsulated therein was provided. 100 µL of bacterial lysis reagents (Life Technologies, 0.5 mg lysozyme in 100 µL resuspension buffer Charge Switch kit) was loaded into the flow cell and incubated at 37° C. for 10 minutes. Proteinase K reagent was then loaded onto the flow cell and incubated at 55° C. for 20 minutes to fully digest the proteins. At this step, the *E. coli* gDNA was exposed but pinned inside the hydrogel beads, which were trapped in the flow cell device. After washing with PR2, Tn5 transposome reagent (Nextera™, Illumina Inc.) was loaded into the flow cell, and incubated at 55° C. for five minutes. Adapters containing P5 and P7 ends were inserted to the DNA. 50 µL of stop buffer was loaded onto the flow cell device to deactivate the Tn5 enzymes. An extension mix containing Bsu polymerase and nucleotides for gap filling was loaded onto the device, thus preparing an *E. coli* nucleic acid library, which was pinned inside the hydrogel beads that were trapped within the flow cell device. PR2 wash buffer was then added, and the temperature was raised to 90° C. for three minutes to denature the DNA library, which diffused out of the hydrogel beads. The temperature was then decreased to 60° C. for six minutes, 40° C. for two minutes, and 20° C. for two minutes to allow the single stranded DNA library to hybridize to the surface P5/P7 primers for cluster amplification. The flow cell was used directly in a 30-cycle bridge amplification, linearization, and sequencing primer fabrication. 2×150 cycle of sequencing was then performed and the determined sequences were aligned with *E. coli* sequences.

FIG. 21A schematically illustrates the process of preparing a nucleic acid library, consistent with Example 11. The cells were isolated in hydrogel beads, loaded onto a flow cell device, and rehydrated to fix the hydrogel bead within the flow cell device. Lysis reagent lysed cells in the hydrogel beads, and library preparation was performed on the bacterial DNA. The DNA was then released and seeded on the surface of the flow cell device surrounding the beads. As shown in FIG. 21B, the DNA library was encapsulated within the hydrogel beads prior to release, and diffused from the hydrogel beads after release (FIG. 21C). Fluorescent imaging of SYTOX dyed clusters revealed distinct clusters in close proximity to the original gel beads (FIG. 21D). Scale bars=50 µm.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

All combinations of the foregoing concepts and all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

It will be apparent that the precise details of the disclosed methods may be varied or modified without departing from the spirit of the described examples. We claim all such modifications and variations that fall within the scope and spirit of the claims below.

It is claimed:

1. A method, comprising:
    loading degradable hydrogel beads onto a sequencing flow cell under conditions sufficient for capture of the degradable hydrogel beads on a surface of the sequencing flow cell, wherein:
    the degradable hydrogel beads contain sequencing libraries prepared from encapsulated genetic material; or
    the degradable hydrogel beads contain encapsulated genetic material, and the method further comprises preparing sequencing libraries in the captured degradable hydrogel beads from the genetic material;
    loading a liquid diffusion barrier onto the sequencing flow cell that surrounds the hydrogel beads; and
    degrading the captured hydrogel beads in the presence of the liquid diffusion barrier to substantially inhibit diffusion of the sequencing libraries beyond a diameter of the corresponding hydrogel bead and to allow transport and seeding of the sequencing libraries to the surface of the sequencing flow cell in relative close proximity of a footprint of the corresponding hydrogel bead.

2. The method of claim 1, wherein the genetic material is selected from at least one of target nucleic acid molecules, cells, and cell lysate comprising target nucleic acid molecules.

3. The method of claim 1, wherein the sequencing libraries comprise DNA or RNA of at least 150 nucleotides in length.

4. The method of claim 1, wherein the liquid diffusion barrier is an oil, a viscous aqueous solution, or a combination thereof.

5. The method of claim 4, wherein the oil is mineral oil, silicone oil, perfluorinated oil, or a combination of two or more thereof.

6. The method of claim 4, wherein the viscous aqueous solution is a solution containing poly-ethylene glycol (PEG), poly-vinyl-pyrrolidone, pluronic dextran, sucrose, poly(N-isopropylacrylamide) or polyethylene oxide-polypropylene oxide-polyethylene oxide (PEO-PPO-PEO)/laponite, or a combination of two or more thereof.

7. The method of claim 1, wherein the hydrogel beads are degraded by:
    (a) contacting the hydrogel beads with a reagent that cleaves a reversible crosslinker that crosslinks polymers of the hydrogel;
    (b) heating the hydrogel beads to about 90° C.;
    (c) exposing the hydrogel beads to a wavelength of light that cleaves a photo-cleavable crosslinker that crosslinks polymer of the hydrogel; or
    (d) a combination of (a) and (b); (a) and (c); (b) and (c); or (a), (b), and (c).

8. The method of claim 7, wherein the reagent comprises dithiothreitol (DTT), tris(2-carboxyethyl)phosphine (TCEP), tris(3-hydroxypropyl)phosphine (THP), or a combination of two or more thereof.

9. The method of claim 1, wherein the hydrogel beads have a diameter of from about 5 µm to about 120 µm.

10. The method of claim 1, wherein the hydrogel beads are hollow hydrogel beads comprising hollow cores comprising the genetic material.

11. The method of claim 1, wherein the hydrogel beads comprise pores having a diameter of sufficient size to allow diffusion of chemicals through the hydrogel beads while retaining the encapsulated sequencing libraries.

12. The method of claim 11, wherein the pores have a diameter of from about 10 nm to about 100 nm.

13. The method of claim 1, wherein preparing the sequencing libraries comprises performing a tagmentation reaction on target nucleic acid molecules within the hydrogel beads.

14. The method of claim 13, wherein the tagmentation reaction comprises contacting the target nucleic acid molecules with a transposase mixture comprising adapter sequences and transposomes.

15. The method of claim 1, wherein the capture of the hydrogel beads on the surface of the sequencing flow cell comprises:
    physical constraint of the hydrogel beads on the surface of the sequencing flow cell;
    specific binding of a first member of a specific binding pair on the hydrogel beads to a second member of the specific binding pair on the surface of the sequencing flow cell,
    or both.

16. The method of claim 15, comprising the physical constraint of the hydrogel beads on the surface of the sequencing flow cell, wherein the diameter of the hydrogel beads is from about 5% to about 30% greater than the height of the flow cell to constrain the beads in the flow cell.

17. The method of claim 1, wherein the diameter of the hydrogel beads is about 110 μm, and the height of the sequencing flow cell is about 100 μm.

18. The method of claim 15, wherein the sequencing flow cell is a patterned flow cell, and the second member of the specific binding pair is located at wells of the patterned flow cell.

19. The method of claim 1, wherein the sequencing libraries are not barcoded to identify individual hydrogel beads.

20. The method of claim 1, further comprising amplifying target nucleic acid molecules encapsulated within the degradable hydrogel beads.

21. The method of claim 20, wherein the amplification involves multiple displacement amplification.

22. The method of claim 20, wherein the encapsulated target nucleic acid molecules are genomic DNA and the amplification involves whole-genome amplification.

23. The method of claim 1, wherein a location on the surface of the flow cell of sequencing libraries seeded from respective degradable hydrogel beads is used as a spatial index for reads generated from the sequencing of the sequence libraries.

24. The method of claim 1, wherein each of the hydrogel beads is formed using an outer hydrogel layer and an inner hydrogel layer encapsulated by the outer hydrogel layer.

25. A method, comprising:
    loading degradable hydrogel beads onto a sequencing flow cell under conditions sufficient for capture of the degradable hydrogel beads on a surface of the sequencing flow cell, wherein:
    the degradable hydrogel beads contain sequencing libraries prepared from encapsulated genetic material; or
    the degradable hydrogel beads contain encapsulated genetic material, and the method further comprises preparing sequencing libraries in the captured degradable hydrogel beads from the genetic material;
    loading a liquid diffusion barrier comprising oil onto the sequencing flow cell that surrounds the hydrogel beads and fills a void volume between the hydrogel beads; and
    degrading the captured hydrogel beads by heating the flow cell in the presence of the liquid diffusion barrier to substantially inhibit diffusion of the sequencing libraries beyond a diameter of the corresponding hydrogel bead and to allow transport and seeding of the sequencing libraries to the surface of the sequencing flow cell in relative close proximity of a footprint of the corresponding hydrogel bead.

* * * * *

UNITED STATES PATENT AND TRADEMARK OFFICE
CERTIFICATE OF CORRECTION

| | | |
|---|---|---|
| PATENT NO. | : 11,352,668 B2 | Page 1 of 1 |
| APPLICATION NO. | : 16/626115 | |
| DATED | : June 7, 2022 | |
| INVENTOR(S) | : Khurana et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 26 days.

Signed and Sealed this
Eighteenth Day of February, 2025

Coke Morgan Stewart
*Acting Director of the United States Patent and Trademark Office*